(12) United States Patent
Sheffield et al.

(10) Patent No.: US 7,756,584 B2
(45) Date of Patent: Jul. 13, 2010

(54) METHODS AND APPARATUS FOR EFFECTUATING A LASTING CHANGE IN A NEURAL-FUNCTION OF A PATIENT

(75) Inventors: W. Douglas Sheffield, Seattle, WA (US); Andrew D. Firlik, New Canaan, CT (US); Katrina S. Firlik, New Canaan, CT (US)

(73) Assignee: Advanced Neuromodulation Systems, Inc., Plano, TX (US)

( * ) Notice: Subject to any disclaimer, the term of this patent is extended or adjusted under 35 U.S.C. 154(b) by 986 days.

(21) Appl. No.: 10/260,720

(22) Filed: Sep. 27, 2002

(65) Prior Publication Data

US 2003/0130706 A1 Jul. 10, 2003

Related U.S. Application Data

(63) Continuation-in-part of application No. 09/802,808, filed on Mar. 8, 2001, now Pat. No. 7,010,351.

(60) Provisional application No. 60/325,872, filed on Sep. 28, 2001, provisional application No. 60/217,981, filed on Jul. 13, 2000.

(51) Int. Cl.
*A61N 1/08* (2006.01)
(52) U.S. Cl. ......................... 607/45; 600/544
(58) Field of Classification Search ............... 607/2, 607/45, 46; 600/544, 545; 606/130
See application file for complete search history.

(56) References Cited

U.S. PATENT DOCUMENTS

| | | | |
|---|---|---|---|
| 2,716,226 A | 8/1955 | Jonas | |
| 2,721,316 A | 10/1955 | Shaw | |
| 3,628,193 A | 12/1971 | Collins | |
| 3,650,276 A | 3/1972 | Burghele et al. | |
| 3,850,161 A | 11/1974 | Liss | |
| 3,918,461 A | 11/1975 | Cooper | |
| 4,019,518 A | * 4/1977 | Maurer et al. | 607/59 |
| 4,030,509 A | 6/1977 | Heilman et al. | |
| 4,125,116 A | 11/1978 | Fischell | |
| 4,140,133 A | 2/1979 | Kastrubin et al. | |
| 4,214,804 A | 7/1980 | Little | |

(Continued)

FOREIGN PATENT DOCUMENTS

DE 19750043 A1 5/1999

(Continued)

OTHER PUBLICATIONS

U.S. Appl. No. 60/325,872, filed Sep. 28, 2001, Sheffield.

(Continued)

*Primary Examiner*—George R Evanisko
*Assistant Examiner*—Michael Kahelin
(74) *Attorney, Agent, or Firm*—Melissa Acosta; Christopher S. L. Crawford; Peter Lando

(57) ABSTRACT

The following disclosure is drawn to methods of electrically stimulating areas of the brain in which neuroplasticity are occurring. The stimulation site may be different than the region in the brain where neural activity is typically present to perform the particular neural function according to the functional organization of the brain. The disclosure provides methods of identify the location in which neuroplasticity is occurring, not occurring or expected to occur.

34 Claims, 23 Drawing Sheets

U.S. PATENT DOCUMENTS

| | | |
|---|---|---|
| 4,245,645 A | 1/1981 | Picard et al. |
| 4,308,868 A | 1/1982 | Jhabvala |
| 4,328,813 A | 5/1982 | Ray |
| 4,340,038 A | 7/1982 | McKean |
| 4,390,023 A | 6/1983 | Rise |
| 4,431,000 A | 2/1984 | Butler et al. |
| 4,474,186 A | 10/1984 | Ledley et al. |
| 4,541,432 A | 9/1985 | Molina-Negro et al. |
| 4,542,752 A | 9/1985 | DeHaan et al. |
| 4,590,946 A | 5/1986 | Loeb |
| 4,607,639 A | 8/1986 | Tanagho et al. |
| 4,646,744 A | 3/1987 | Capel |
| 4,702,254 A | 10/1987 | Zabara |
| 4,817,634 A | 4/1989 | Holleman et al. |
| 4,844,075 A | 7/1989 | Liss et al. |
| 4,865,048 A | 9/1989 | Eckerson |
| 4,869,255 A | 9/1989 | Putz |
| 4,903,702 A | 2/1990 | Putz |
| 4,969,468 A | 11/1990 | Byers et al. |
| 5,002,053 A | 3/1991 | Garcia-Rill et al. |
| 5,024,226 A | 6/1991 | Tan |
| 5,031,618 A | 7/1991 | Mullett |
| 5,044,368 A | 9/1991 | Putz |
| 5,054,906 A | 10/1991 | Lyons, Jr. |
| 5,063,932 A | 11/1991 | Dahl et al. |
| 5,092,835 A | 3/1992 | Schurig et al. |
| 5,121,754 A | 6/1992 | Mullett |
| 5,143,089 A | 9/1992 | Alt |
| 5,169,384 A | 12/1992 | Bosniak et al. |
| 5,184,620 A | 2/1993 | Cudahy et al. |
| 5,193,540 A | 3/1993 | Schulman et al. |
| 5,215,086 A | 6/1993 | Terry, Jr. et al. |
| 5,215,088 A | 6/1993 | Normann et al. |
| 5,224,491 A | 7/1993 | Mehra |
| 5,255,678 A | 10/1993 | Deslauriers et al. |
| 5,263,967 A | 11/1993 | Lyons, III et al. |
| 5,269,303 A | 12/1993 | Wernicke et al. |
| 5,271,417 A | 12/1993 | Swanson et al. |
| 5,282,468 A | 2/1994 | Klepinski |
| 5,299,569 A | 4/1994 | Wernicke et al. |
| 5,303,705 A | 4/1994 | Nenov |
| 5,304,206 A | 4/1994 | Baker, Jr. et al. |
| 5,314,458 A | 5/1994 | Najafi et al. |
| 5,358,513 A | 10/1994 | Powell, III et al. |
| 5,358,514 A | 10/1994 | Schulman et al. |
| 5,370,672 A | 12/1994 | Fowler et al. |
| 5,405,375 A | 4/1995 | Ayers et al. |
| 5,406,957 A | 4/1995 | Tansey |
| 5,411,540 A | 5/1995 | Edell et al. |
| 5,417,719 A | 5/1995 | Hull et al. |
| 5,423,864 A | 6/1995 | Ljungstroem |
| 5,441,528 A | 8/1995 | Chang et al. |
| 5,464,446 A | 11/1995 | Dreessen et al. |
| 5,520,190 A | 5/1996 | Benedict et al. |
| 5,522,864 A | 6/1996 | Wallace et al. |
| 5,537,512 A | 7/1996 | Hsia et al. |
| 5,540,734 A | 7/1996 | Zabara |
| 5,540,736 A | 7/1996 | Haimovich et al. |
| 5,549,655 A | 8/1996 | Erickson |
| 5,562,708 A | 10/1996 | Combs et al. |
| 5,575,813 A | 11/1996 | Edell et al. |
| 5,591,216 A | 1/1997 | Testerman et al. |
| 5,593,432 A | 1/1997 | Crowther et al. |
| 5,601,611 A | 2/1997 | Fayram et al. |
| 5,611,350 A | 3/1997 | John |
| 5,618,531 A | 4/1997 | Cherksey |
| 5,628,317 A | 5/1997 | Starkebaum et al. |
| 5,674,251 A | 10/1997 | Combs et al. |
| 5,674,264 A | 10/1997 | Carter et al. |
| 5,676,655 A | 10/1997 | Howard, III et al. |
| 5,683,422 A | 11/1997 | Rise |
| 5,702,429 A | 12/1997 | King |
| 5,707,334 A | 1/1998 | Young |
| 5,711,316 A | 1/1998 | Elsberry et al. |
| 5,713,922 A | 2/1998 | King |
| 5,713,923 A | 2/1998 | Ward et al. |
| 5,716,377 A | 2/1998 | Rise et al. |
| 5,722,401 A | 3/1998 | Pietroski et al. |
| 5,735,814 A | 4/1998 | Elsberry et al. |
| 5,750,376 A | 5/1998 | Weiss et al. |
| 5,752,911 A | 5/1998 | Canedo et al. |
| 5,752,979 A | 5/1998 | Benabid |
| 5,753,505 A | 5/1998 | Luskin |
| 5,769,778 A | 6/1998 | Abrams et al. |
| 5,772,591 A | 6/1998 | Cram |
| 5,782,798 A | 7/1998 | Rise |
| 5,782,873 A | 7/1998 | Collins |
| 5,792,186 A | 8/1998 | Rise |
| 5,797,970 A | 8/1998 | Pouvreau |
| 5,814,014 A | 9/1998 | Elsberry et al. |
| 5,814,092 A | 9/1998 | King |
| 5,824,021 A | 10/1998 | Rise |
| 5,824,030 A | 10/1998 | Yang et al. |
| 5,832,932 A | 11/1998 | Elsberry et al. |
| 5,833,603 A | 11/1998 | Kovacs et al. |
| 5,833,709 A | 11/1998 | Rise et al. |
| 5,843,148 A | 12/1998 | Gijsbers et al. |
| 5,843,150 A | 12/1998 | Dreessen et al. |
| 5,846,196 A | 12/1998 | Siekmeyer et al. |
| 5,865,842 A | 2/1999 | Knuth et al. |
| 5,871,517 A | 2/1999 | Abrams et al. |
| 5,873,849 A | 2/1999 | Bernard |
| 5,885,976 A | 3/1999 | Sandyk |
| 5,886,769 A | 3/1999 | Zolten |
| 5,893,883 A | 4/1999 | Torgerson et al. |
| 5,904,916 A | 5/1999 | Hirsch |
| 5,913,882 A | 6/1999 | King |
| 5,916,171 A | 6/1999 | Mayevsky |
| 5,925,070 A | 7/1999 | King et al. |
| 5,928,144 A * | 7/1999 | Real ........................... 600/378 |
| 5,938,688 A | 8/1999 | Schiff |
| 5,938,689 A | 8/1999 | Fischell et al. |
| 5,941,906 A | 8/1999 | Barreras, Sr. et al. |
| 5,964,794 A | 10/1999 | Bolz et al. |
| 5,975,085 A | 11/1999 | Rise |
| 5,978,702 A | 11/1999 | Ward et al. |
| 5,983,140 A | 11/1999 | Smith et al. |
| 6,006,124 A | 12/1999 | Fischell et al. |
| 6,011,996 A | 1/2000 | Gielen et al. |
| 6,016,449 A | 1/2000 | Fischell et al. |
| 6,018,682 A | 1/2000 | Rise |
| 6,021,352 A | 2/2000 | Christopherson et al. |
| 6,024,702 A | 2/2000 | Iversen |
| 6,026,326 A | 2/2000 | Bardy |
| 6,035,236 A | 3/2000 | Jarding et al. |
| 6,038,480 A | 3/2000 | Hrdlicka et al. |
| 6,040,180 A | 3/2000 | Johe |
| 6,042,579 A | 3/2000 | Elsberry et al. |
| 6,052,624 A | 4/2000 | Mann |
| 6,055,456 A | 4/2000 | Gerber |
| 6,057,846 A | 5/2000 | Sever, Jr. |
| 6,058,331 A | 5/2000 | King |
| 6,060,048 A | 5/2000 | Cherksey |
| 6,061,593 A | 5/2000 | Fischell et al. |
| 6,066,163 A | 5/2000 | John |
| 6,094,598 A | 7/2000 | Elsberry et al. |
| 6,095,148 A | 8/2000 | Shastri et al. |
| 6,104,956 A | 8/2000 | Naritoku et al. |
| 6,104,960 A | 8/2000 | Duysens et al. |
| 6,122,548 A | 9/2000 | Starkebaum et al. |
| 6,126,657 A | 10/2000 | Edwards et al. |
| 6,128,527 A * | 10/2000 | Howard et al. .............. 600/544 |
| 6,128,537 A | 10/2000 | Rise |
| 6,128,538 A | 10/2000 | Fischell et al. |

| | | | | | | |
|---|---|---|---|---|---|---|
| 6,132,361 | A | 10/2000 | Epstein et al. | 6,795,737 B2 | 9/2004 | Gielen et al. |
| 6,134,474 | A | 10/2000 | Fischell et al. | 6,810,286 B2 | 10/2004 | Donovan et al. |
| 6,149,612 | A * | 11/2000 | Schnapp et al. ............... 601/23 | 6,819,956 B2 | 11/2004 | DiLorenzo |
| 6,152,143 | A | 11/2000 | Edwards | 6,839,594 B2 | 1/2005 | Cohen et al. |
| 6,161,044 | A | 12/2000 | Silverstone | 6,850,802 B2 | 2/2005 | Holsheimer et al. |
| 6,161,045 | A | 12/2000 | Fischell et al. | 6,873,872 B2 | 3/2005 | Gluckman et al. |
| 6,161,047 | A | 12/2000 | King et al. | 6,892,097 B2 | 5/2005 | Holsheimer |
| 6,176,242 | B1 | 1/2001 | Rise | 6,895,280 B2 | 5/2005 | Meadows et al. |
| 6,190,893 | B1 | 2/2001 | Shastri et al. | 6,898,464 B2 | 5/2005 | Edell et al. |
| 6,198,958 | B1 | 3/2001 | Ives et al. | 6,907,296 B1 | 6/2005 | Doan et al. |
| 6,205,360 | B1 | 3/2001 | Carter et al. | 6,934,580 B1 | 8/2005 | Osorio et al. |
| 6,205,361 | B1 | 3/2001 | Kuzma et al. | 6,944,497 B2 | 9/2005 | Stypulkowski |
| 6,210,417 | B1 | 4/2001 | Baudino et al. | 6,944,501 B1 | 9/2005 | Pless |
| 6,221,908 | B1 | 4/2001 | Kilgard et al. | 6,949,081 B1 | 9/2005 | Chance |
| 6,227,203 | B1 | 5/2001 | Rise et al. | 6,959,215 B2 | 10/2005 | Gliner et al. |
| 6,230,049 | B1 | 5/2001 | Fischell et al. | 6,990,377 B2 | 1/2006 | Gliner et al. |
| 6,236,892 | B1 | 5/2001 | Feler | 7,006,859 B1 | 2/2006 | Osorio et al. |
| 6,246,912 | B1 | 6/2001 | Sluijter et al. | 7,010,351 B2 | 3/2006 | Firlik et al. |
| 6,251,669 | B1 | 6/2001 | Luskin | 7,024,247 B2 | 4/2006 | Gliner et al. |
| 6,263,225 | B1 | 7/2001 | Howard, III | 7,050,856 B2 | 5/2006 | Stypulkowski |
| 6,280,462 | B1 | 8/2001 | Hauser et al. | 7,107,097 B2 | 9/2006 | Stern et al. |
| 6,301,493 | B1 | 10/2001 | Marro et al. | 7,110,820 B2 | 9/2006 | Tcheng et al. |
| 6,304,787 | B1 | 10/2001 | Kuzma et al. | 7,184,840 B2 | 2/2007 | Stolz et al. |
| 6,319,241 | B1 | 11/2001 | King et al. | 7,187,968 B2 | 3/2007 | Wolf et al. |
| 6,339,725 | B1 | 1/2002 | Naritoku et al. | 7,187,977 B2 | 3/2007 | Paul, Jr. |
| 6,353,754 | B1 | 3/2002 | Fischell et al. | 2002/0028072 A1 | 3/2002 | Kashiyama |
| 6,354,299 | B1 | 3/2002 | Fischell et al. | 2002/0087201 A1 | 7/2002 | Firlik |
| 6,356,786 | B1 | 3/2002 | Rezai et al. | 2002/0099295 A1 | 7/2002 | Gill et al. |
| 6,356,792 | B1 | 3/2002 | Errico | 2002/0099412 A1 | 7/2002 | Fischell et al. |
| 6,360,122 | B1 | 3/2002 | Fischell et al. | 2002/0138101 A1 | 9/2002 | Suda et al. |
| 6,366,813 | B1 | 4/2002 | DiLorenzo | 2002/0169485 A1 | 11/2002 | Pless et al. |
| 6,375,666 | B1 | 4/2002 | Mische | 2003/0028072 A1 | 2/2003 | Fischell et al. |
| 6,405,079 | B1 | 6/2002 | Ansarinia | 2003/0074032 A1 | 4/2003 | Gliner |
| 6,418,344 | B1 | 7/2002 | Rezai et al. | 2003/0078633 A1 | 4/2003 | Firlik et al. |
| 6,427,086 | B1 | 7/2002 | Fischell et al. | 2003/0088274 A1 | 5/2003 | Gliner et al. |
| 6,456,886 | B1 | 9/2002 | Howard, III et al. | 2003/0097159 A1 | 5/2003 | Schiff et al. |
| 6,459,936 | B2 | 10/2002 | Fischell et al. | 2003/0097161 A1 | 5/2003 | Firlik et al. |
| 6,463,328 | B1 | 10/2002 | John | 2003/0125772 A1 | 7/2003 | Olson et al. |
| 6,464,356 | B1 | 10/2002 | Sabel | 2003/0125786 A1 | 7/2003 | Gliner et al. |
| 6,466,822 | B1 | 10/2002 | Pless | 2003/0130706 A1 | 7/2003 | Sheffield et al. |
| 6,473,639 | B1 | 10/2002 | Fischell et al. | 2003/0138550 A1 | 7/2003 | Salaam |
| 6,480,743 | B1 | 11/2002 | Kirkpatrick et al. | 2003/0149457 A1 | 8/2003 | Tcheng et al. |
| 6,484,059 | B2 * | 11/2002 | Gielen ................... 607/45 | 2003/0176901 A1 | 9/2003 | May |
| 6,487,450 | B1 | 11/2002 | Chen | 2003/0187490 A1 | 10/2003 | Gliner |
| 6,497,699 | B1 | 12/2002 | Ludvig et al. | 2003/0187491 A1 | 10/2003 | Greenberg et al. |
| 6,499,488 | B1 | 12/2002 | Hunter et al. | 2003/0195602 A1 | 10/2003 | Boling |
| 6,505,075 | B1 | 1/2003 | Weiner | 2004/0073270 A1 | 4/2004 | Firlik et al. |
| 6,507,755 | B1 | 1/2003 | Gozani et al. | 2004/0082847 A1 | 4/2004 | McDermott |
| 6,529,774 | B1 | 3/2003 | Greene | 2004/0088024 A1 | 5/2004 | Firlik et al. |
| 6,539,263 | B1 | 3/2003 | Schiff et al. | 2004/0092010 A1 | 5/2004 | Ruiz I Altaba et al. |
| 6,549,814 | B1 | 4/2003 | Strutz et al. | 2004/0092809 A1 | 5/2004 | DeCharms |
| 6,556,868 | B2 | 4/2003 | Naritoku et al. | 2004/0102828 A1 | 5/2004 | Lowry et al. |
| 6,567,696 | B2 | 5/2003 | Voznesensky et al. | 2004/0111127 A1 | 6/2004 | Gliner |
| 6,569,654 | B2 | 5/2003 | Shastri et al. | 2004/0131998 A1 | 7/2004 | Marom et al. |
| 6,591,138 | B1 | 7/2003 | Fischell et al. | 2004/0138550 A1 | 7/2004 | Hartlep et al. |
| 6,592,509 | B1 | 7/2003 | Hunter, Jr. | 2004/0158298 A1 | 8/2004 | Gliner et al. |
| 6,597,954 | B1 | 7/2003 | Pless et al. | 2004/0176831 A1 | 9/2004 | Gliner et al. |
| 6,615,065 | B1 | 9/2003 | Barrett et al. | 2004/0181263 A1 | 9/2004 | Balzer et al. |
| 6,622,048 | B1 | 9/2003 | Mann | 2004/0215287 A1 | 10/2004 | Swoyer et al. |
| 6,631,295 | B2 | 10/2003 | Rubinstein et al. | 2004/0236388 A1 | 11/2004 | Gielen et al. |
| 6,633,780 | B1 | 10/2003 | Berger | 2004/0243205 A1 | 12/2004 | Keravel et al. |
| 6,647,296 | B2 | 11/2003 | Fischell et al. | 2004/0249422 A1 | 12/2004 | Gliner et al. |
| 6,658,299 | B1 | 12/2003 | Dobelle | 2005/0004620 A1 | 1/2005 | Singhal et al. |
| 6,665,562 | B2 | 12/2003 | Gluckman et al. | 2005/0015129 A1 | 1/2005 | Mische |
| 6,684,105 | B2 | 1/2004 | Cohen et al. | 2005/0021104 A1 | 1/2005 | DiLorenzo |
| 6,687,525 | B2 | 2/2004 | Llinas | 2005/0021105 A1 | 1/2005 | Firlik et al. |
| 6,690,974 | B2 | 2/2004 | Archer et al. | 2005/0021106 A1 | 1/2005 | Firlik et al. |
| 6,708,064 | B2 | 3/2004 | Rezai | 2005/0021107 A1 | 1/2005 | Firlik et al. |
| 6,725,094 | B2 | 4/2004 | Saberski | 2005/0021118 A1 | 1/2005 | Genau et al. |
| 6,735,475 | B1 | 5/2004 | Whitehurst et al. | 2005/0033378 A1 | 2/2005 | Sheffield et al. |
| 6,764,498 | B2 | 7/2004 | Mische | 2005/0070971 A1 | 3/2005 | Fowler et al. |
| 6,782,292 | B2 | 8/2004 | Whitehurst | 2005/0075679 A1 | 4/2005 | Gliner et al. |
| 6,788,975 | B1 | 9/2004 | Whitehurst et al. | 2005/0075680 A1 | 4/2005 | Lowry et al. |

| | | | |
|---|---|---|---|
| 2005/0096701 | A1 | 5/2005 | Donovan et al. |
| 2005/0113882 | A1 | 5/2005 | Cameron et al. |
| 2005/0119712 | A1 | 6/2005 | Shafer |
| 2005/0154425 | A1 | 7/2005 | Boveja et al. |
| 2005/0154426 | A1 | 7/2005 | Boveja et al. |
| 2005/0182453 | A1 | 8/2005 | Whitehurst |
| 2005/0228451 | A1 | 10/2005 | Jaax et al. |
| 2006/0004422 | A1 | 1/2006 | De Ridder |
| 2006/0004423 | A1 | 1/2006 | Boveja et al. |
| 2006/0015153 | A1 | 1/2006 | Gliner et al. |
| 2006/0106430 | A1 | 5/2006 | Fowler et al. |
| 2006/0406431 | | 5/2006 | Wyler et al. |
| 2006/0129205 | A1 | 6/2006 | Boveja et al. |
| 2006/0173522 | A1 | 8/2006 | Osorio |
| 2006/0217782 | A1 | 9/2006 | Boveja et al. |
| 2006/0241717 | A1 | 10/2006 | Whitehurst et al. |
| 2006/0259094 | A1 | 11/2006 | Naisberg et al. |
| 2007/0088403 | A1 | 4/2007 | Wyler |
| 2007/0100398 | A1 | 5/2007 | Sloan |

FOREIGN PATENT DOCUMENTS

| | | |
|---|---|---|
| EP | 0214527 | 3/1987 |
| EP | 0319844 A1 | 6/1989 |
| EP | 0 998 958 A2 | 10/2000 |
| EP | 1145736 | 10/2001 |
| EP | 1180056 | 11/2003 |
| WO | WO 87/07511 | 12/1987 |
| WO | WO 94/07564 | 4/1994 |
| WO | WO 95/21591 | 8/1995 |
| WO | WO 97-45160 | 12/1997 |
| WO | WO 98-06342 | 2/1998 |
| WO | WO-0007494 | 12/2000 |
| WO | WO 01/97906 | 12/2001 |
| WO | WO 02/09811 | 2/2002 |
| WO | WO 02/36003 | 5/2002 |
| WO | WO 02/38031 | 5/2002 |
| WO | WO 02/38217 | 5/2002 |
| WO | WO-02072194 | 9/2002 |
| WO | WO-02073526 | 9/2002 |
| WO | WO-03/082402 | 3/2003 |
| WO | WO-03026739 | 4/2003 |
| WO | WO-03/043690 | 5/2003 |
| WO | WO-03035163 | 5/2003 |
| WO | WO-03/101532 | 12/2003 |

OTHER PUBLICATIONS

U.S. Appl. No. 60/325,978, filed Sep. 28, 2001, Gliner.
U.S. Appl. No. 10/072,700, filed Feb. 7, 2002, Firlik.
U.S. Appl. No. 09/978,134, filed Oct. 15, 2001, Gliner.
Barr, Deborah et al., "Induction and Reversal of Long-Term Potentiation by Low-and High- Intensity Theta Pattern Stimulation," The Journal of Neuroscience, 15(7): pp. 5402-5410 (Jul. 1995).
Behrens, T. et al., "Non-invasive mapping of connections between human thalamus and cortex using diffusion imaging," Nature Neuroscience, vol. 6 No. 7, pp. 750-757 (Jul. 2003).
Benabid, A.L. et al, "Chronic electrical stimulation of the ventralis intermedius nucleus of the thalamus as a treatment of movement disorders," J. Neurosurg., Apr. 1997, 86(4); 737; http://www.ncbi.nlm.nih.gov; [accessed Nov. 18, 2003].
Brain Electrical Stimulation to Enhance Recovery After Stroke. ClinicalTrials.gov. [Retrieved on Dec. 22, 2005]. Retrieved from the Internet <URL http://www.clinicaltrials.gov/ct/show/NCT00085657?order=2>.
Burnett, Mark G. et al., "Diffuse optical measurement of blood flow, blood oxygenation, and metabolism in a human brain during sensorimotor cortex activation," Optics Letters, vol. 29, No. 15, pp. 1766-1768 (Aug. 1, 2004).
Cytokines Web Clinical Significance. Cytokines Web, 2 pages. [Retrieved on Sep. 2, 2005]. Retrieved from the internet: <URL: http://cmbi.bjmu.edu.cn/cmbidata/cgf/CGF_Database/cytweb/roles/index.html>.
De Ridder, Dirk et al., "Magnetic and electrical stimulation of the auditory cortex for intractable tinnitus," Journal Neurosurg., vol. 100, pp. 560-564, (Mar. 2004).
Di Lazzaro, V. et al., "Theta-burst repetitive transcranial magnetic stimulation suppressess specific excitatory circuits in the human motor cortex," Physiology in Press; published online on Apr. 21, 2005 as 10.1113/jphysio.2005.087288.
Ding, Yuemin et al., "Neural Plasticity After Spinal Cord Injury," Current Pharmaceutical Design vol. 11, No. 11, pp. 1441-1450, Abstract Only- 1 page (Apr. 2005).
Duncan, Pamela W. et al., "Defining post-stroke recovery: implications for design and interpretation of drug trials," Neuropharmacology vol. 39, pp. 835-841 (2000).
Fregni, Felipe et al., "Anodal Transcranial Direct Current Stimulation of Prefrontal Cortex Enhances Working Memory," Experimental Brain Research vol. 166, No. 1, pp. 23-30 (Sep. 2005).
Hagemann, Georg et al., "Increased Long-Term Potentiation in the Surround of Experimentally Induced Focal Cortical Infarction," Annals of Neurology, vol. 44, No. 2, pp. 255-258 (Aug. 1998).
Hayakawa, Toshiji et al., "Changes in Cerebral Oxygenation and Hemodynamics During Obstructive Sleep Apneas," Chest, vol. 109, pp. 916-921 (1996).
Hoshi, Yoko et al., "Detection of dynamic changes in cerebral oxygenation coupled to neuronal function during mental work in a man," Neuroscience Letters, vol. 150, pp. 5-8 (1993).
Hoshino et al., "Application of multichannel near-infrared spectroscopic topography to physiological monitoring of the cortex during cortical mapping: technical case report," Surgical Neurology, vol. 64, pp. 272-275 (2005).
Huang, Ying-Zu et al., "Theta Burst Stimulation of the Human Motor Cortex," Neuron, vol. 45, pp. 201-206 (Jan. 20, 2005).
Hummel, Friedhelm et al., "Effects of non-invasive cortical stimulation on skilled motor function in chronic stroke," Brain Advance Access, Jan. 5, 2005, pp. 1-10, Brain.
Kilgard, Michael et al., "Cortical Map Reorganization Enabled by Nucleus Basalis Activity," Science, vol. 279 pp. 1714-1717 (Mar. 13, 1998).
L-DOPA dyskinesias. BioChemistry of PD. [Retrieved on Dec. 22, 2005]. Retrieved from the internet <URL http://www.mayo.edu/fdp/pd-info/dyskinesias.htm>.
Lang, Nicolas et al., "Preconditioning with Transcranial Direct Current Stimulation Sensitizes the Motor Cortex to Rapid-Rate Transcranial Magnetic Stimulation and Controls the Direction of After-Effects," Biol Psychiatry 2004:56:634-639, 2004 Society of Biological Psychiatry.
Larson, John et al., "Reversal of LTP by theta frequency stimulation," Brain Research, 600: pp. 97-102 (1993).
Lazar, M. et al., "White Matter Tractography Using Diffusion Tensor Deflection," Human Brain Mapping, 18:306-321, (2003).
Mansur, C.G., et al., "A sham stimulation-controlled trial of rTMS of the unaffected hemisphere in stroke patients," Neurology, vol. 64, pp. 1802-1804 (2005).
Martin et al, "Transcranial Magnetic Stimulation as a Complementary Treatment for Aphasia," Semin Speech Language, vol. 25, pp. 181-191 (2004) Abstract Only- 1 page.
Meyerson, B.A. et al., "Motor Cortex Stimulation as Treatment of Trigeminal Neuropathic Pain," Acta Neurochirurgica Supplementum, vol. 58, pp. 150-153 (1993).
Nitsche, Michael A. et al., "Level of action of cathodal DC polarisation induced inhibition of the human motor cortex," Dec. 2, 2002, Clinical Neurophysiology 114 (2003) 600-604.
Nitsche, Michael A., et al. "Facilitation of Implicit Motor Learning by Weak Transcranial Direct Current Stimulation of the Primary Motor Cortex in the Human," Journal of Cognitive Neuroscience 15:4, pp. 619-626, 2003 Massachusetts Institute of Technology.
Panchanathan, Sethuraman et al, "Rehabilitation of patients with hemispatial neglect using visual-haptic feedback in Virtual reality environment," [Retrieved on Dec. 22, 2005]. Retrieved from the internet <URL http://www.public.asu.edu/~tmcdani/publications.htm>.

Paulus, W., "Supplements to Clinical Neurophysiology," Transcranial Magnetic Stimulation and Transcranial Direct Current Stimulation (Supplements to Clinical Neurophysiology; vol. 56), pp. 249-254, 2003 Elsevier Science, B.V.

Paulus, Walter, "Toward Establishing a Therapeutic Window for rTMS by Theta Burst Stimulation," Neuron, vol. 45, pp. 181-183 (Jan. 20, 2005).

Penn, Michael, "Stemming Parkinson's," On Wisconsin Alumni Magazine, Summer 2003, [Retrieved on Dec. 22, 2005]. Retrieved from the internet <URL http://www.uwalumni.com/onwisconsin/2003_summer/research.html>.

Schaefer, Pamela W. et al., "Assessing Tissue Viability with MR Diffusion and Perfusion Imaging," AJNR, 24: pp. 436-443 (Mar. 2003).

Schiene, Klaus et al., "Neuronal Hyperexcitability and Reduction of GABA-Receptor Expression in the Surround of Cerebral Photothrombosis," Journal of Cerebral Blood Flow and Metabolism, vol. 16, No. 5, pp. 906-914 (1996).

SCIRun. Scientific Computing and Imaging Institute, 2 pages. [Retrieved on Jul. 24, 2005]. Retrieved from the internet: <URL: <http://sofware.sci.utah.edu/scirun.html>>.

Strangman, Gary et al., "A Quantitative Comparison of Simultaneous BOLD fMRI and NIRS Recordings during Functional Brain Activation," NeuroImage, vol. 17, pp. 719-731 (2002).

Strangman, Gary et al., "Factors affecting the accuracy of near-infrared spectroscopy concentration calculations for focal changes in oxygenation parameters," NeuroImage, vol. 18, pp. 865-879 (2003).

Strangman, Gary et al., "Non-Invasive Neuroimaging Using Near-Infrared Light," Biological Psychiatry, vol. 52, pp. 679-693 (2002).

Strens, Lucy et al., "The ipsilateral Human Motor Cortex Can Functionally Compensate for Acute Contralateral Motor Cortex Dysfunction," Current Biology, vol. 13, pp. 1201-1205 (Jul. 15, 2003).

Taga, Gentaro et al., "Brain imaging in awake infants by near-infrared optical topogrpahy," PNAS, vol. 100, No. 19, pp. 10722-10727 (Sep. 16, 2003).

The GES 250 for Dense-Array EEG Research. Electrical Geodesics, Inc., 3 pages. [Retrieved on Aug. 25, 2005]. Retrieved from the internet: <URL: http://www.egi.com/ges250r_n.html>.

The INVOS Cerebral Oximeter. Somanetics, 1 page [Retrieved on Dec. 22, 2005]Retrieved from the internet <URL http://www.somanetics.net/invos.htm>.

Theoret, Hugo et al., "Exploring Paradoxical Functional Facilitation with TMS," Supplements to Clinical Neurophysiology, vol. 56, pp. 211-219 (2003).

Thomas, Carmen et al., "Do Children with aggressive behavior have temporal lobe changes?" Alasbimn Journal, Year 5, No. 19, 8 pages (Jan. 2003).

Toronov, Vlad et al., "Near-infrared study of fluctuations in cerebral hemodynamics during rest and motor stimulation: Temporal analysis and spatial mapping," Medical Physics, vol. 27, No. 4, pp. 801-815 (Apr. 2000).

Tractography. Absolute Astronomy Reference, 2 pages. [Retrieved on Jul. 24, 2005]. Retrieved from the internet: <URL: http://www.absoluteastronomy.com/encyclopedia/T/Tr/Tractography.htm>.

Tsubokawa, T. et al., "Chronic Motor Cortex Stimulation for the Treatment of Central Pain", Acta Neurochirurgica, Suppl. 52, pp. 137-139 (1991).

Tsubokawa, T. et al., "Treatment of Thalamic Pain by Chronic Motor Cortex Stimulation," PACE, vol. 14, pp. 131-134 (Jan. 1991).

Tsubokawa, T., "Chronic Motor Cortex Stimulation in Patients with Thalamic Pain," J. Neurosurg 78:393-401, (Mar. 1993).

Tuch, D. et al., "Conductivity Tensor Mapping of the Human Brain Using Diffusion Tensor MRI," Neurobiology, vol. 98 No. 20, pp. 11697-11701 (Sep. 25, 2001).

Weinand, Martin E. et al., "Cerebral blood flow and temporal lobe epileptogenicity," [Retrieved on Dec. 22, 2005]. Retrieved from the internet: <URL http://www.aans.org/education/journal/neurosurgical/nov96/1-5-3.asp>.

Yokoh, Arika et al., "Intermittent versus continuous brain retraction," Journal of Neurosurgery, vol. 58, pp. 918-923 (Jun. 1983).

Bluestone, Avraham Y. et al., "Three-dimensional optical tomography of hemodynamics in the human head," Optics Express, vol. 9, No. 6, pp. 272-286 (Sep. 10, 2001).

Bury, Scott et al., "The Effects of Behavioral Demand on Motor Cortical and Cerebellar Structural Plasticity After Brain Injury in Adult Rats," [Retrieved on Mar. 1, 2003]. Retrieved from the internet: <URL: http://www.mcmaster.ca/inabis98/schallert/bury0827/two.html#introduction>.

Cao, Yue et al., "Cortical Language Activation in Stroke Patients Recovering From Aphasia With Functional MRI," Stroke, vol. 30, pp. 2331-2340, Nov. 1999.

How Imagent™ Works. ISS Inc., 1 page [Retrieved on Oct. 14, 2005]. Retrieved from the internet: <URL http://www.iss.com/Products/imagent_fmri.html>.

Imagent™ Functional Brain Imaging System. ISS, Inc., 2 pages [Retrieved on Oct. 14, 2005]. Retrieved from the internet: <URL http://www.iss.com/Products/imagent.html>.

Imagent™ functional Near Infrared Imaging System (fNIRS) Brain Imaging Using Infrared Photons. ISS Inc., 8 pages [Retrieved on Oct. 14, 2005]. Retrieved from the internet: <URL http://www.iss.com/products/imagent/Imagent.pdf>.

Janicek, Milos J. et al., "Dynamic Infrared Imaging of Newly Diagnosed Malignant Lymphoma Compared with Gallium-67 and Fluorine-18 Fluorodeoxyglucose (FDG) Positron Emission Tomography," Technology in Cancer Research and Treatment, vol. 2, No. 6, pp. 571-577 (Dec. 2003).

Keyvani, Kathy et al., "Suppression of proteasome C2 contralateral to ischemic lesions in rat brain," Brain Research, vol. 858, pp. 386-392, 2000.

Nudo, Randolph J., et al., "Recovery after damage to motor cortical areas," Current Opinion in Neurobiology, vol. 9, Issue 6, pp. 740-747, Dec. 1, 1999.

Tang, Cha-Min et al., "Optical Coherence Tomography of the Human Basal Ganglion,"2003 Deep Brain Stimulation Consortium Meeting, Sep. 29-30, Washington DC.

Timmermann, Lars et al., "The cerebral oscillatory network of parkinsonian resting tremor," Brain, vol. 126, pp. 199-212, (2003).

Barres et al., "Proliferation of oligodendrocyte precursor cells depends on electrical activity in axons," Nature; Medical Research Council Developmental Neurobiology Programme, Department of Biology, University College, London, p. 258-260, (Jan. 21, 1993).

Bel, S. and Bauer, B.L., "Dorsal Column Stimulation (DCS): Cost to Benefit Analysis," Acta Neurochirurgica, Suppl. 52, pp. 121-123 (1991).

Bezard et al., "Cortical Stimulation and Epileptic Seizure: A Study of the Potential Risk in Primates," Neurosurgery, vol. 45, No. 2, Aug. 1999, 346-350.

Binder, J. M.D., "Functional Magnetic Resonance Imaging: Language Mapping," Neurosurgery Clinics of North America, vol. 8, No. 3, Jul. 1997, pp. 383-392.

Butefisch et al., "Mechanisms of use-dependent plasticity in the human motor cortex," Proc. Natl. Acad. Sci. USA, vol. 97, No. 7, pp. 3661-3665 (Mar. 2000).

Cheun et al., "Differentiation of a Stem Cell Line Toward a Neuronal Phenotype," Int. J. Devl. Neuroscience, vol. 9, No. 4, pp. 391-404 (1991).

Cicinelli et al., "Transcranial magnetic stimulation reveals an Interhemispheric asymmetry of cortical inhibition in focal epilepsy," Neurophysiology, vol. 11, No. 4 Mar. 20, 2000, pp. 701-707.

Cincotta et al., "Suprathreshold 0.3 Hz repetitive TMS prolongs the cortical silent period: potential implications for therapeutic trials in epilepsy," Clinical Neurophysiology, vol. 114, 2003, pp. 1827-1833, Elsevier Ireland Ltd.

Classen et al., "Rapid Plasticity of Human Cortical Movement Representation Induced by Practice," The Journal of Neurophysiology, vol. 79, No. 2, pp. 1117-1123 (Feb. 1998).

Cohen et al., "Studies of Neuroplasticity With Transcranial Magnetic Stimulation," The Journal of Clinical Neurophysiology, vol. 15, No. 4 (1998).

Cramer et al., "Use of Functional MRI to Guide Decisions in a clinical Stroke Trial," Stroke, Journal of the American Heart Association, May 2005, pp. e50-e52, American Heart Association, Dallas TX.

Cramer, S.C. and Bastings, E.P., "Mapping clinically relevant plasticity after stroke," Neuropharmacology vol. 19, No. 5, pp. 842-851 (Apr. 2000).

Dam et al., "Effects of Fluoxetine and Maprotiline on Functional Recovery in Poststroke Hemiplegic Patients Undergoing Rehabilitation Therapy," Stroke, vol. 27, No. 7, pp. 1211-1214 (Jul. 1996).

Ferrari, A. et al., "Immature human NT2 cells grafted into mouse brain differentiate into neuronal and glial cell types," FEBS Letters, Dec. 8, 2000, pp. 121-125, vol. 486, No. 2, Elsevier Science B.V., Amsterdam.

Feys et al., "Value of somatosensory and motor evoked potentials in predicting arm recovery after a stroke," (Oct. 1999).

Fregni et al., "Antiepileptic Effects of Repetitive Transcranial Magnetic Stimulation in Patients with Cortical Malformations: An EEG and Clinical Study," ASSFN Proceedings 2004, Stereotactic and Functional Neurosurgery, 2005, 83:57-62.

Gladstone et al., "Enhancing Recovery after Stroke with Noradrenergic Pharmacotherapy: A New Frontier?," Can J. Neurol. Sci., vol. 27, No. 2 (May 2000).

Gordon et al., "Parameters for direct cortical electrical stimulation in the human: histopathologic confirmation," Electroencephalography and clinical Neurophysiology, vol. 75, pp. 371-377 (1990).

Haglund, Michael M. et al., "Optical imaging of epileptiform and functional activity in human cerebral cortex," Nature, Aug. 20, 1992, pp. 668-671, vol. 358, Nature Publishing Group.

Hodge, Jr., C.J. and Boakye, M., "Biological Plasticity: The Future of Science in Neurosurgery," Neurosurgery, vol. 48, No. 1 (Jan. 2001).

Ishibashi, Tomoko et al., "Astrocytes Promote Myelination in Response to Electrical Impulses," Neuron 49, pp. 823-832, (Mar. 16, 2006).

Kauhanen et al., "Domains and Determinants of Quality of Life After Stroke Caused by Brian Infarction," Arch. Phys. Med. Rehabil., vol. 81, pp. 1541-1546 (Dec. 2000).

Kelly-Spratt, K. "Transfection of PC-12 cells: a model system for primary neuronal cells," Qiagen News, Customer application article, www.qiagen.com, Issue 4, 1998, 2 pages.

Kinoshita et al., "Electric cortical stimulation suppresses epileptic and background activities in neocortical epilepsy and mesial temporal lobe epilepsy," Clinical Neurophysiology, vol. 116, 2005, pp. 1291-1299, Elsevier Ireland Ltd.

Kopell et al., "The Continuing Evolution of Psychiatric Neurosurgery," CNS Spectrums, vol. 5, No. 10, pp. 20-31 (Oct. 2000).

Kossoff et al., "Effect of an External Responsive Neurostimulator on Seizures and Electrographic Discharges during Subdural Electrode Monitoring," Epilepsia 45(12):1560-1567, 2004, Blackwell Publishing, Inc.

Levy et al., "Functional MRI Evidence of Cortical Reorganization in Upper-Limb Stroke Hemiplegia Treated with Constraint-Induced Movement Therapy," American Journal of Physical Medicine & Rehabilitation, vol. 80, No. 1, pp. 4-7 (2001).

Lutsep et al., "Safety of Cortical Stimulation in Patients with Hemiparetic Stroke," Oasis, Online Abstract Submission and Invitation System—Program Planner, International Stroke Conference 2005, 1 pages, American Stroke Association.

Malenka, R.C. and Nicoll, R.A., "Long-Term Potenetiation—A Decade of Progress?," Neuroscience, vol. 285, No. 5435, Issue of Sep. 17, 1999, pp. 1870-1874.

Misawa et al., "Low-frequency transcranial magnetic stimulation for epilepsia partialis continua due to cortical dysplasia," Journal of the Neurological Sciences, vol. 234, 2005, pp. 37-39.

Motamedi et al., "Optimizing Parameters for Terminating Cortical Afterdischarges with Pulse Stimulation," Epilepsia 43(8):836-846, 2002, Blackwell Publishing, Inc.

Netz et al., "Reorganization of motor output in the non-affected hemisphere after stroke," Brain, 120, pp. 1579-1586 (1997).

Pascual-Leone et al., "Study and Modulation of Human Cortical Excitability With Transcranial Magnetic Stimulation," Journal of Clinical Neurophysiology, 1998, vol. 15, No. 4, pp. 333-343.

Rezai, "Neurostimulation," Neurological Research, vol. 22, No. 3 pp. 235-273 (Apr. 2000).

Robinson, Kenneth R., "The Responses of Cells to Electrical Fields: A Review," The Journal of Cell Biology, vol. 101, pp. 2023-2027 (Dec. 1985).

Rossi et al., "Effects of Repetitive Transcranial Magnetic Stimulation on Movement-related Cortical Activity in Humans," Cerebral Cortex, vol. 10, No. 8, pp. 802-808 (Aug. 2000).

Roux et al., "Chronic Motor Cortex Stimulation for Phantom Limb Pain: A Functional Magnetic Resonance Imagining Study: Technical Cast Report," Neurosurgery, vol. 48, No. 3 (Mar. 2001).

Saitou et al., "Cerebral Blood Volume and Oxygenation Among Poststroke Hemiplegic Patients: Effects of 13 Rehabilitation Tasks Measured by Near-Infrared Spectroscopy," Arch. Phys. Med. Rehabil., vol. 81 pp. 1348-1356 (Oct. 2000).

Schiff et al., "A neuromodulation strategy for rational therapy of complex brain injury states," Neurological Research, vol. 22 pp. 267-272 (Apr. 2000).

Shimizu et al., "Therapeutic efficacy of transcranial magnetic stimulation for hereditary spinocerebellar degeneration," Tohoku Journal of Experimental Medicine, 189(3):203-11 (Nov. 1999).

Siebner et al., "Lasting cortical activation after repetitive TMS of the motor cortex," Neurology 54, pp. 956-963 (Feb. 2000).

Sioutos et al. Continuous Regional Cerebral Cortical Blood Flow Monitoring in Head-injured Patients, Neurosurgery, vol. 36, No. 5, May 1995, pp. 943-949.

Stefan et al., "Introduction of plasticity in the human motor cortex by paired associative stimulation," Brian, vol. 123, No. 3, pp. 572-584 (Mar. 2000).

The National Institutes of Health (NIH) Consensus Development Program, "Surgery for Epilepsy," National Institutes of Health Consensus Development conference Statement, Mar. 19-21, 1990, 16 pages.

Turton et al., "Contralateral and ipsilateral EMG responses to transcranial magnetic stimulation during recovery of arm and hand function after stroke," Electroencephalography and Clinical Neurophysiology 101 pp. 316-328 (1996).

Van Der Lee et al, "The Intra- and Interrater Reliability of the Action Research Arm Test: A Practical Test of Upper Extremity Function in Patients With Stroke," Arch. Phys. Med. Rehabil., vol. 82 pp. 14-19 (Jan. 2001).

Velasco et al. "Absolute and Relative Predictor Values of Some Non-Invasive and Invasive Studies for the Outcome of Anterior Temporal Lobectormy," Science Direct, vol. 31, Issue 1, Jan.-Feb. 2000, pp. 62-74, Elsevier Science, Inc.

Velasco et al., "Electrical Stimulation for Epilepsy: Stimulation of Hippocampal Foci," Stereotactic and Functional Neurosurgery, vol. 77, 2001, pp. 223-227.

Walker-Batson et al., "Amphetamine Paired With Physical Therapy Accelerates Motor Recovery After Stroke," Stroke, vol. 26, No. 12, pp. 2254-2259 (1995).

Waxman et al., "The Interictal Behavior Syndrome of Temporal Lobe Epilepsy," Arch Gen Psychiatry, vol. 32, Dec. 1975, pp. 1580-1586.

Weinand at al., "Cerebral blood flow and temporal lobe epileptogenicity," J Neurosurg, vol. 86, Feb. 1997, pp. 226-232.

Weinand et al., "Cerebral blood flow and temporal lobe epileptogenicity," Neurosurgical Focus, Nov. 1996, vol. 1, No. 5, AANS.ORG, http://www.aans.org/education/journal/neurosurgical/nov96/1-5-3.asp, 17 pages.

Weinand et al., Long-term ictal monitoring with subdural strip electrodes: prognostic factors for selecting temporal lobectomy candidates, J Neurosurg, vol. 77, 1992, pp. 20-28.

Weinand et al., "Surface cortical cerebral blood flow monitoring and single photon emission computed tomography: prognostic factors for selecting temportal lobectormy candidates," Seizure, vol. 3, 1994, pp. 55-59.

Weinand et al., "Targeted Subthreshold Cortical Stimulation for Recovery of Motor Hand Function following Hemiparetic Stroke," Abstract: Apr. 18, 2005 AANS.org, http://www.aans.org/Library/Article.aspx?ArticleId=24934, 2 pages.

Yamamoto et al., "Low-frequency Electric Cortical Stimulation Has an Inhibitory Effect on Epileptic Focus in Mesial Temporal Lobe Epilepsy," Epilepsia, vol. 43, No. 5, 2002, pp. 291-295, Blackwell Publishing, Inc.

Ziemann et al., "Modulation of Plasticity in Human Motor Cortex after Forearm Ischemic Nerve Block," The Journal of Neuroscience 18(3):1115-1123 (Feb. 1998).

U.S. Appl. No. 10/583,630, filed Jun. 20, 2006, Lozano.

U.S. Appl. No. 11/254,060, filed Oct. 19, 2005, Wyler.
U.S. Appl. No. 11/255,187, filed Oct. 19, 2005, Firlik.
U.S. Appl. No. 11/344,453, filed Jan. 30, 2006, Gliner.
U.S. Appl. No. 11/518,139, filed Sep. 7, 2006, Weinand.
U.S. Appl. No. 11/638,326, filed Dec. 12, 2006, Gliner et al.
U.S. Appl. No. 11/697,694, filed Apr. 6, 2007, Fowler.
U.S. Appl. No. 11/697,696, filed Apr. 6, 2007, Pascual-Leone.
U.S. Appl. No. 11/697,703, filed Apr. 6, 2007, Gaw.
Beveridge, J. A., "Use of Exogenous Electric Current in the Treatment of Delayed Lesions in Peripheral Nerves," Plastic and Reconstructive Surgery, Oct. 1988; vol. 82, No. 4, pp. 573-579.
Canavero, S. and Paolotti, R., "Extradural Motor Cortex Stimulation for Advanced Parkinson's Disease: Case Report," Movement Disorders, Jan. 2000; 15(1):169-171.
Cincotta et al., "Reorganization of the motor cortex in a patient with congenital hemiparesis and mirror movements," Neurology, Jul. 12, 2000; 55(1), pp. 129-131.
CNN.com, Health, "Lab Zaps Strokes with Magnetic Pulses," http://www.cnn.com/2004/HEALTH/conditions/11/29/zapping.strokes.ap/, Nov. 29, 2004, 4 pages [Retrieved on Dec. 2, 2004].
Mendonca, A.C., "Directly applied low intensity direct electric current enhances peripheral nerve regeneration in rats," Journal of Neuroscience Methods, Oct. 30, 2003, vol. 129, pp. 183-190.
Politis, M. J., "Mammalian Optic Nerve Regeneration Following the Application of Electric Fields," The Journal of Trauma, Nov. 1988; vol. 28, No. 11, pp. 1548-1552.
Franzini et al., "Reversal of thalamic hand syndrome by long-term motor cortex stimulation," Journal of Neurosurgery, Nov. 2000; 93(5):873-875.
Kimura, K. et al., "Electrically induced neurite outgrowth of PC12 cells on the electrode surface," Med. Biol. Eng. Comput.. Jul. 1998: Abstract Only, 36(4):493-8, http://www.ncbi.nlm.nih.gov/entrez/query.fcgi?db=pubmed&cmd=Retrieve&dopt=Abstract, 1 page.
Liepert at al., "Treatment-Induced Cortical Reorganization After Stroke in Humans," Stroke, Jun. 2000; 31(6):1210-1216.
Martinez et al., "Motor hand recovery after stroke Prognostic yield of early transcranial magnetic stimulation," Electromyogr. Clin. Neurophysiol., Oct.-Dec. 1999: 39(7):405-410.
Nitsche, M.A. and Paulus, W., "Excitability changes induced in the human motor cortex by weak transcranial direct current stimulation," The Journal of Physiology, Sep. 15, 2000; 527(3):633-39.
Oliveri et al., "Paired transcranial magnetic stimulation protocols reveal a pattern of inhibition and facilitation in the human parietal cortex," The Journal of Physiology, Dec. 1, 2000; 529.2, pp. 461-468.
Pascual-Leone at al., "Transcranial magnetic stimulation and neuroplasticity," Neuropsychologia, Feb. 1999; 37(2):207-17.
Price, J. et al., "Neurotransplantation in neurodegenerative disease: a survey of relevant issues in developmental neurobiology," Novartis Foundation Symposium 231, 2000; pp. 148-165, Wiley, Chichester, UK.
Sandkuhler, "Learning and memory in pain pathways." Pain, Nov. 2000; 88(2):113-18, Elsevier/North-Holland.
Sanes, "The Relation between Human Brain Activity and Hand Movements," NeuroImage, May 2000; 11(5), pp. 370-374.
Sanes. J. and Donoghue, J.P., "Plasticity and Primary Motor Cortex," Annual Review of Neuroscience, 2000 (Annual publication); 23:393-415.
Schulz et al., "Localization of Epileptic Auras Induced on Stimulation by Subdural Electrodes," Epilepsia, Dec. 1997; vol. 38, Issue 12, pp. 1321-1329.
Storer et al., "Microiontophoretic application of serotonin (5HT)1B/1D agonists inhibits trigeminal cell firing in the cat," Brain, 1997, vol. 120, Issue 12, pp. 2171-2177, Oxford University Press.
Suzuki et al., "Selective Electrical Stimulation of Postganglionic Cerebrovascular Parasympathetic Nerve Fibers Originating from the Sphenopalatine Ganglion Enhances Cortical Blood Flow in the Rat," Journal of Cerebral Blood Flow and Metabolism, May 1990, 10(3):383-91.
Turton, A. and Lemon, R.N., "The contribution of fast corticospinal input to the voluntary activation of proximal muscles in normal subjects and in stroke patients," Exp. Brain Res., Dec. 1999, 129(4):559-572, Springer Berlin / Heidelberg.
Velasco et al., "Acute and Chronic Electrical Stimulation of the Centromedian Thalamic Nucleus: Modulation of Reticulo-Cortical Systems and Predictor Factors for Generalized Seizure Control," Archives of Medical Research, May-Jun. 2000, 31(3):304-315, Elsevier Science, Inc.
Velasco et al., "Subacute and Chronic Electrical Stimulation of the Hippocampus on Intractable Temporal Lobe Seizures: Preliminary Report," Archives of Medical Research, May-Jun. 2000; 31(3):316-28, Elsevier Science.
Velasco et al., "Subacute Electrical Stimulation of the Hippocampus Blocks Intractable Temporal Lobe Seizures and Paroxysmal EEG Activities," Epilepsia, Feb. 2000, 41(2):158-169, Lippincott Williams & Wilkins, Philadelphia.
Woodbury, D. et al., "Adult Rat and Human Bone Marrow Stromal Cells Differentiate Into Neurons," Journal of Neuroscience Research, Aug. 15, 2000, 61(4):364-70, Wiley Interscience, New York, NY.
Cincinelli et al., "Transcranial magnetic stimulation reaveals an interhemispheric asymmetry of cortical inhibition in focal epilepsy," Neurophysiology, vol. 11, No. 4 Mar. 20, 2000, pp. 701-707.
Bhatnagar, et al., "Effects of intralaminar thalamic stimulation on language functions," Brain and Language, vol. 92, May 2, 2004, p. 1-11, Elsevier, Inc.
Devinsky et al., "Electroencephalographic studies of simple partial seizures with subdural electrode recordings," Neurology, 39, Apr. 1989, pp. 527-533.
Devinsky et al., "Clinical and electroencephalographic features of simple partial seizures," Neurology, 38, Sep. 1988, pp. 1347-1352.
Canavero, S. an Paolotti, R., "Extradural Motor Cortex Stimulation for Advanced Parkinson's Disease Cast Report," Movement Disorders, 15(1), 169-171, Jan. 2000.
Cincotta et al., "Reorganization of the motor cortex in a patient with congenital hemiparesis and mirror movements," Neurology: vol. 55, pp. 139-131, Jul. 2000.
Cincotta et al., "Suprathreshold 0.3Hz repetitive RMS Prolongs the cortical silent period: potential implications for therapeutic trails in epilepsy," Clinical Neurophysiology, vol. 114, pp. 1827-1833, Oct. 2003, Elsevier Ireland Ltd.

* cited by examiner

METHODS AND APPARATUS FOR EFFECTUATING A LASTING CHANGE IN A NEURAL-FUNCTION OF A PATIENT

CROSS-REFERENCE TO RELATED APPLICATION(S)

This application claims the benefit of U.S. Application No. 60/325,872 filed on Sep. 28, 2001, and is a continuation-in-part of U.S. application Ser. No. 09/802,808, filed on Mar. 8, 2001 now U.S. Pat. No. 7,010,351, which claims the benefit of U.S. Provisional Application No. 60/217,981, filed Jul. 13, 2000; both of which are incorporated by reference herein in their entirety.

TECHNICAL FIELD

Several embodiments of methods and apparatus in accordance with the invention are related to electrically stimulating a region in the cortex or other area of the brain to bring about a lasting change in a physiological function and/or a mental process of a patient.

BACKGROUND

A wide variety of mental and physical processes are known to be controlled or are influenced by neural activity in particular regions of the brain. In some areas of the brain, such as in the sensory or motor cortices, the organization of the brain resembles a map of the human body; this is referred to as the "somatotopic organization of the brain." There are several other areas of the brain that appear to have distinct functions that are located in specific regions of the brain in most individuals. For example, areas of the occipital lobes relate to vision, regions of the left inferior frontal lobes relate to language in the majority of people, and regions of the cerebral cortex appear to be consistently involved with conscious awareness, memory, and intellect. This type of location-specific functional organization of the brain, in which discrete locations of the brain are functional organization of the brain, in which discrete locations of the brain are statistically likely to control particular mental or physical functions in normal individuals, is herein referred to as the "functional organization of the brain."

Many problems or abnormalities with body functions can be caused by damage, disease and/or disorders of the brain. A stroke, for example, is one very common condition that damages the brain. Strokes are generally caused by emboli (e.g., obstruction of a vessel), hemorrhages (e.g., rupture of a vessel), or thrombi (e.g., clotting) in the vascular system of a specific region of the cortex, which in turn generally causes a loss or impairment of a neural function (e.g., neural functions related to face muscles, limbs, speech, etc.). Stroke patients are typically treated using physical therapy to rehabilitate the loss of function of a limb or another affected body part. For most patients, little can be done to improve the function of the affected limb beyond the recovery that occurs naturally without intervention. One existing physical therapy technique for treating stroke patients constrains or restrains the use of a working body part of the patient to force the patient to use the affected body part. For example, the loss of use of a limb is treated by restraining the other limb. Although this type of physical therapy has shown some experimental efficacy, it is expensive, time-consuming and little-used. Stroke patients can also be treated using physical therapy plus adjunctive therapies. For example, some types of drugs, such as amphetamines, that increase the activation of neurons in general, appear to enhance neural networks; these drugs, however, have limited efficacy because they are very non-selective in their mechanisms of action and cannot be delivered in high concentrations directly at the site where they are needed. Therefore, there is a need to develop effective treatments for rehabilitating stroke patients and patients that have other types of brain damage.

Other brain disorders and diseases are also difficult to treat. Alzheimer's disease, for example, is known to affect portions of the cortex, but the cause of Alzheimer's disease and how it alters the neural activity in the cortex is not fully understood. Similarly, the neural activity of brain disorders (e.g., depression and obsessive-compulsive behavior) is also not fully understood. Therefore, there is also a need to develop more effective treatments for other brain disorders and diseases.

The neural activity in the brain can be influenced by electrical energy that is supplied from an external source outside of the body. Various neural functions can thus be promoted or disrupted by applying an electrical current to the cortex or other region of the brain. As a result, the quest for treating damage, disease and disorders in the brain have led to research directed toward using electricity or magnetism to control brain functions.

One type of treatment is transcranial electrical stimulation (TES), which involves placing an electrode on the exterior of the scalp and delivering an electrical current to the brain through the scalp and skull. Patents directed to TES include: U.S. Pat. No. 5,540,736 issued to Haimovich et al. (for providing analgesia); U.S. Pat. No. 4,140,133 issued to Katrubin et al. (for providing anesthesia); U.S. Pat. No. 4,646,744 issued to Capel (for treating drug addiction, appetite disorders, stress, insomnia and pain); and U.S. Pat. No. 4,844,075 issued to Liss et al. (for treating pain and motor dysfunction associated with cerebral palsy). TES, however, is not widely used because the patients experience a great amount of pain and the electrical field is difficult to direct or focus accurately.

Another type of treatment is transcranial magnetic stimulation (TMS), which involves producing a high-powered magnetic field adjacent to the exterior of the scalp over an area of the cortex. TMS does not cause the painful side effects of TES. Since 1985, TMS has been used primarily for research purposes in brain-mapping endeavors. Recently, however, potential therapeutic applications have been proposed primarily for the treatment of depression. A small number of clinical trials have found TMS to be effective in treating depression when used to stimulate the left prefrontal cortex.

The TMS treatment of a few other patient groups have been studied with promising results, such as patients with Parkinson's disease and hereditary spinocerebellar degeneration. Patents and published patent applications directed to TMS include: published international patent application WO 98/06342 (describing a transcranial magnetic stimulator and its use in brain mapping studies and in treating depression); U.S. Pat. No. 5,885,976 issued to Sandyk (describing the use of transcranial magnetic stimulation to treat a variety of disorders allegedly related to deficient serotonin neurotransmission and impaired pineal melatonin functions); and U.S. Pat. No. 5,092,835 issued to Schurig et al. (describing the treatment of neurological disorders (such as autism), treatment of learning disabilities, and augmentation of mental and physical abilities of "normal" people by a combination of transcranial magnetic stimulation and peripheral electrical stimulation).

Independent studies have also demonstrated that TMS is able to produce a lasting change in neural activity within the cortex that occurs for a period of time after terminating the TMS treatment ("neuroplasticity"). For example, Ziemann et al., *Modulation of Plasticity in Human Motor Cortex after Forearm Ischemic Nerve Block*, 18 J Neuroscience 1115

(February 1998), disclose that TMS at subthreshold levels (e.g., levels at which movement was not induced) in neuro-block models that mimic amputation was able to modify the lasting changes in neural activity that normally accompany amputation. Similarly, Pascual-Leone et al. (submitted for publication) disclose that applying TMS over the contralateral motor cortex in normal subjects who underwent immobilization of a hand in a cast for 5 days can prevent the decreased motor cortex excitability normally associated with immobilization. Other researchers have proposed that the ability of TMS to produce desired changes in the cortex may someday be harnessed to enhance neuro-rehabilitation after a brain injury, such as stroke, but there are no published studies to date.

Other publications related to TMS include Cohen et al., *Studies of Neuroplasticity With Transcranial Magnetic Stimulation*, 15 J. Clin. Neurophysiol. 305 (1998); Pascual-Leone et al., *Transcranial Magnetic Stimulation and Neuroplasticity*, 37 Neuropsychologia 207 (1999); Stefan et al., *Induction of Plasticity in the Human Motor Cortex by Paired Associative Stimulation*, 123 Brain 572 (2000); Sievner et al., *Lasting Cortical Activation after repetitive TMS of the Motor Cortex*, 54 Neurology 956 (February 2000); Pascual-Leone et al., *Study and Modulation of Human Cortical Excitability With Transcranial Magnetic Stimulation*, 15 J. Clin. Neurophysiol. 333 (1998); and Boylan et al., *Magnetoelectric Brain Stimulation in the Assessment Of Brain Physiology And Pathophysiology*, 111 Clin. Neurophysiology 504 (2000).

Although TMS appears to be able to produce a change in the underlying cortex beyond the time of actual stimulation, TMS is not presently effective for treating many patients because the existing delivery systems are not practical for applying stimulation over an adequate period of time. TMS systems, for example, are relatively complex and require stimulation treatments to be performed by a healthcare professional in a hospital or physician's office. TMS systems also may not be reliable for longer-term therapies because it is difficult to (a) accurately localize the region of stimulation in a reproducible manner, (b) hold the device in the correct position over the cranium for a long period, especially when a patient moves or during rehabilitation, and (c) provide stimulation for extended periods of time (e.g., more than several seconds). Furthermore, current TMS systems generally do not sufficiently focus the electromagnetic energy on the desired region of the cortex for many applications. As such, the potential therapeutic benefit of TMS using existing equipment is relatively limited.

Direct and indirect electrical stimulation of the central nervous system has also been proposed to treat a variety of disorders and conditions. For example, U.S. Pat. No. 5,938,688 issued to Schiff notes that the phenomenon of neuroplasticity may be harnessed and enhanced to treat cognitive disorders related to brain injuries caused by trauma or stroke. Schiff's implant is designed to increase the level of arousal of a comatose patient by stimulating deep brain centers involved in consciousness. To do this, Schiff's invention involves electrically stimulating at least a portion of the patient's intralaminar nuclei (i.e., the deep brain) using, e.g., an implantable multipolar electrode and either an implantable pulse generator or an external radiofrequency controlled pulse generator. Schiff's deep brain implant is highly invasive, however, and could involve serious complications for the patient.

Likewise, U.S. Pat. No. 6,066,163 issued to John acknowledges the ability of the brain to overcome some of the results of an injury through neuroplasticity. John also cites a series of articles as evidence that direct electrical stimulation of the brain can reverse the effects of a traumatic injury or stroke on the level of consciousness. The system disclosed in John stimulates the patient and modifies the parameters of stimulation based upon the outcome of comparing the patient's present state with a reference state in an effort to optimize the results. Like Schiff, however, the invention disclosed in John is directed to a highly invasive deep brain stimulation system.

Another device for stimulating a region of the brain is disclosed by King in U.S. Pat. No. 5,713,922. King discloses a device for cortical surface stimulation having electrodes mounted on a paddle implanted under the skull of the patient. The electrodes are implanted on the surface of the brain in a fixed position. The electrodes in King accordingly cannot move to accommodate changes in the shape of the brain. King also discloses that the electrical pulses are generated by a pulse generator that is implanted in the patient remotely from the cranium (e.g., subclavicular implantation). The pulse generator is not directly connected to the electrodes, but rather it is electrically coupled to the electrodes by a cable that extends from the remotely implanted pulse generator to the electrodes implanted in the cranium. The cable disclosed in King extends from the paddle, around the skull, and down the neck to the subclavicular location of the pulse generator.

King discloses implanting the electrodes in contact with the surface of the cortex to create paresthesia, which is a sensation of vibration or "buzzing" in a patient. More specifically, King discloses inducing paresthesia in large areas by applying electrical stimulation to a higher element of the central nervous system (e.g., the cortex). As such, King discloses placing the electrodes against particular regions of the brain to induce the desired paresthesia. The purpose of creating paresthesia over a body region is to create a distracting stimulus that effectively reduces perception of pain in the body region. Thus, King appears to require stimulation above activation levels.

Although King discloses a device that stimulates a region on the cortical surface, this device is expected to have several drawbacks. First, it is expensive and time-consuming to implant the pulse generator and the cable in the patient. Second, it appears that the electrodes are held at a fixed elevation that does not compensate for anatomical changes in the shape of the brain relative to the skull, which makes it difficult to accurately apply an electrical stimulation to a desired target site of the cortex in a focused, specific manner. Third, King discloses directly activating the neurons to cause paresthesia, which is not expected to cause entrainment of the activity in the stimulated population of neurons with other forms of therapy or adaptive behavior, such as physical or occupational therapy. Thus, King is expected to have several drawbacks.

King and the other foregoing references are also expected to have drawbacks in producing the desired neural activity because these references generally apply the therapy to the region of the brain that is responsible for the physiological function or mental process according to the functional organization of the brain. In the case of a brain injury or disease, however, the region of the brain associated with the affected physiological function or cognitive process may not respond to stimulation therapies. Thus, existing techniques may not produce adequate results that last beyond the stimulation period.

DETAILED DESCRIPTION

Figure 1A:
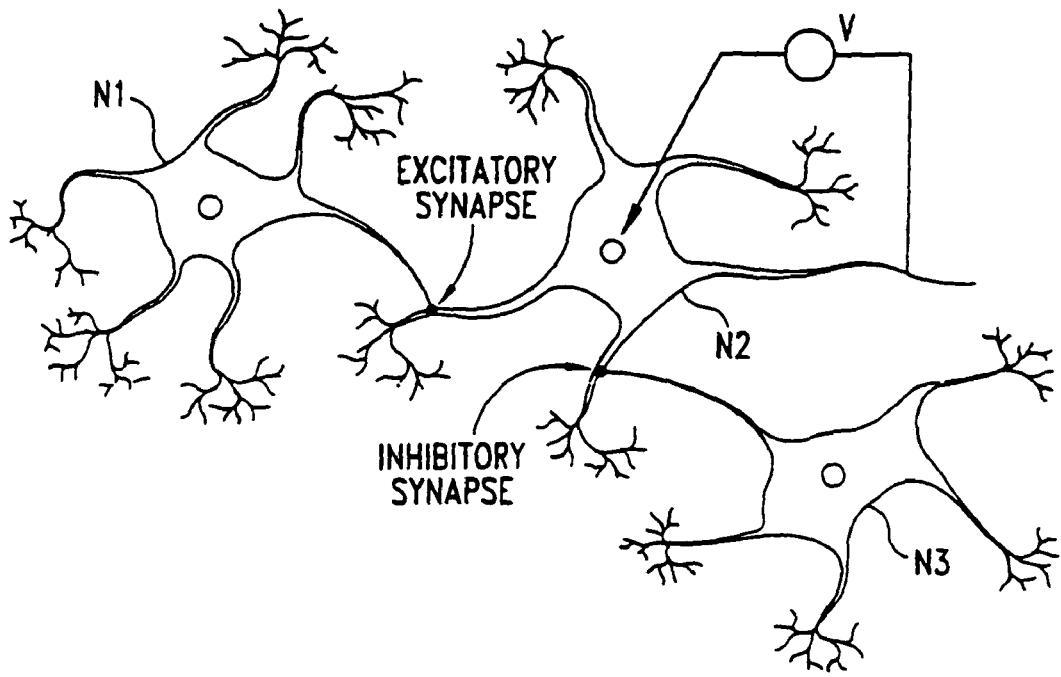
FIG. 1A is a schematic view of neurons.

The following disclosure describes several methods and apparatus for intracranial electrical stimulation to treat or otherwise effectuate a change in neural-functions of a patient. Several embodiments of methods in accordance with the invention are directed toward enhancing or otherwise inducing neuroplasticity to effectuate a particular neural-function. Neuroplasticity refers to the ability of the brain to change or adapt over time. It was once thought adult brains became relatively "hard wired" such that functionally significant neural networks could not change significantly over time or in response to injury. It has become increasingly more apparent that these neural networks can change and adapt over time so that meaningful function can be regained in response to brain injury. An aspect of several embodiments of methods in accordance with the invention is to provide the appropriate triggers for adaptive neuroplasticity. These appropriate triggers appear to cause or enable increased synchrony of functionally significant populations of neurons in a network.

Electrically enhanced or induced neural stimulation in accordance with several embodiments of the invention excites a portion of a neural network involved in a functionally significant task such that a selected population of neurons can become more strongly associated with that network. Because such a network will subserve a functionally meaningful task, such as motor relearning, the changes are more likely to be lasting because they are continually being reinforced by natural use mechanisms. The nature of stimulation in accordance with several embodiments of the invention ensures that the stimulated population of neurons links to other neurons in the functional network. It is expected that this occurs because action potentials are not actually caused by the stimulation, but rather are caused by interactions with other neurons in the network. Several aspects of the electrical stimulation in accordance with selected embodiments of the invention simply allows this to happen with an increased probability when the network is activated by favorable activities, such as rehabilitation or limb use.

The methods in accordance with the invention can be used to treat brain damage (e.g., stroke, trauma, etc.), brain disease (e.g., Alzheimer's, Pick's, Parkinson's, etc.), and/or brain disorders (e.g., epilepsy, depression, etc.). The methods in accordance with the invention can also be used to enhance functions of normal, healthy brains (e.g., learning, memory, etc.), or to control sensory functions (e.g., pain).

Certain embodiments of methods in accordance with the invention electrically stimulate the brain at a stimulation site where neuroplasticity is occurring. The stimulation site may be different than the region in the brain where neural activity is typically present to perform the particular function according to the functional organization of the brain. In one embodiment in which neuroplasticity related to the neural-function occurs in the brain, the method can include identifying the location where such neuroplasticity is present. This particular procedure may accordingly enhance a change in the neural activity to assist the brain in performing the particular neural function. In an alternative embodiment in which neuroplasticity is not occurring in the brain, an aspect is to induce neuroplasticity at a stimulation site where it is expected to occur. This particular procedure may thus induce a change in the neural activity to instigate performance of the neural function. Several embodiments of these methods are expected to produce a lasting effect on the intended neural activity at the stimulation site.

The specific details of certain embodiments of the invention are set forth in the following description and in FIGS. 1A-40 to provide a thorough understanding of these embodiments to a person of ordinary skill in the art. More specifically, several embodiments of methods in accordance with the invention are initially described with reference to FIGS. 1-5C, and then several embodiments of devices for stimulating the cortical and/or deep-brain regions of the brain are described with reference to FIGS. 6-40. A person skilled in the art will understand that the present invention may have additional embodiments, or that the invention can be practiced without several of the details described below.

A. Methods for Electrically Stimulating Regions of the Brain

1. Embodiments of Electrically Enhancing Neural Activity

Figure 1B:
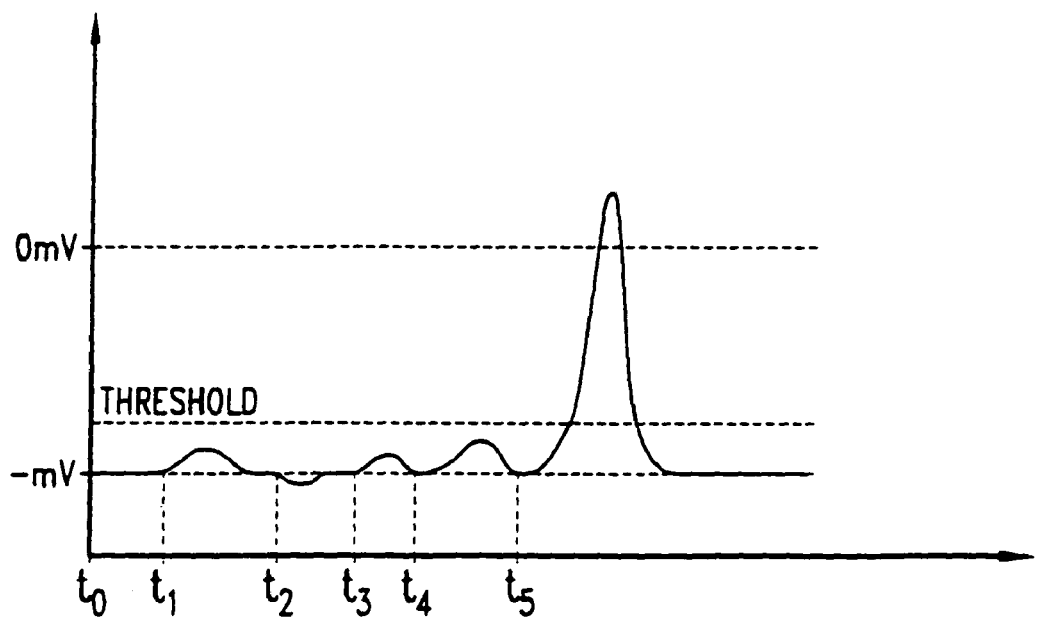
FIG. 1B is a graph illustrating firing an "action potential" associated with normal neural activity.

FIG. 1A is a schematic representation of several neurons N1-N3 and FIG. 1B is a graph illustrating an "action potential" related to neural activity in a normal neuron. Neural activity is governed by electrical impulses generated in neurons. For example, neuron N1 can send excitatory inputs to neuron N2 (e.g., times $t_1$, $t_3$ and $t_4$ in FIG. 1B), and neuron N3 can send inhibitory inputs to neuron N2 (e.g., time $t_2$ in FIG. 1B). The neurons receive/send excitatory and inhibitory inputs from/to a population of other neurons. The excitatory and inhibitory inputs can produce "action potentials" in the neurons, which are electrical pulses that travel through neurons by changing the flux of sodium (Na) and potassium (K) ions across the cell membrane. An action potential occurs when the resting membrane potential of the neuron surpasses a threshold level. When this threshold level is reached, an "all-or-nothing" action potential is generated. For example, as shown in FIG. 1B, the excitatory input at time $t_5$ causes neuron N2 to "fire" an action potential because the input exceeds the threshold level for generating the action potential. The action potentials propagate down the length of the axon (the long process of the neuron that makes up nerves or neuronal tracts) to cause the release of neurotransmitters from that neuron that will further influence adjacent neurons.

Figure 1C:
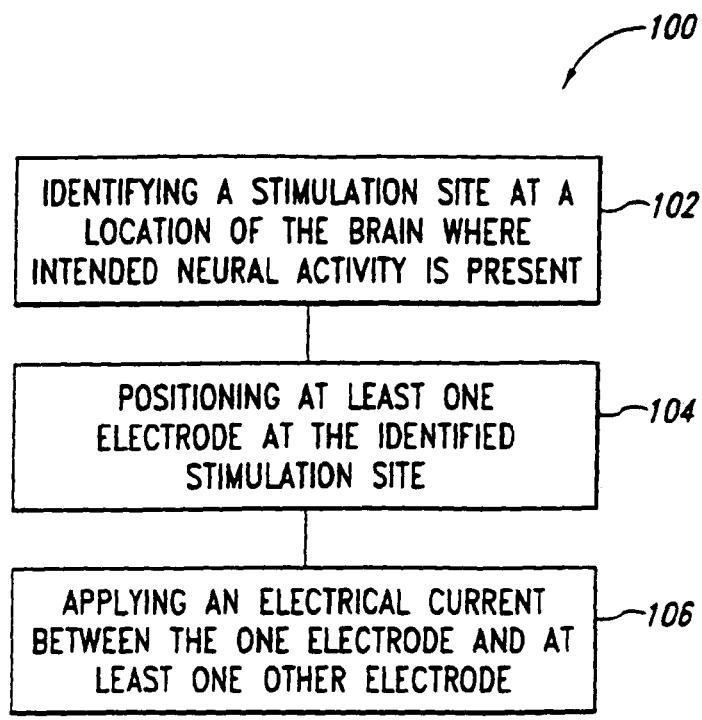
FIG. 1C is a flowchart of a method for effectuating a neural-function of a patient associated with a location in the brain in accordance with one embodiment of the invention.

FIG. 1C is a flowchart illustrating a method 100 for effectuating a neural-function in a patient in accordance with an embodiment of the invention. The neural-function, for example, can control a specific mental process or physiological function, such as a particular motor function or sensory function (e.g., movement of a limb) that is normally associated with neural activity at a "normal" location in the brain according to the functional organization of the brain. In several embodiments of the method 100, at least some neural activity related to the neural-function can be occurring at a site in the brain. The site of the neural activity may be at the normal location where neural activity typically occurs to carry out the neural-function according to the functional organization of the brain, or the site of the neural activity may be at a different location where the brain has recruited material to perform the neural activity. In either situation, one aspect of several embodiments of the method 100 is to determine the location in the brain where this neural activity is present.

The method 100 includes a diagnostic procedure 102 involving identifying a stimulation site at a location of the brain where an intended neural activity related to the neural-function is present. In one embodiment, the diagnostic procedure 102 includes generating the intended neural activity in the brain from a "peripheral" location that is remote from the normal location, and then determining where the intended neural activity is actually present in the brain. In an alternative embodiment, the diagnostic procedure 102 can be performed by identifying a stimulation site where neural activity has changed in response to a change in the neural-function. The method 100 continues with an implanting procedure 104 involving positioning first and second electrodes at the identified stimulation site, and a stimulating procedure 106 involving applying an electrical current between the first and second electrodes. Many embodiments of the implanting procedure 104 position two or more electrodes at the stimulation site, but other embodiments of the implanting procedure involve positioning only one electrode at the stimulation site and another electrode remotely from the stimulation site. As such, the implanting procedure 104 of the method 100 can include implanting at least one electrode at the stimulation site. The procedures 102-106 are described in greater detail below.

Figure 2:
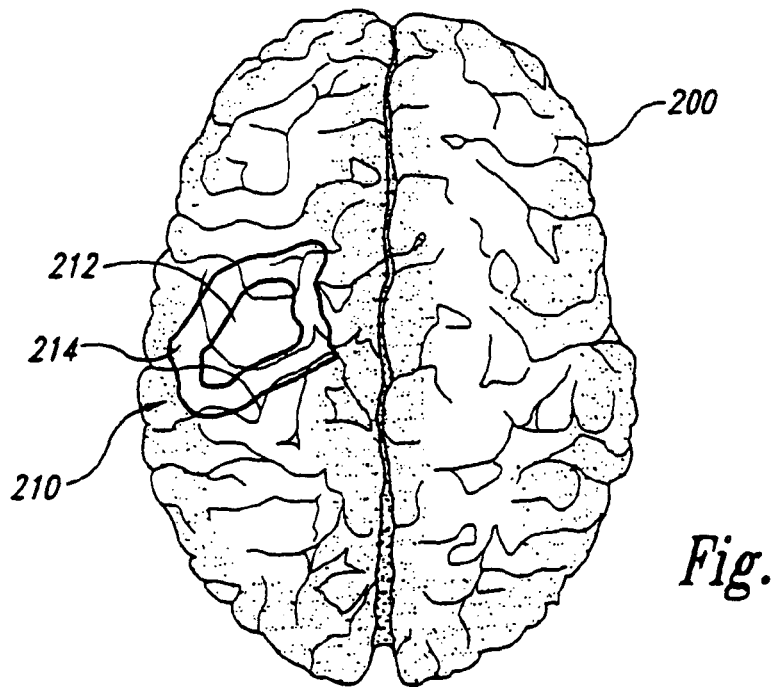
FIG. 2 is a top plan view of a portion of a brain illustrating neural activity in a first region of the brain associated with the neural-function of the patient according to the somatotopic organization of the brain.
Figure 3:
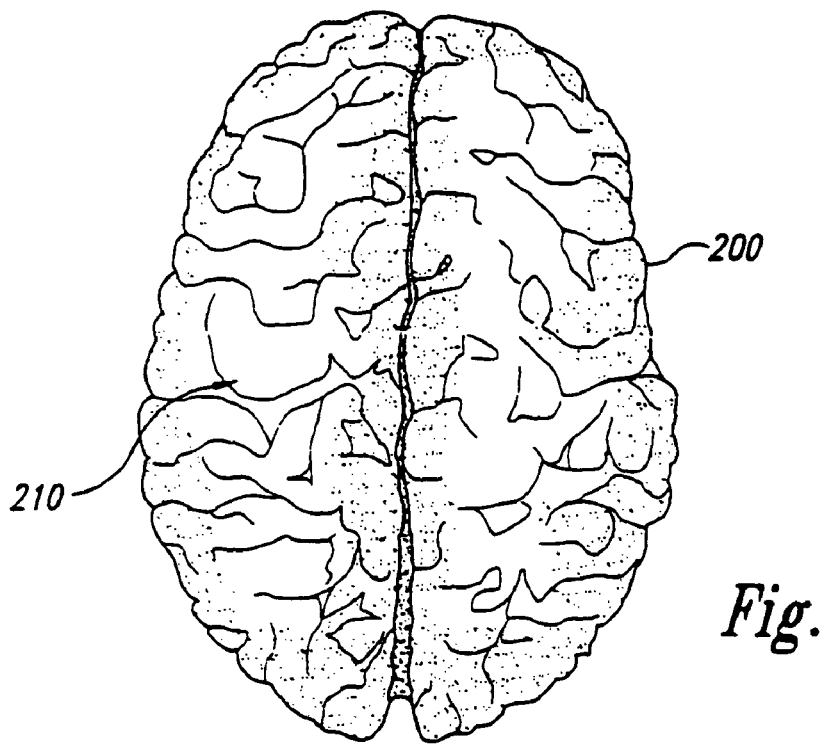
FIG. 3 is a top plan image of a portion of the brain illustrating a loss of neural activity associated with the neural-function of the patient used in one stage of a method in accordance with an embodiment of the invention.
Figure 4:
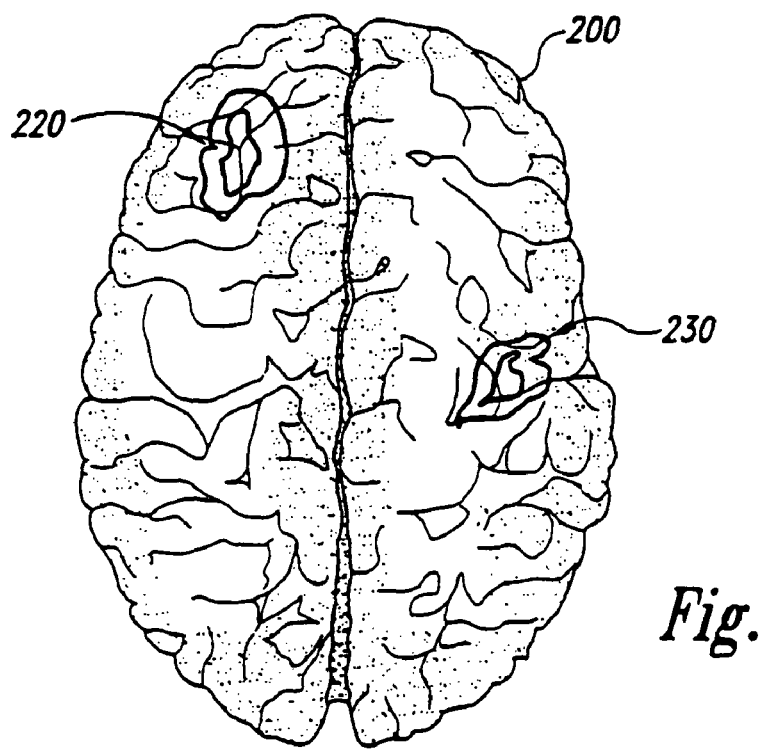
FIG. 4 is a top plan image of the brain of FIG. 3 showing a change in location of the neural activity associated with the neural-function of the patient at another stage of a method in accordance with an embodiment of the invention.

FIGS. 2-4 illustrate an embodiment of the diagnostic procedure 102. The diagnostic procedure 102 can be used to determine the region of the brain where stimulation will likely effectuate the desired function, such as rehabilitating a loss of a neural-function caused by a stroke, trauma, disease or other circumstance. FIG. 2, more specifically, is an image of a normal, healthy brain 200 having a first region 210 where the intended neural activity occurs to effectuate a specific neural-function in accordance with the functional organization of the brain. For example, the neural activity in the first region 210 shown in FIG. 2 is generally associated with the movement of a patient's fingers. The first region 210 can have a high-intensity area 212 and a low-intensity area 214 in which different levels of neural activity occur. It is not necessary to obtain an image of the neural activity in the first region 210 shown in FIG. 2 to carry out the diagnostic procedure 102, but rather it is provided to show an example of neural activity that typically occurs at a "normal location" according to the functional organization of the brain 200 for a large percentage of people with normal brain function. It will be appreciated that the actual location of the first region 210 will generally vary between individual patients.

The neural activity in the first region 210, however, can be impaired. In a typical application, the diagnostic procedure 102 begins by taking an image of the brain 200 that is capable of detecting neural activity to determine whether the intended neural activity associated with the particular neural function of interest is occurring at the region of the brain 200 where it normally occurs according to the functional organization of the brain. FIG. 3 is an image of the brain 200 after the first region 210 has been affected (e.g., from a stroke, trauma or other cause). As shown in FIG. 3, the neural activity that controlled the neural-function for moving the fingers no longer occurs in the first region 210. The first region 210 is thus "inactive," which is expected to result in a corresponding loss of the movement and/or sensation in the fingers. In some instances, the damage to the brain 200 may result in only a partial loss of the neural activity in the damaged region. In either case, the image shown in FIG. 3 establishes that the loss of the neural-function is related to the diminished neural activity in the first region 210. The brain 200 may accordingly recruit other neurons to perform neural activity for the affected neural-function (i.e., neuroplasticity), or the neural activity may not be present at any location in the brain.

FIG. 4 is an image of the brain 200 illustrating a plurality of potential stimulation sites 220 and 230 for effectuating the neural-function that was originally performed in the first region 210 shown in FIG. 2. FIGS. 3 and 4 show an example of neuroplasticity in which the brain compensates for a loss of neural-function in one region of the brain by recruiting other regions of the brain to perform neural activity for carrying out the affected neural-function. The diagnostic procedure 102 utilizes the neuroplasticity that occurs in the brain to identify the location of a stimulation site that is expected to be more responsive to the results of an electrical, magnetic, sonic, genetic, biologic, and/or pharmaceutical procedure to effectuate the desired neural-function.

One embodiment of the diagnostic procedure 102 involves generating the intended neural activity remotely from the first region 210 of the brain, and then detecting or sensing the location in the brain where the intended neural activity has been generated. The intended neural activity can be generated by applying an input that causes a signal to be sent to the brain. For example, in the case of a patient that has lost the use of a limb, the affected limb is moved and/or stimulated while the brain is scanned using a known imaging technique that can detect neural activity (e.g., functional MRI, positron emission tomography, etc.). In one specific embodiment, the affected limb can be moved by a practitioner or the patient, stimulated by sensory tests (e.g., pricking), or subject to peripheral electrical stimulation. The movement/stimulation of the affected limb produces a peripheral neural signal from the limb that is expected to generate a response neural activity in the brain. The location in the brain where this response neural activity is present can be identified using the imaging technique. FIG. 4, for example, can be created by moving the affected fingers and then noting where neural activity occurs in response to the peripheral stimulus. By peripherally generating the intended neural activity, this embodiment may accurately identify where the brain has recruited matter (i.e., sites 220 and 230) to perform the intended neural activity associated with the neural-function.

Several particular embodiments for peripherally generating the intended neural activity are expected to be useful for therapies that involve patients who have lost volitional control of a body part. Volitional movement of a body part involves several parts of the cortex. For example, the prefrontal cortex is where the decision to move the body part occurs, the pre-motor cortex then generates the particular instructions for performing the movement, and the motor cortex then uses these instructions to send the appropriate electrical pulses to the body part via the spinal cord. The loss of volitional movement of a body part is usually caused by damage to the motor cortex. The following embodiments for generating the intended neural activity locate the site on the cortex where the brain is recruiting neurons related to the functionality of the impaired body part even though the patient is incapable of moving it.

Figure 4A:
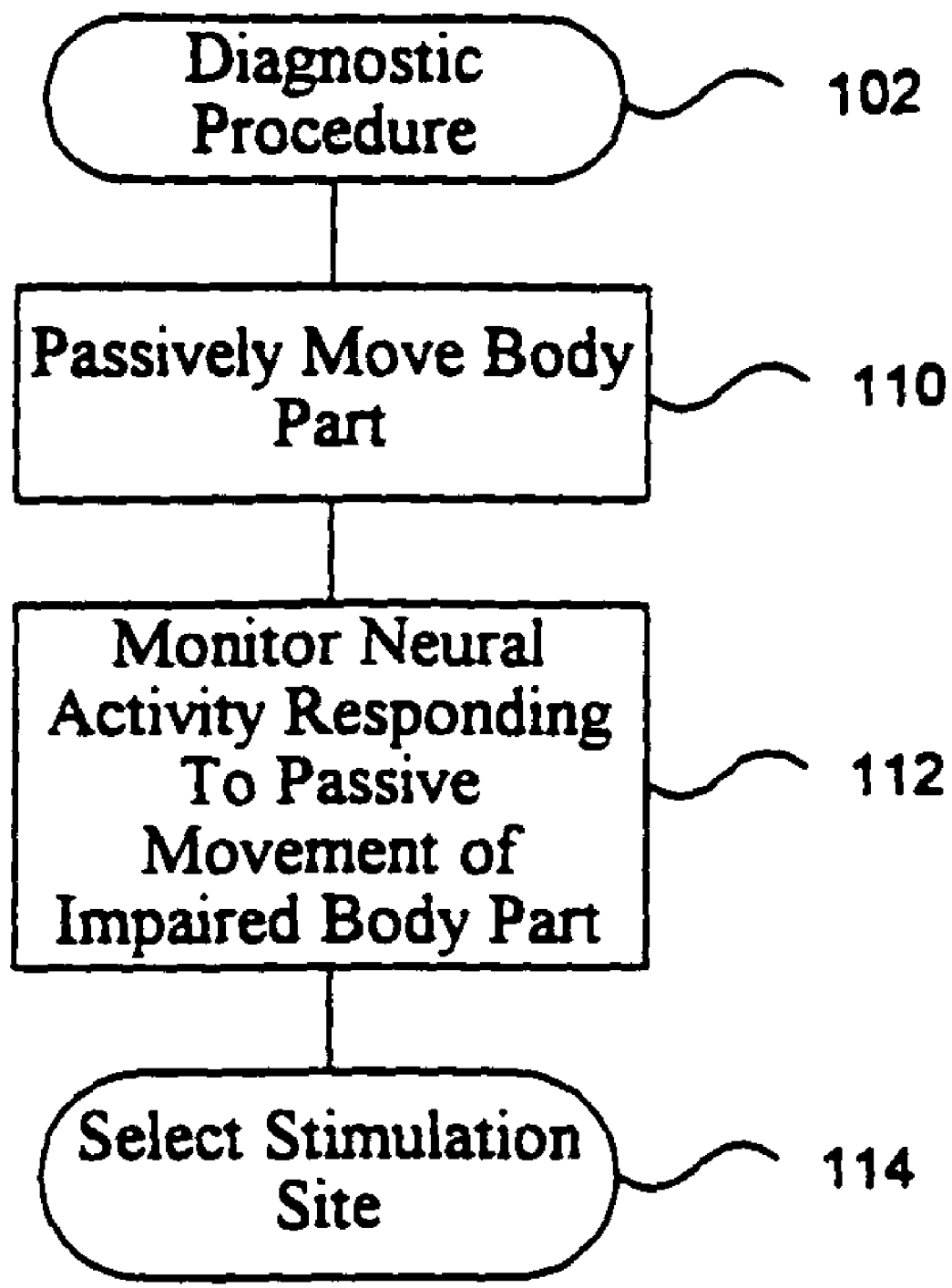
FIGS. 4A-4C are flow charts illustrating various embodiments of diagnostic procedures used in embodiments of methods in accordance with the invention.

FIG. 4A is a flow chart of one embodiment of the diagnostic procedure 102 (FIG. 1C) in which the intended neural activity is generated peripherally. This embodiment includes a generating phase 110 involving passively moving the impaired body part. A clinician, for example, can move the impaired body part or massage the muscles associated with the impaired body part. In an alternate embodiment, a mechanical device moves the impaired body part, such as physical therapy equipment that continually and/or intermittently moves limbs, digits and other body parts. The diagnostic procedure 102 also includes a monitoring phase 112 involving detecting the location in the cortex where passive movement of the impaired limb generates neural activity. The monitoring phase 112 is typically performed before, during, and after the generating phase 110. In one particular embodiment, the monitoring phase 110 involves: (a) imaging the neural activity in the brain using functional MRI before passively moving the impaired body part to provide a baseline indication of brain activity; (b) passively moving the impaired body part in the generating phase 110 while imaging the brain; and (c) determining the site where neural activity occurs in response to the passive movement of the impaired body part.

The passive movement of the impaired body part is expected to provide a good indication of the location in the cortex where the brain is performing neural activity that controls the impaired body part. Passively moving the impaired body part produces neural signals that travel through the spinal cord to the cortex. The neural signals then produce neural activity at a site in the brain that is associated with the function of the impaired body part; it is this neural activity that defines the "intended neural activity." The site of the intended neural activity generated by the passive movement of the impaired body part correlates well with active movement of the impaired body part. Thus, by passively moving an impaired body part and monitoring the intended neural activity that occurs in response to the passive motion, the location of the intended neural activity defines the stimulation site for applying an electrical therapy or another type of therapy.

Figure 4B:
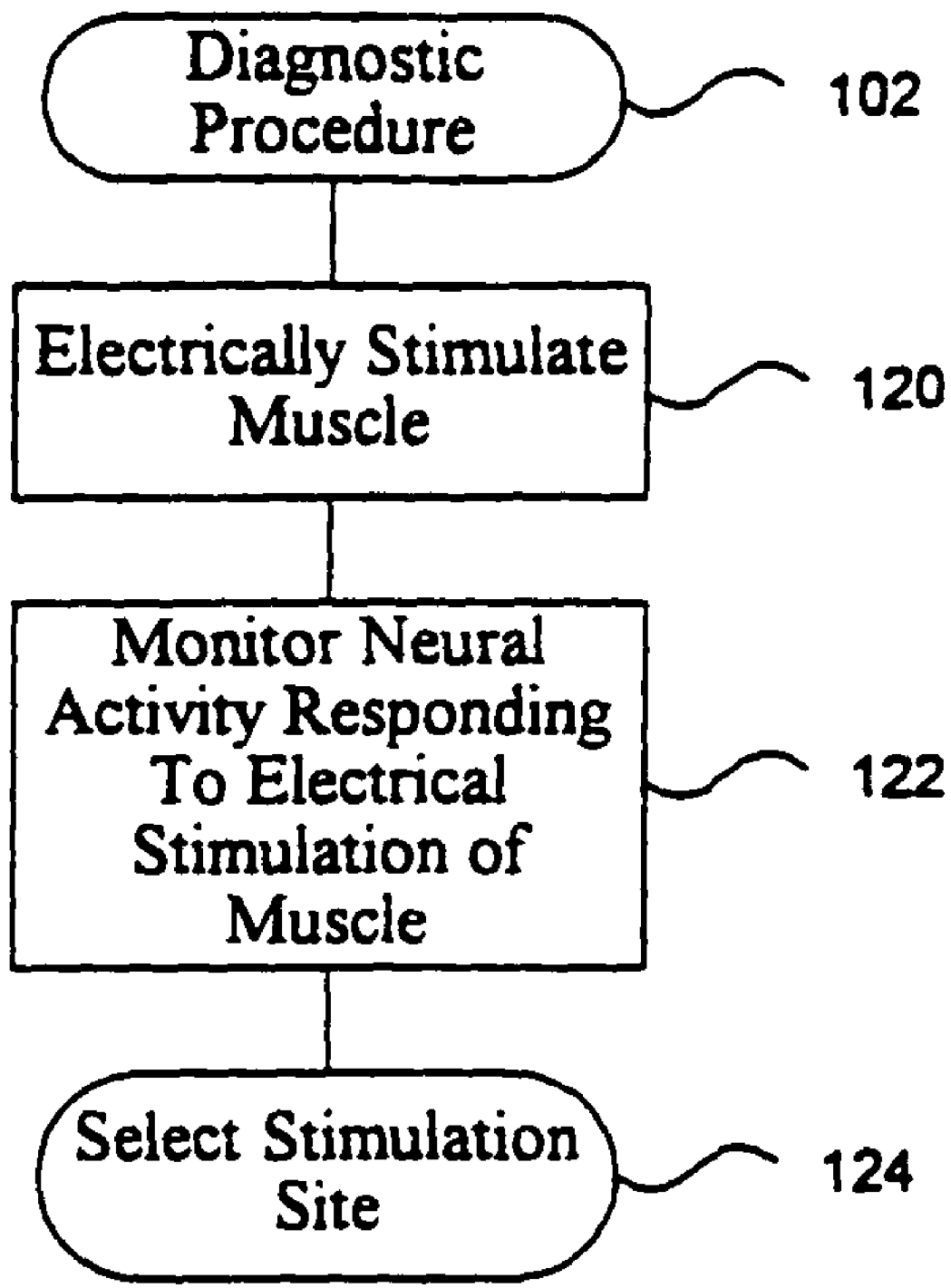

FIG. 4B is a flow chart of another embodiment of the diagnostic procedure 102. In this embodiment, the diagnostic procedure 102 includes a generating phase 120 involving electrically stimulating the muscles of the impaired body part. The electrical stimulation can be performed using transcutaneous or subcutaneous electrical stimulation devices. A transcutaneous device, for example, can include electrode patches that are applied to the skin and coupled to a current source. Suitable subcutaneous devices can include percutaneous therapy electrodes and system developed by Vertis Neuroscience, Inc. of Seattle, Wash., and described in U.S. application Ser. Nos. 09/666,931 and 09/452,477, which are all herein incorporated by reference. The percutaneous electrode devices can be flexible, wire-type electrodes or rigid, needle-type electrodes. The wire-type electrodes may be more suitable for use in the generating phase 120 of the diagnostic procedure 102 because they can flex as the muscles contract/extend with the peripheral electrical stimulation. The embodiment of the diagnostic procedure 102 also includes a monitoring phase 122 in which the neural activity in the brain is monitored while performing the generating phase 120. The monitoring phase 122 can be similar to the monitoring phase 112 described above. Thus, the monitoring phase 122 determines the site where cortical neural activity occurs in response to the electrical stimulation of the muscles.

The embodiment of the diagnostic procedure 102 shown in FIG. 4B that electrically stimulates the impaired muscles is expected to provide highly accurate results. One reason for this is that the electrical current can be applied to only certain muscles without having to involve other muscles. As a result, it is expected that there will be less "noise" in the image of the neural activity. Such a reduction in noise will accordingly likely produce a more accurate indication of where the intended neural activity is occurring in the brain.

Figure 4C:
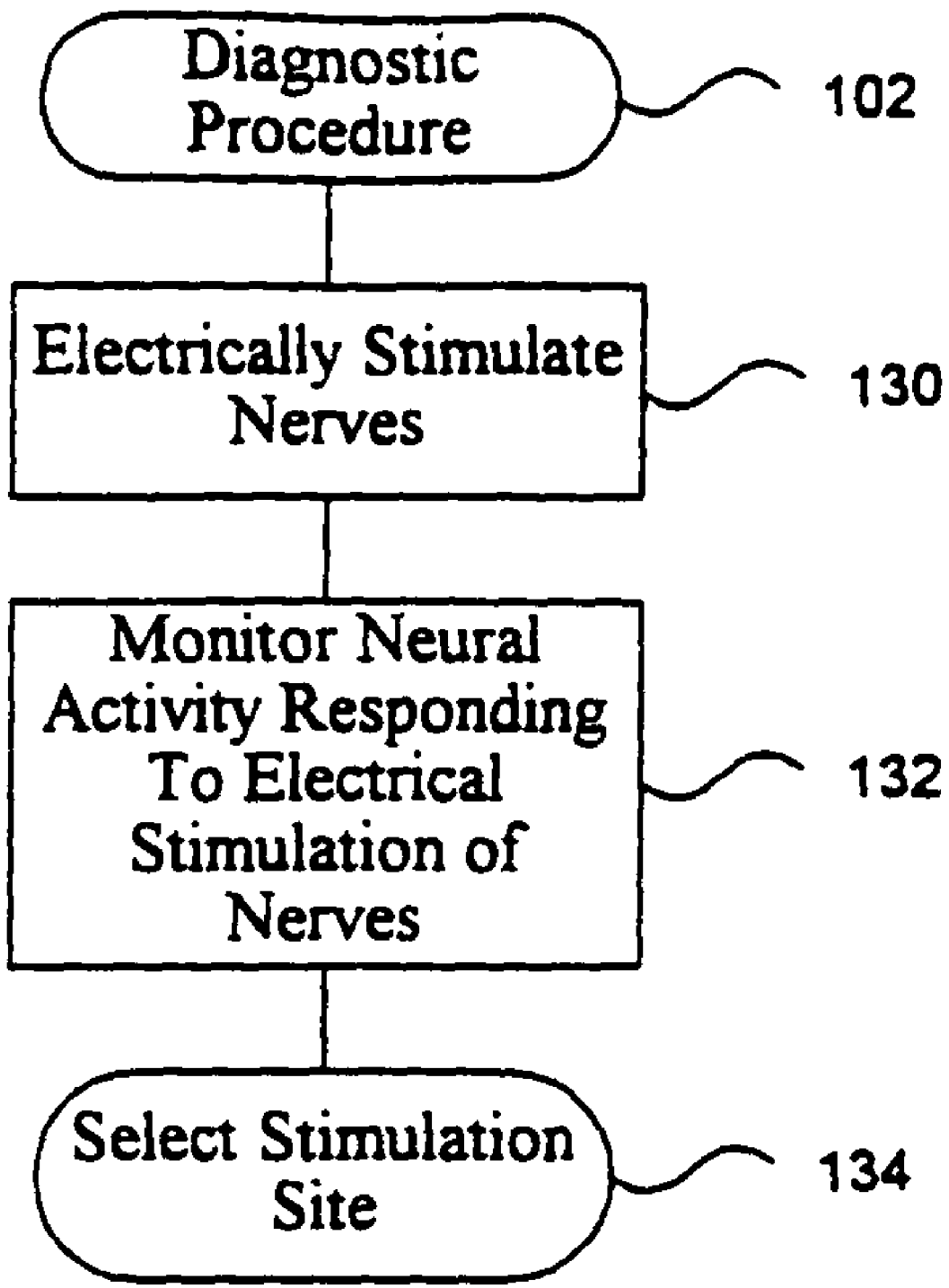

FIG. 4C is a flow diagram of yet another embodiment of the diagnostic procedure 102. In this embodiment, the diagnostic procedure 102 includes a generating phase 130 involving electrically stimulating at least one of the nerves of the impaired body part. The electrical stimulation of the nerve can be performed using the percutaneous therapy electrodes described in the patent applications incorporated by reference above. The percutaneous electrode devices can thus be flexible, wire-type electrodes or rigid, needle-type electrodes. In this embodiment, the electrodes are positioned proximate to the particular nerve(s) in the impaired body part, and then the electrical current is applied to the electrodes. The diagnostic procedure 102 in this embodiment can also include a monitoring phase 132, which can be similar to the monitoring phase 112 described above. Thus, the monitoring phase 132 determines the site where cortical neural activity occurs in response to the electrical stimulation of the nerves.

The embodiment of the diagnostic procedure 102 shown in FIG. 4C is also expected to be useful for providing an accurate image of the intended neural activity in the cortex. By stimulating the nerves instead of passively moving the impaired body part, this embodiment is also expected to reduce the "noise" of neural activity in the brain correlated with the impaired body part. Additionally, stimulating the nerves in the impaired body part may provide an even more precise image of the response neural activity in the brain because it directly involves the nervous system without having to involve other features of the impaired body part.

Another benefit of several embodiments of the diagnostic procedures described above with reference to FIGS. 4B and 4C is that they may generate the intended neural activity in highly impaired body parts. One aspect of severely impaired body parts is that passive motion of such body parts may not generate neural activity in the brain. The electrical stimulation of the muscles and/or the nerves of the impaired body part, however, can provide more stimulus than merely passively moving the muscles. The electrical stimulus may thus generate neural activity related to the impaired body part when passive movement of the impaired body part does not produce an image.

Figure 4D:
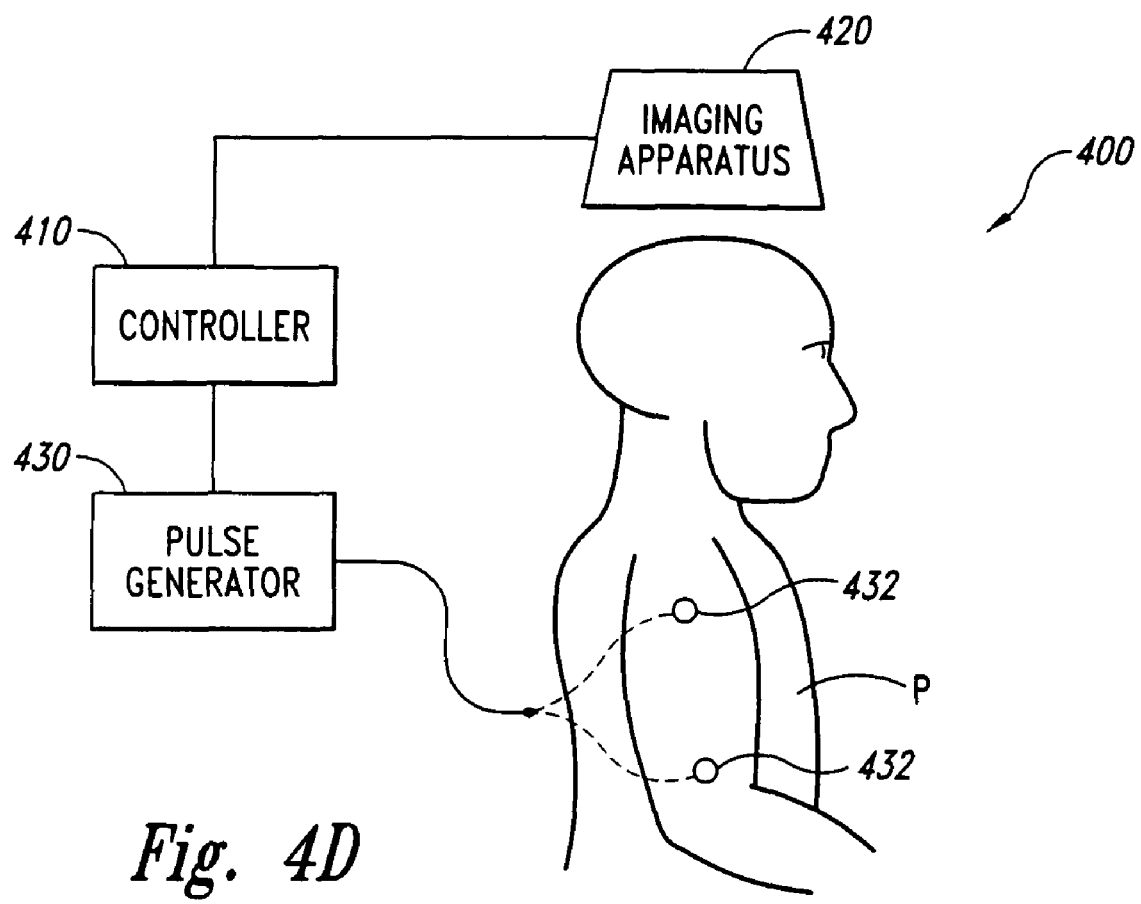
FIG. 4D is a schematic illustration of a system for carrying out the diagnostic and stimulation procedures of FIGS. 4B and 4C.

FIG. 4D schematically illustrates a system 400 for performing the diagnostic procedures described above with respect to FIGS. 4B and 4C. The system 400 includes a controller 410, an imaging apparatus 420 coupled to the controller 410, and a pulse generator 430 coupled to the controller 410. The system 400 can also include a plurality of stimulus elements 432 for providing a stimulus to the affected body part of the patient P. The procedure described with respect to FIG. 4B uses the stimulus elements 432 to stimulate the muscle of the affected body part, whereas the procedure described with respect to FIG. 4C uses the stimulus elements 432 to stimulate the nerves of the affected body part. The stimulus elements 432 can be transcutaneous electrode patches, or they can be percutaneous electrodes, such as those developed by Vertis Neuroscience, Inc. of Seattle, Wash., and described in U.S. application Ser. Nos. 09/666,931 and 09/452,477, which are both herein incorporated by reference. The percutaneous electrodes can be flexible wire-type electrodes or rigid needle-type electrodes. The stimulus elements 432 can alternatively be transcutaneous magnetic elements that provide magnetic stimuli to the affected body part of the patient P. In the example shown in FIG. 4D, the upper arm is the affected body part of the patient P. In operation, the controller 410 instructs the pulse generator 430 to provide a stimulus to the affected body part via the stimulus elements 432. As the stimulus is applied to the affected body part, the imaging apparatus 420 monitors the neural activity in the patient P and generates data corresponding to the observed neural activity.

Figure 4E:
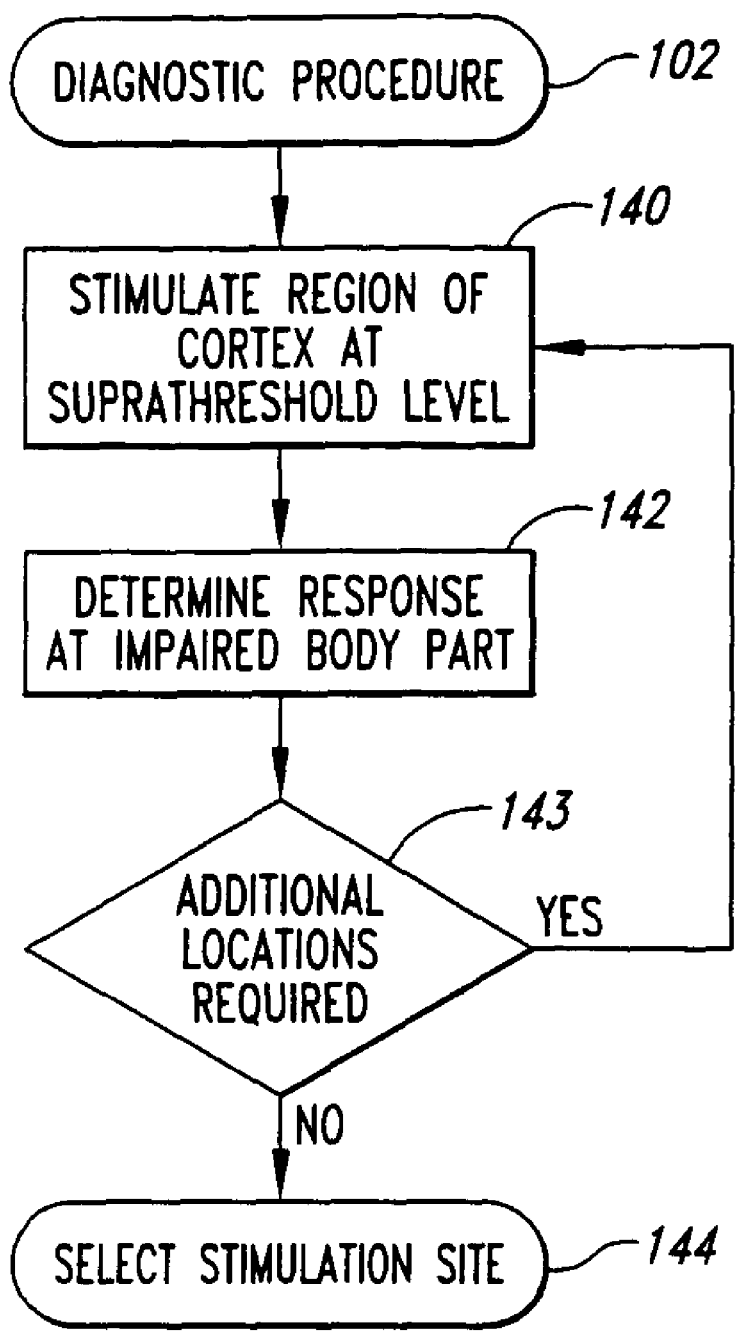
FIG. 4E is a flow chart illustrating another embodiment of a method in accordance with the invention.

FIG. 4E is a flow chart of still another embodiment of the diagnostic procedure 102 in accordance with the invention. In this embodiment, the diagnostic procedure 102 includes a generating phase 140 involving stimulating an area on the cortex at a supra-threshold level, and a monitoring phase 142 involving determining whether the supra-threshold stimulation produced a response in the impaired body part. The generating phase 140 can include implanting an electrode array having a plurality of electrodes to which an electrical current can be applied independently. The region of the cortex for implanting the electrode array can be based upon an estimate of the area where the brain is likely to perform the neural activity to control the impaired body part. After implanting the electrode array, different configurations of electrodes can be activated to apply the electrical stimulation to different areas of the cortex. The generating phase 140 also typically includes applying the electrical stimulation at a supra-threshold level that will cause a motor response, an electrical response, or another type of response that can be measured at the impaired body part.

The monitoring phase 142 of this embodiment of the diagnostic procedure 102 involves measuring the response to the electrical stimulation that was applied to the cortex in the generating phase 140. The response can be detected using electrical sensors at the impaired body part or by detecting movement of the impaired body part. If no response is detected, then the particular area of the cortex to which the stimulation was applied is not likely the motor control area of the cortex that the brain is using to perform neural activity for the impaired body part. The diagnostic procedure 102 can accordingly further include a decision phase 143 in which the practitioner or a computer decides to apply electrical stimulation to another area of the cortex by selecting another electrode configuration on the electrode array. If a response is detected at the impaired body part, then the area of the cortex to which the stimulation was applied is likely involved in performing the neural function for the impaired body part. The diagnostic procedure 102 in this embodiment can also decide to test alternate electrode configurations at the decision phase 143 even when a response to the electrical stimulation is detected to further refine the area of the cortex that is performing the neural activity of the impaired body part. After testing several different electrode configurations, the diagnostic procedure 102 can proceed to the selection phase 144 in which the area of the cortex that provided the desired response in the impaired body part is selected as the site to apply the electrical stimulation.

An alternative embodiment of the diagnostic procedure 102 involves identifying a stimulation site at a second location of the brain where the neural activity has changed in response to a change in the neural-function of the patient. This embodiment of the method does not necessarily require that the intended neural activity be generated by peripherally actuating or stimulating a body part. For example, the brain can be scanned for neural activity associated with the impaired neural-function as a patient regains use of an affected limb or learns a task over a period of time. This embodiment, however, can also include peripherally generating the intended neural activity remotely from the brain explained above.

In still another embodiment, the diagnostic procedure 102 involves identifying a stimulation site at a location of the brain where the intended neural activity is developing to perform the neural-function. This embodiment is similar to the other embodiments of the diagnostic procedure 102, but it can be used to identify a stimulation site at (a) the normal region of the brain where the intended neural activity is expected to occur according to the functional organization of the brain and/or (b) a different region where the neural activity occurs because the brain is recruiting additional matter to perform the neural-function. This particular embodiment of the method involves monitoring neural activity at one or more locations where the neural activity occurs in response to the particular neural-function of interest. For example, to enhance the ability to learn a particular task (e.g., playing a musical instrument, memorizing, etc.), the neural activity can be monitored while a person performs the task or thinks about performing the task. The stimulation sites can be defined by the areas of the brain where the neural activity has the highest intensity, the greatest increases, and/or other parameters that indicate areas of the brain that are being used to perform the particular task.

Figure 5A:
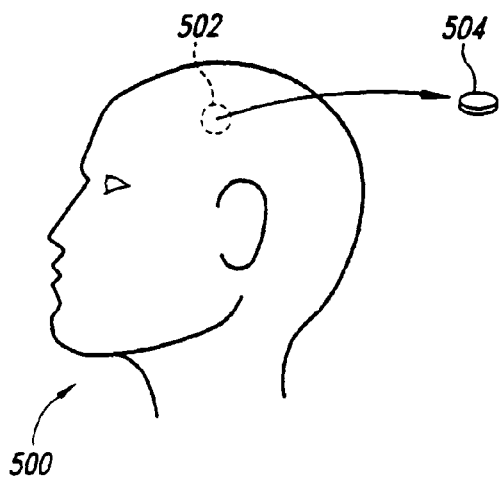
FIGS. 5A and 5B are schematic illustrations of an implanting procedure at a stage of a method in accordance with an embodiment of the invention.
Figure 5B:
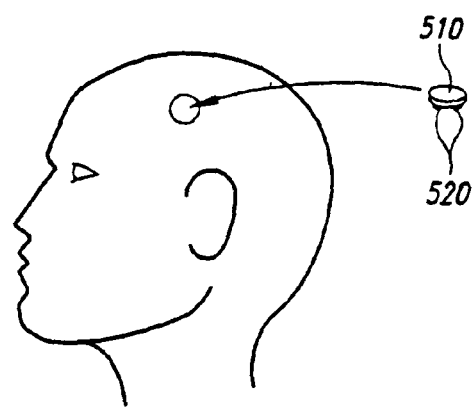

FIGS. 5A and 5B are schematic illustrations of the implanting procedure 104 described above with reference to FIG. 1C for positioning the first and second electrodes relative to a portion of the brain of a patient 500. Referring to FIG. 5A, a stimulation site 502 is identified in accordance with an embodiment of the diagnostic procedure 102. In one embodiment, a skull section 504 is removed from the patient 500 adjacent to the stimulation site 502. The skull section 504 can be removed by boring a hole in the skull in a manner known in the art, or a much smaller hole can be formed in the skull using drilling techniques that are also known in the art. In general, the hole can be 0.2-4.0 cm in diameter. Referring to FIG. 5B, an implantable stimulation apparatus 510 having first and second electrodes 520 can be implanted in the patient 500. Suitable techniques associated with the implantation procedure are known to practitioners skilled in the art. After the stimulation apparatus 510 has been implanted in the patient 500, a pulse system generates electrical pulses that are transmitted to the stimulation site 502 by the first and second electrodes 520. Stimulation apparatus suitable for carrying out the foregoing embodiments of methods in accordance with the invention are described in more detail below with reference to the FIGS. 6-40.

Several embodiments of methods for enhancing neural activity in accordance with the invention are expected to provide lasting results that promote the desired neural-function. Before the present invention, electrical and magnetic stimulation techniques typically stimulated the normal locations of the brain where neural activity related to the neural-functions occurred according to the functional organization of the brain. Such conventional techniques, however, may not be effective because the neurons in the "normal locations" of the brain may not be capable of carrying out the neural activity because of brain damage, disease, disorder, and/or because of variations of the location specific to individual patients. Several embodiments of methods for enhancing neural activity in accordance with the invention overcome this drawback by identifying a stimulation site based on neuroplastic activity that appears to be related to the neural-function. By first identifying a location in the brain that is being recruited to perform the neural activity, it is expected that therapies (e.g., electrical, magnetic, genetic, biologic, and/or pharmaceutical) applied to this location will be more effective than conventional techniques. This is because the location that the brain is recruiting for the neural activity may not be the "normal location" where the neuro activity would normally occur according to the functional organization of the brain. Therefore, several embodiments of methods for enhancing neural activity in accordance with the invention are expected to provide lasting results because the therapies are applied to the portion of the brain where neural activity for carrying out the neural-function actually occurs in the particular patient.

2. Electrically Inducing Desired Neural Activity

The method 100 for effectuating a neural-function can also be used to induce neural activity in a region of the brain where such neural activity is not present. As opposed to the embodiments of the method 100 described above for enhancing existing neural activity, the embodiments of the method 100 for inducing neural activity initiate the neural activity at a stimulation site where it is estimated that neuroplasticity will occur. In this particular situation, an image of the brain seeking to locate where neuroplasticity is occurring may be similar to FIG. 3. An aspect of inducing neural activity, therefore, is to develop a procedure to determine where neuroplasticity is likely to occur.

A stimulation site may be identified by estimating where the brain will likely recruit neurons for performing the neural-function. In one embodiment, the location of the stimulation site is estimated by defining a region of the brain that is proximate to the normal location where neural activity related to the neural-function is generally present according to the functional organization of the brain. An alternative embodiment for locating the stimulation site includes determining where neuroplasticity has typically occurred in patients with similar symptoms. For example, if the brain typically recruits a second region of the cortex to compensate for a loss of neural activity in the normal region of the cortex, then the second region of the cortex can be selected as the stimulation site either with or without imaging the neural activity in the brain.

Several embodiments of methods for inducing neural activity in accordance with the invention are also expected to provide lasting results that initiate and promote a desired neural-function. By first estimating the location of a stimulation site where desired neuroplasticity is expected to occur, therapies applied to this location may be more effective than conventional therapies for reasons that are similar to those explained above regarding enhancing neural activity. Additionally, methods for inducing neural activity may be easier and less expensive to implement because they do not require generating neural activity and/or imaging the brain to determine where the intended neural activity is occurring before applying the therapy.

3. Applications of Methods for Electrically Stimulating Regions of the Brain

The foregoing methods for enhancing existing neural activity or inducing new neural activity are expected to be useful for many applications. As explained above, several embodiments of the method 100 involve determining an efficacious location of the brain to enhance or induce an intended neural activity that causes the desired neural-functions to occur. Additional therapies can also be implemented in combination with the electrical stimulation methods described above. Several specific applications using embodiments of electrical stimulation methods in accordance with the invention either alone or with adjunctive therapies will now be described, but it will be appreciated that the methods in accordance with the invention can be used in many additional applications.

a. General Applications

The embodiments of the electrical stimulation methods described above are expected to be particularly useful for rehabilitating a loss of mental functions, motor functions and/or sensory functions caused by damage to the brain. In a typical application, the brain has been damaged by a stroke or trauma (e.g., automobile accident). The extent of the particular brain damage can be assessed using functional MRI or another appropriate imaging technique as explained above with respect to FIG. 3. A stimulation site can then be identified by: (a) peripherally stimulating a body part that was affected by the brain damage to induce the intended neural activity and determining the location where a response neural activity occurs; (b) determining where the neural activity has changed as a patient gains more use of the affected body part; and/or (c) estimating the location that the brain may recruit neurons to carry out the neural activity that was previously performed by the damaged portion of the brain. An electrical stimulation therapy can then be applied to the selected stimulation site by placing the first and second electrodes relative to the stimulation site to apply an electrical current in that portion of the brain. As explained in more detail below, it is expected that applying an electrical current to the portion of the brain that has been recruited to perform the neural activity related to the affected body part will produce a lasting neurological effect for rehabilitating the affected body part.

Several specific applications are expected to have a stimulation site in the cortex because neural activity in this part of the brain effectuates motor functions and/or sensory functions that are typically affected by a stroke or trauma. In these applications, the electrical stimulation can be applied directly to the pial surface of the brain or at least proximate to the pial surface (e.g., the dura mater, the fluid surrounding the cortex, or neurons within the cortex). Suitable devices for applying the electrical stimulation to the cortex are described in detail with reference to FIGS. 6-40.

The electrical stimulation methods can also be used with adjunctive therapies to rehabilitate damaged portions of the brain. In one embodiment, the electrical stimulation methods can be combined with physical therapy and/or drug therapies to rehabilitate an affected neural function. For example, if a stroke patient has lost the use of a limb, the patient can be treated by applying the electrical therapy to a stimulation site where the intended neural activity is present while the affected limb is also subject to physical therapy. An alternative embodiment can involve applying the electrical therapy to the stimulation site and chemically treating the patient using amphetamines or other suitable drugs.

The embodiments of the electrical stimulation methods described above are also expected to be useful for treating brain diseases, such as Alzheimer's, Parkinson's, and other brain diseases. In this application, the stimulation site can be identified by monitoring the neural activity using functional MRI or other suitable imaging techniques over a period of time to determine where the brain is recruiting material to perform the neural activity that is being affected by the disease. It may also be possible to identify the stimulation site by having the patient try to perform an act that the particular disease has affected, and monitoring the brain to determine whether any response neural activity is present in the brain. After identifying where the brain is recruiting additional matter, the electrical stimulation can be applied to this portion of the brain. It is expected that electrically stimulating the regions of the brain that have been recruited to perform the neural activity which was affected by the disease will assist the brain in offsetting the damage caused by the disease.

The embodiments of the electrical stimulation methods described above are also expected to be useful for treating neurological disorders, such as depression, passive-aggressive behavior, weight control, and other disorders. In these applications, the electrical stimulation can be applied to a stimulation site in the cortex or another suitable part of the brain where neural activity related to the particular disorder is present. The embodiments of electrical stimulation methods for carrying out the particular therapy can be adapted to either increase or decrease the particular neural activity in a manner that produces the desired results. For example, an amputee may feel phantom sensations associated with the amputated limb. This phenomenon can be treated by applying an electrical pulse that reduces the phantom sensations. The electrical therapy can be applied so that it will modulate the ability of the neurons in that portion of the brain to execute sensory functions.

b. Pulse Forms and Potentials

The electrical stimulation methods in accordance with the invention can use several different pulse forms to effectuate the desired neuroplasticity. The pulses can be a bi-phasic or monophasic stimulus that is applied to achieve a desired potential in a sufficient percentage of a population of neurons at the stimulation site. In one embodiment, the pulse form has a frequency of approximately 2-1000 Hz, but the frequency may be particularly useful in the range of approximately 40-200 Hz. For example, initial clinical trials are expected to use a frequency of approximately 50-100 Hz. The pulses can also have pulse widths of approximately 10 µs-100 ms, or more specifically the pulse width can be approximately 20-200 µs. For example, a pulse width of 50-100 µs may produce beneficial results.

It is expected that one particularly useful application of the invention involves enhancing or inducing neuroplasticity by raising the resting membrane potential of neurons to bring the neurons closer to the threshold level for firing an action potential. Because the stimulation raises the resting membrane potential of the neurons, it is expected that these neurons are more likely to "fire" an action potential in response to excitatory input at a lower level.

Figure 5C:
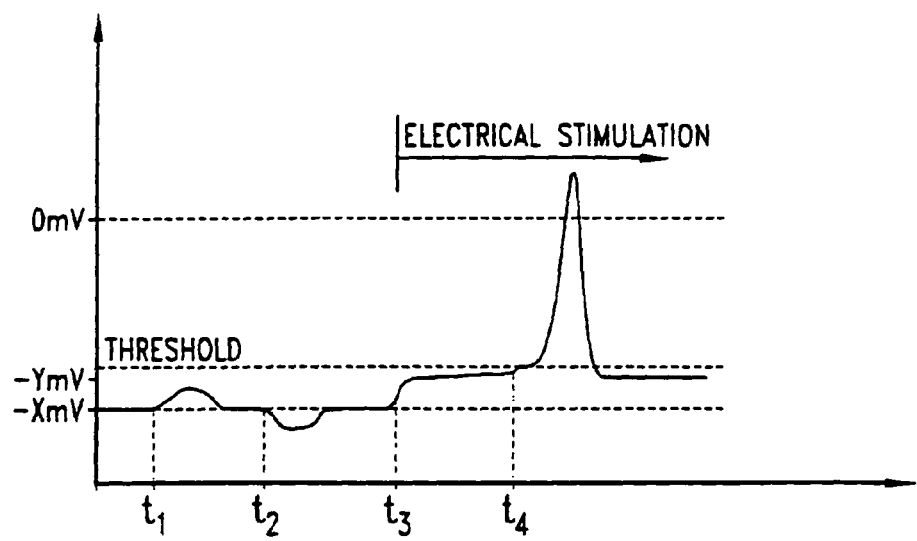
FIG. 5C is a graph illustrating firing an "action potential" associated with stimulated neural activity in accordance with one embodiment of the invention.

FIG. 5C is a graph illustrating applying a subthreshold potential to the neurons N1-N3 of FIG. 1A. At times $t_1$ and $t_2$, the excitory/inhibitory inputs from other neurons do not "bridge-the-gap" from the resting potential at $-X$ mV to the threshold potential. At time $t_3$, the electrical stimulation is applied to the brain to raise the resting potential of neurons in the stimulated population such that the resting potential is at $-Y$ mV. As such, at time $t_4$ when the neurons receive another excitatory input, even a small input exceeds the gap between the raised resting potential $-Y$ mV and the threshold potential to induce action potentials in these neurons. For example, if the resting potential is approximately $-70$ mV and the threshold potential is approximately $-50$ mV, then the electrical stimulation can be applied to raise the resting potential of a sufficient number of neurons to approximately $-52$ to $-60$ mV.

The actual electrical potential applied to electrodes implanted in the brain to achieve a subthreshold potential stimulation will vary according to the individual patient, the type of therapy, the type of electrodes, and other factors. In general, the pulse form of the electrical stimulation (e.g., the frequency, pulse width, wave form, and voltage potential) is selected to raise the resting potential in a sufficient number neurons at the stimulation site to a level that is less than a threshold potential for a statistical portion of the neurons in the population. The pulse form, for example, can be selected so that the applied voltage of the stimulus achieves a change in the resting potential of approximately 10%-95%, and more specifically of 60%-80%, of the difference between the unstimulated resting potential and the threshold potential.

In one specific example of a subthreshold application for treating a patient's hand, electrical stimulation is not initially applied to the stimulation site. Although physical therapy related to the patient's hand may cause some activation of a particular population of neurons that is known to be involved in "hand function," only a low level of activation might occur because physical therapy only produces a low level of action potential generation in that population of neurons. However, when the subthreshold electrical stimulation is applied, the resting membrane potentials of the neurons in the stimulated population are elevated. These neurons now are much closer to the threshold for action potential formation such that when the same type of physical therapy is given, this population of cells will have a higher level of activation because these cells are more likely to fire action potentials.

Subthreshold stimulation may produce better results than simply stimulating the neurons with sufficient energy levels to exceed the threshold for action potential formation. One aspect of subthreshold stimulation is to increase the probability that action potentials will occur in response to the ordinary causes of activation—such as physical therapy. This will allow the neurons in this functional network to become entrained together, or "learn" to become associated with these types of activities. If neurons are given so much electricity that they continually fire action potentials without additional excitatory inputs (suprathreshold stimulation), this will create "noise" and disorganization that will not likely cause improvement in function. In fact, neurons that are "overdriven" soon deplete their neurotransmitters and effectively become silent.

The application of a subthreshold stimulation is very different than suprathreshold stimulation. Subthreshold stimulation in accordance with several embodiments of the invention, for example, does not intend to directly make neurons fire action potentials with the electrical stimulation in a significant population of neurons at the stimulation site. Instead, subthreshold stimulation attempts to decrease the "activation energy" required to activate a large portion of the neurons at the stimulation site. As such, subthreshold stimulation in accordance with certain embodiments of the invention is expected to increase the probability that the neurons will fire in response to the usual intrinsic triggers, such as trying to move a limb, physical therapy, or simply thinking about movement of a limb, etc. Moreover, coincident stimulation associated with physical therapy is expected to increase the probability that the action potentials that are occurring with an increased probability due to the subthreshold stimulation will be related to meaningful triggers, and not just "noise."

The stimulus parameters set forth above, such as a frequency selection of approximately 50-100 Hz and an amplitude sufficient to achieve an increase of 60% to 80% of the difference between the resting potential and the threshold potential are specifically selected so that they will increase the resting membrane potential of the neurons, thereby increasing the likelihood that they will fire action potentials, without directly causing action potentials in most of the neuron population. In addition, and as explained in more detail below with respect to FIGS. 6-40, several embodiments of stimulation apparatus in accordance with the invention are designed to precisely apply a pulse form that produces subthreshold stimulation by selectively stimulating regions of the cerebral cortex of approximately 1-2 cm (the estimated size of a "functional unit" of cortex), directly contacting the pial surface with the electrodes to consistently create the same alterations in resting membrane potential, and/or biasing the electrodes against the pial surface to provide a positive connection between the electrodes and the cortex.

B. Devices for Electrically Stimulating Regions of the Brain

FIGS. 6-40 illustrate stimulation apparatus in accordance with several embodiments of the invention for electrically stimulating regions of the brain in accordance with one or more of the methods described above. The devices illustrated in FIGS. 6-40 are generally used to stimulate a region of the cortex proximate to the pial surface of the brain (e.g., the dura mater, the pia mater, the fluid between the dura mater and the pia mater, and a depth in the cortex outside of the white matter of the brain). The devices can also be adapted for stimulating other portions of the brain in other embodiments.

1. Implantable Stimulation Apparatus with Integrated Pulse Systems

Figure 6:
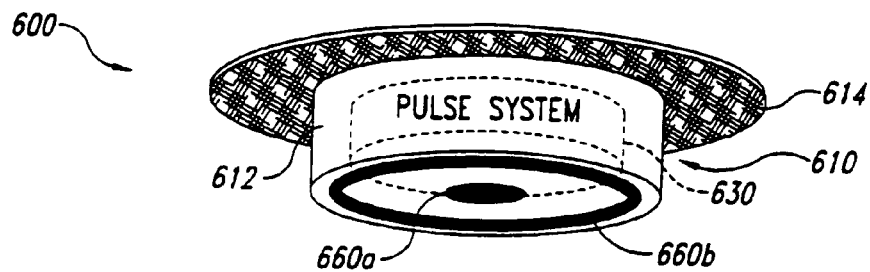
FIG. 6 is an isometric view of an implantable stimulation apparatus in accordance with one embodiment of the invention.
Figure 7:
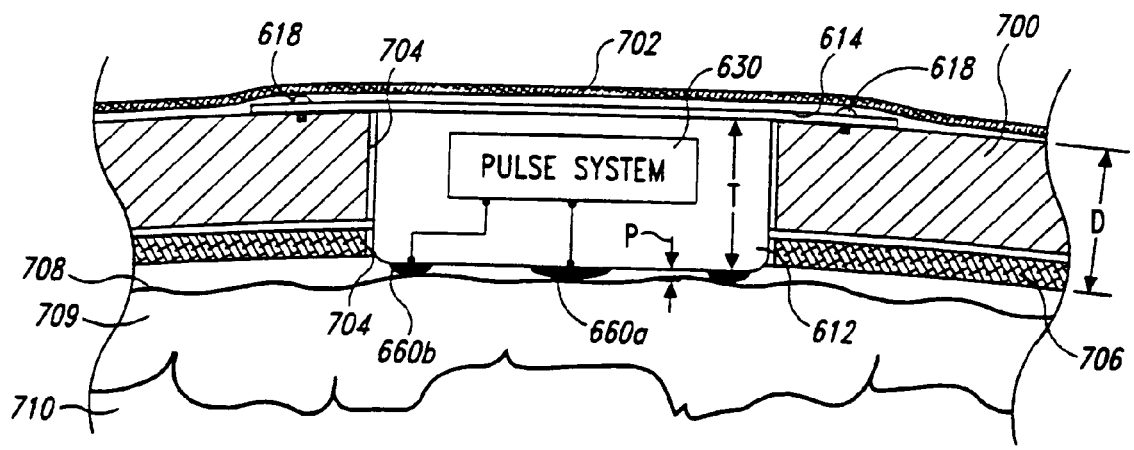
FIG. 7 is a cross-sectional view schematically illustrating a part of an implantable stimulation apparatus in accordance with an embodiment of the invention.

FIG. 6 is an isometric view and FIG. 7 is a cross-sectional view of a stimulation apparatus 600 in accordance with an embodiment of the invention for stimulating a region of the cortex proximate to the pial surface. In one embodiment, the stimulation apparatus 600 includes a support member 610, an integrated pulse-system 630 (shown schematically) carried by the support member 610, and first and second electrodes 660 (identified individually by reference numbers 660a and 660b). The first and second electrodes 660 are electrically coupled to the pulse system 630. The support member 610 can be configured to be implanted into the skull or another intracranial region of a patient. In one embodiment, for example, the support member 610 includes a housing 612 and an attachment element 614 connected to the housing 612. The housing 612 can be a molded casing formed from a biocompatible material that has an interior cavity for carrying the pulse system 630. The housing can alternatively be a biocompatible metal or another suitable material. The housing 612 can have a diameter of approximately 1-4 cm, and in many applications the housing 612 can be 1.5-2.5 cm in diameter. The housing 612 can also have other shapes (e.g., rectilinear, oval, elliptical) and other surface dimensions. The stimulation apparatus 600 can weigh 35 g or less and/or occupy a volume of 20 cc or less. The attachment element 614 can be a flexible cover, a rigid plate, a contoured cap, or another suitable element for holding the support member 610 relative to the skull or other body part of the patient. In one embodiment, the attachment element 614 is a mesh, such as a biocompatible polymeric mesh, metal mesh, or other suitable woven material. The attachment element 614 can alternatively be a flexible sheet of Mylar, a polyester, or another suitable material.

FIG. 7, more specifically, is a cross-sectional view of the stimulation apparatus 600 after it has been implanted into a patient in accordance with an embodiment of the invention. In this particular embodiment, the stimulation apparatus 600 is implanted into the patient by forming an opening in the scalp 702 and cutting a hole 704 through the skull 700 and through the dura mater 706. The hole 704 should be sized to receive the housing 612 of the support member 610, and in most applications, the hole 704 should be smaller than the attachment element 614. A practitioner inserts the support member 610 into the hole 704 and then secures the attachment element 614 to the skull 700. The attachment element 614 can be secured to the skull using a plurality of fasteners 618 (e.g., screws, spikes, etc.) or an adhesive. In an alternative embodiment, a plurality of downwardly depending spikes can be formed integrally with the attachment element 614 to define anchors that can be driven into the skull 700.

The embodiment of the stimulation apparatus 600 shown in FIG. 7 is configured to be implanted into a patient so that the electrodes 660 contact a desired portion of the brain at the stimulation site. The housing 612 and the electrodes 660 can project from the attachment element 614 by a distance "D" such that the electrodes 660 are positioned at least proximate to the pia mater 708 surrounding the cortex 709. The electrodes 660 can project from a housing 612 as shown in FIG. 7, or the electrodes 660 can be flush with the interior surface of the housing 612. In the particular embodiment shown in FIG. 7, the housing 612 has a thickness "T" and the electrodes 660 project from the housing 612 by a distance "P" so that the electrodes 660 press against the surface of the pia mater 708. The thickness of the housing 612 can be approximately 0.5-4 cm, and is more generally about 1-2 cm. The configuration of the stimulation apparatus 600 is not limited to the embodiment shown in FIGS. 6 and 7, but rather the housing 612, the attachment element 614, and the electrodes 660 can be configured to position the electrodes in several different regions of the brain. For example, in an alternate embodiment, the housing 612 and the electrodes 660 can be configured to position the electrodes deep within the cortex 709, and/or a deep brain region 710. In general, the electrodes can be flush with the housing or extend 0.1 mm to 5 cm from the housing.

More specific embodiments of pulse system and electrode configurations for the stimulation apparatus will be described below.

Several embodiments of the stimulation apparatus 600 are expected to be more effective than existing transcranial electrical stimulation devices and transcranial magnetic stimulation devices. It will be appreciated that much of the power required for transcranial therapies is dissipated in the scalp and skull before it reaches the brain. In contrast to conventional transcranial stimulation devices, the stimulation apparatus 600 is implanted so that the electrodes are at least proximate to the pial surface of the brain 708. Several embodiments of methods in accordance with the invention can use the stimulation apparatus 600 to apply an electrical therapy directly to the pia mater 708, the dura mater 706, and/or another portion of the cortex 709 at significantly lower power levels than existing transcranial therapies. For example, a potential of approximately 1 mV to 10 V can be applied to the electrodes 660; in many instances a potential of 100 mV to 5 V can be applied to the electrodes 660 for selected applications. It will also be appreciated that other potentials can be applied to the electrodes 660 of the stimulation apparatus 600 in accordance with other embodiments of the invention.

Selected embodiments of the stimulation apparatus 600 are also capable of applying stimulation to a precise stimulation site. Again, because the stimulation apparatus 600 positions the electrodes 660 at least proximate to the pial surface 708, precise levels of stimulation with good pulse shape fidelity will be accurately transmitted to the stimulation site in the brain. It will be appreciated that transcranial therapies may not be able to apply stimulation to a precise stimulation site because the magnetic and electrical properties of the scalp and skull may vary from one patient to another such that an identical stimulation by the transcranial device may produce a different level of stimulation at the neurons in each patient. Moreover, the ability to focus the stimulation to a precise area is hindered by delivering the stimulation transcranially because the scalp, skull and dura all diffuse the energy from a transcranial device. Several embodiments of the stimulation apparatus 600 overcome this drawback because the electrodes 660 are positioned under the skull 700 such that the pulses generated by the stimulation apparatus 600 are not diffused by the scalp 702 and skull 700.

2. Integrated Pulse Systems for Implantable Stimulation Apparatus

The pulse system 630 shown in FIGS. 6 and 7 generates and/or transmits electrical pulses to the electrodes 660 to create an electrical field at a stimulation site in a region of the brain. The particular embodiment of the pulse system 630 shown in FIG. 7 is an "integrated" unit in that is carried by the support member 610. The pulse system 630, for example, can be housed within the housing 612 so that the electrodes 660 can be connected directly to the pulse system 630 without having leads outside of the stimulation apparatus 600. The distance between the electrodes 660 and the pulse system 630 can be less than 4 cm, and it is generally 0.10 to 2.0 cm. The stimulation apparatus 600 can accordingly provide electrical pulses to the stimulation site without having to surgically create tunnels running through the patient to connect the electrodes 660 to a pulse generator implanted remotely from the stimulation apparatus 600. It will be appreciated, however, that alternative embodiments of stimulation apparatus in accordance with the invention can include a pulse system implanted separately from the stimulation apparatus 600 in the cranium or an external pulse system. Several particular embodiments of pulse systems that are suitable for use with the stimulation apparatus 600 will now be described in more detail.

Figure 8:
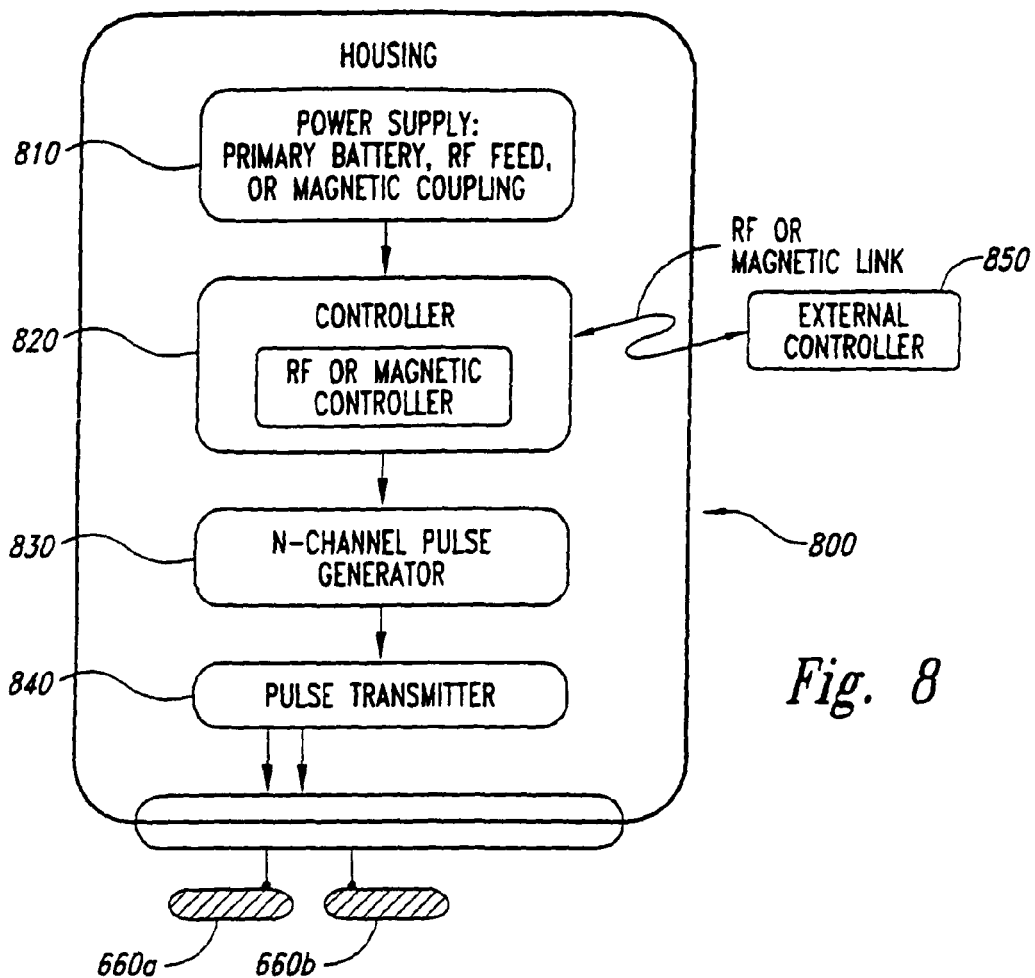
FIG. 8 is a schematic illustration of a pulse system in accordance with one embodiment of the invention.
Figure 9:
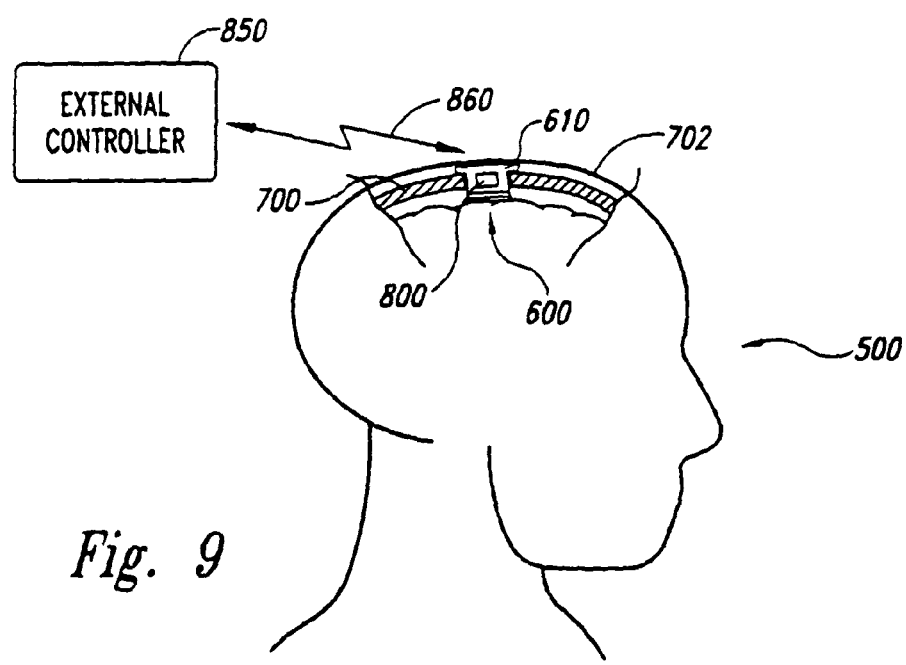
FIG. 9 is a schematic illustration of an implanted stimulation apparatus and an external controller in accordance with an embodiment of the invention.

FIGS. 8 and 9 schematically illustrate an integrated pulse system 800 in accordance with one embodiment of the invention for being implanted in the cranium within the stimulation apparatus 600. Referring to FIG. 8, the pulse system 800 can include a power supply 810, an integrated controller 820, a pulse generator 830, and a pulse transmitter 840. The power supply 810 can be a primary battery, such as a rechargeable battery or another suitable device for storing electrical energy. In alternative embodiments, the power supply 810 can be an RF transducer or a magnetic transducer that receives broadcast energy emitted from an external power source and converts the broadcast energy into power for the electrical components of the pulse system 800. The integrated controller 820 can be a wireless device that responds to command signals sent by an external controller 850. The integrated controller 820, for example, can communicate with the external controller 850 by RF or magnetic links 860. The integrated controller 820 provides control signals to the pulse generator 830 in response to the command signals sent by the external controller 850. The pulse generator 830 can have a plurality of channels that send appropriate electrical pulses to the pulse transmitter 840, which is coupled to the electrodes 660. Suitable components for the power supply 810, the integrated controller 820, the pulse generator 830, and the pulse transmitter 840 are known to persons skilled in the art of implantable medical devices.

Referring to FIG. 9, the pulse system 800 can be carried by the support member 610 of the stimulation apparatus 600 in the manner described above with reference to FIGS. 6 and 7. The external controller 850 can be located externally to the patient 500 so that the external controller 850 can be used to control the pulse system 800. In one embodiment, several patients that require a common treatment can be simultaneously treated using a single external controller 850 by positioning the patients within the operating proximity of the controller 850. In an alternative embodiment, the external controller 850 can contain a plurality of operating codes and the integrated controller 820 for a particular patient can have an individual operating code. A single controller 850 can thus be used to treat a plurality of different patients by entering the appropriate operating code into the controller 850 corresponding to the particular operating codes of the integrated controllers 820 for the patients.

Figure 10:
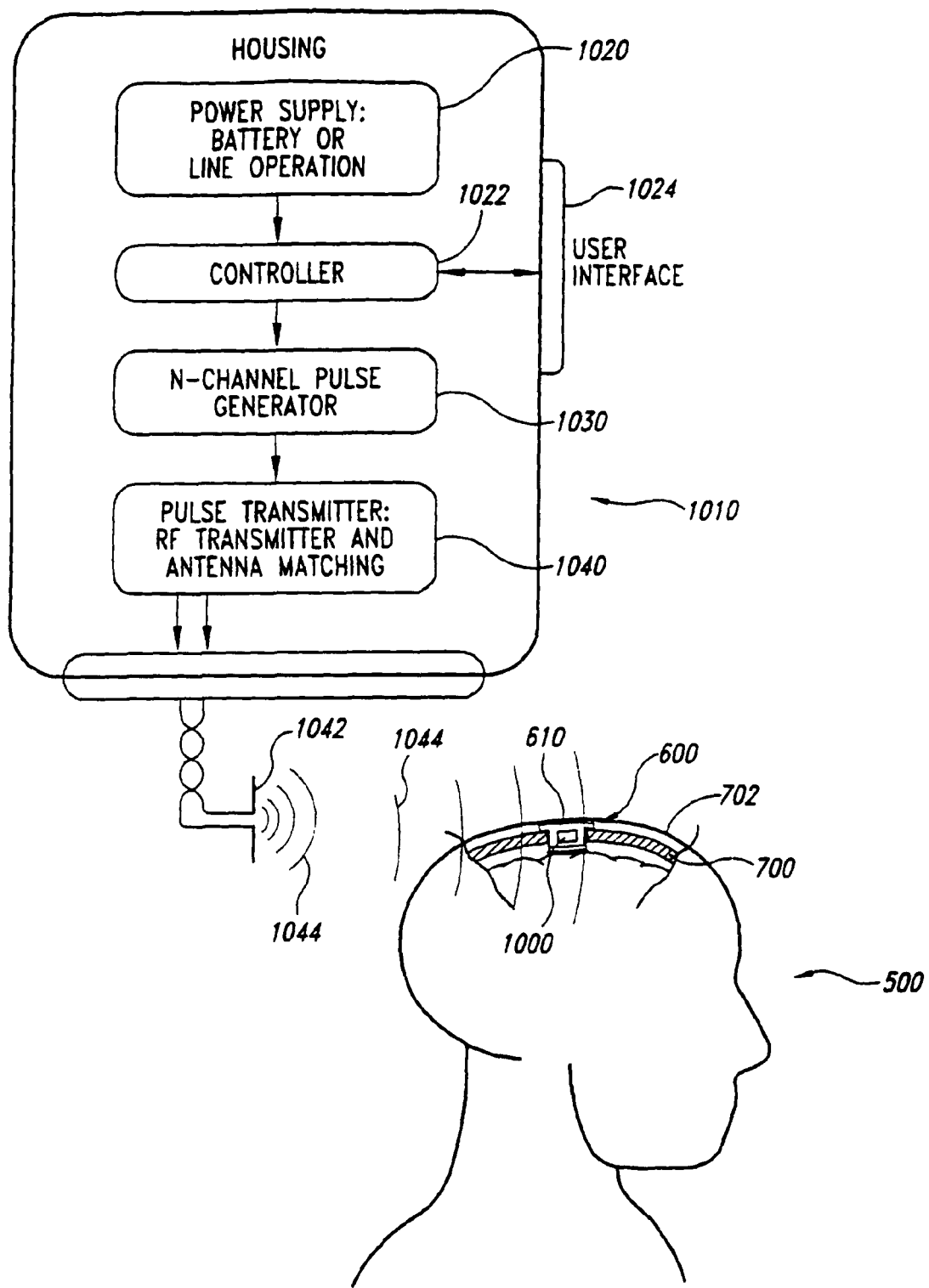
FIG. 10 is a schematic illustration of an implantable stimulation apparatus having a pulse system and an external controller in accordance with another embodiment of the invention.

FIG. 10 is a schematic view illustrating a pulse system 1000 and an external controller 1010 for use with the stimulation apparatus 600 in accordance with another embodiment of the invention. In this embodiment, the external controller 1010 includes a power supply 1020, a controller 1022 coupled to the power supply 1020, and a user interface 1024 coupled to the controller 1022. The external controller 1010 can also include a pulse generator 1030 coupled to the power supply 1020, a pulse transmitter 1040 coupled to the pulse generator 1030, and an antenna 1042 coupled to the pulse transmitter 1040. The external controller 1010 generates the power and the pulse signal, and the antenna 1042 transmits a pulse signal 1044 to the pulse system 1000 in the stimulation apparatus 600. The pulse system 1000 receives the pulse signal 1044 and delivers an electrical pulse to the electrodes. The pulse system 1000, therefore, does not necessarily include an integrated power supply, controller and pulse generator within the housing 610 because these components are in the external controller 1010.

Figure 11:
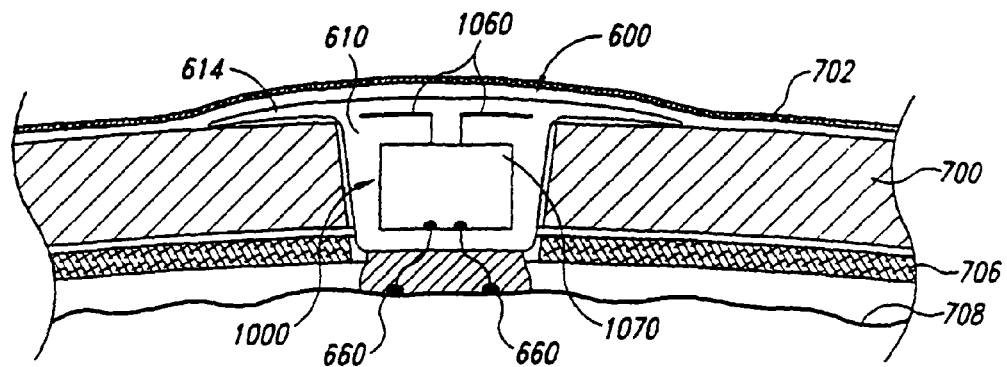
FIG. 11 is a cross-sectional view schematically illustrating a part of an implantable stimulation apparatus in accordance with an embodiment of the invention.

FIG. 11 is a schematic view illustrating an embodiment of the pulse system 1000 in greater detail. In this embodiment, the pulse system 1000 is carried by the support member 610 of the stimulation apparatus 600. The pulse system 1000 can include an antenna 1060 and a pulse delivery system 1070 coupled to the antenna 1060. The antenna 1060 receives the pulse signal 1044 from the external controller 1010 and sends the pulse signal 1044 to the pulse delivery system 1070, which transforms the pulse signal 1044 into electrical pulses. Accordingly, the electrodes 660 can be coupled to the pulse delivery system 1070. The pulse delivery system 1070 can include a filter to remove noise from the pulse signal 1044 and a pulse former that creates an electrical pulse from the pulse signal 1044. The pulse former can be driven by the energy in the pulse signal 1044, or in an alternative embodiment, the pulse system 1000 can also include an integrated power supply to drive the pulse former.

Figure 12:
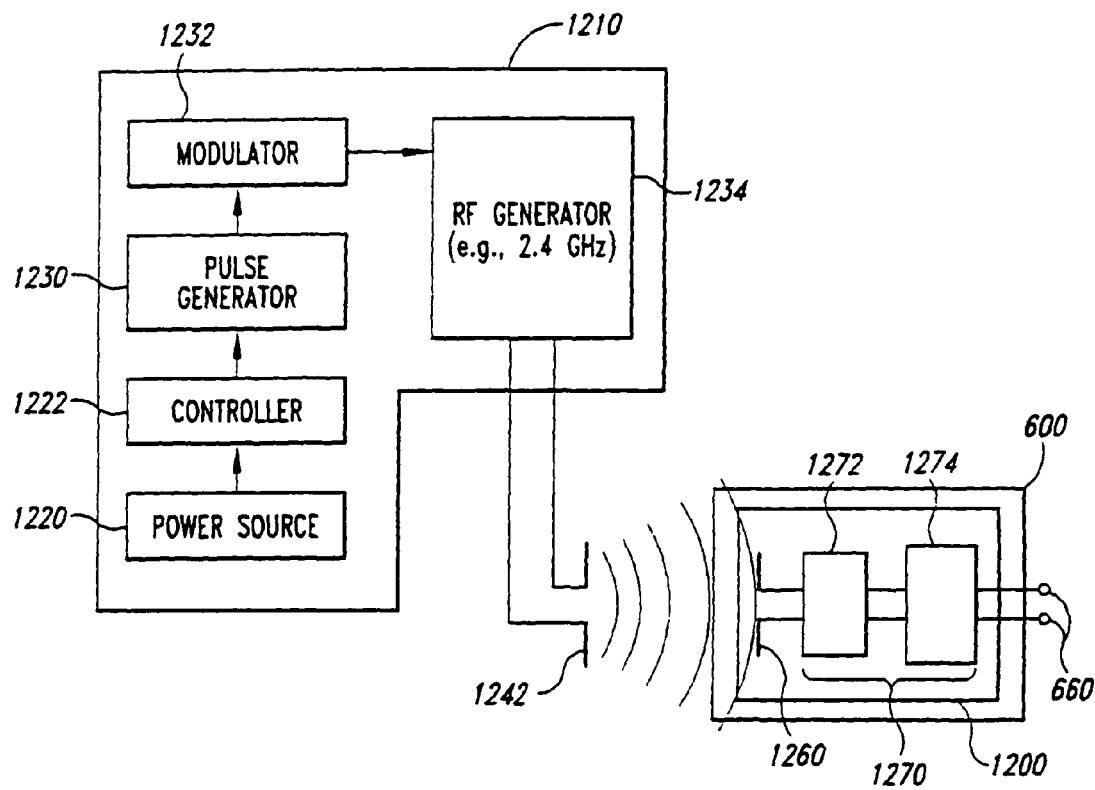
FIG. 12 is a schematic illustration of an implantable stimulation apparatus having a pulse system and an external controller in accordance with another embodiment of the invention.

FIG. 12 is a schematic view illustrating an embodiment of pulse system 1200 for use in an embodiment of the stimulation apparatus 600, and an external controller 1210 for controlling the pulse system 1200 remotely from the patient using RF energy. In this embodiment, the external controller 1210 includes a power supply 1220, a controller 1222 coupled to the power supply 1220, and a pulse generator 1230 coupled to the controller 1222. The external controller 1210 can also include a modulator 1232 coupled to the pulse generator 1230 and an RF generator 1234 coupled to the modulator 1232. In operation, the external controller 1210 broadcasts pulses of RF energy via an antenna 1242.

The pulse system 1200 can be housed within the stimulation apparatus 600 (not shown). In one embodiment, the pulse system 1200 includes an antenna 1260 and a pulse delivery system 1270. The antenna 1260 incorporates a diode (not shown) that rectifies the broadcast RF energy from the antenna 1242. The pulse delivery system 1270 can include a filter 1272 and a pulse former 1274 that forms electrical pulses which correspond to the RF energy broadcast from the antenna 1242. The pulse system 1200 is accordingly powered by the RF energy in the pulse signal from the external controller 1210 such that the pulse system 1200 does not need a separate power supply carried by the stimulation apparatus 600.

Figure 13:
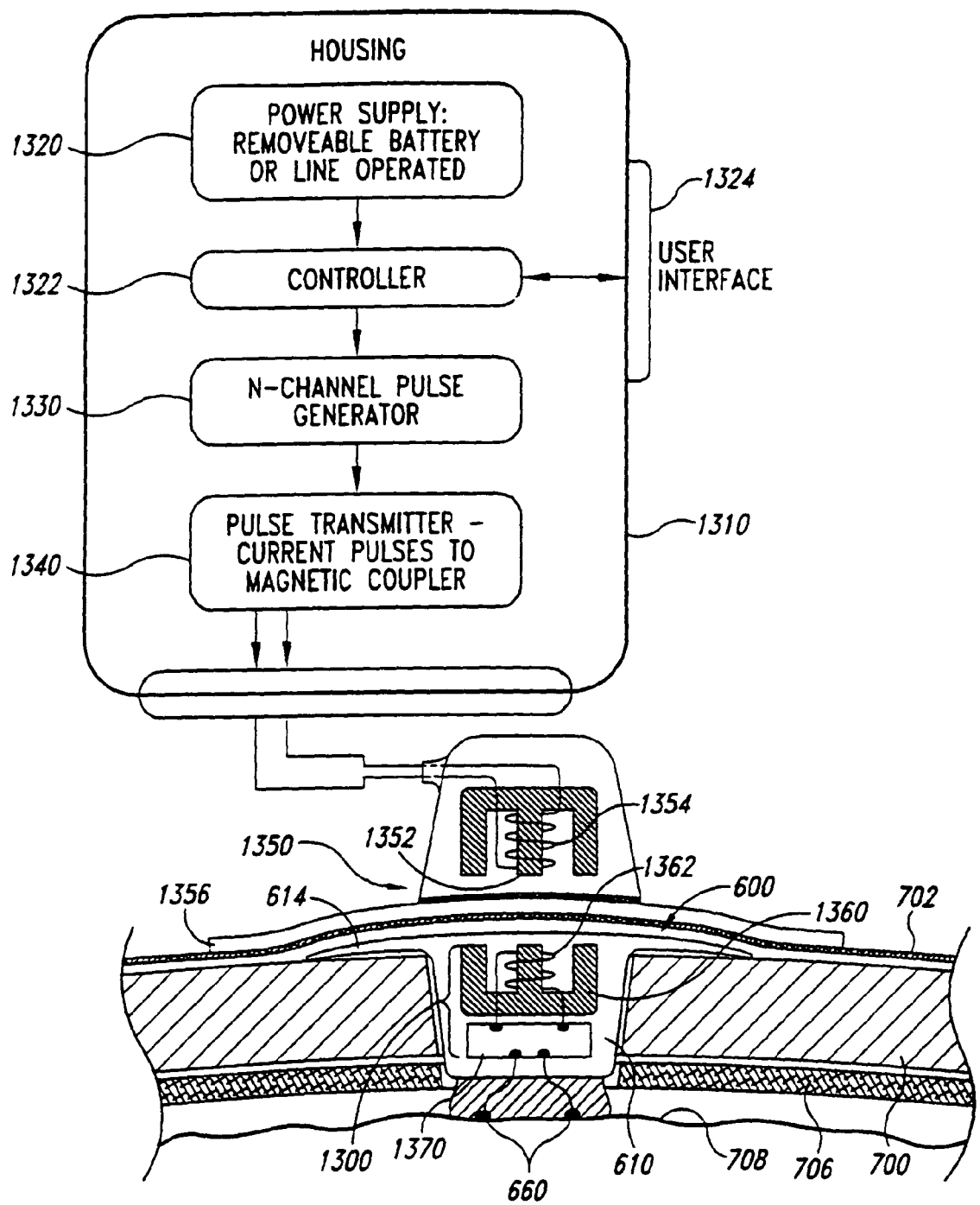
FIG. 13 is a cross-sectional view schematically illustrating a part of an implantable stimulation apparatus having a pulse system and an external controller in accordance with another embodiment of the invention.

FIG. 13 is a cross-sectional view of a pulse system 1300 for use in another embodiment of the implantable stimulation apparatus 600, together with an external controller 1310 for remotely controlling the pulse system 1300 externally from the patient using magnetic energy. In this embodiment, the external controller 1310 includes a power supply 1320, a controller 1322 coupled to the power supply 1320, and a user interface 1324 coupled to the controller 1322. The external controller 1310 can also include a pulse generator 1330 coupled to the controller 1332, a pulse transmitter 1340 coupled to the pulse generator 1330, and a magnetic coupler 1350 coupled to the pulse transmitter 1340. The magnetic coupler 1350 can include a ferrite core 1352 and a coil 1354 wrapped around a portion of the ferrite core 1352. The coil 1354 can also be electrically connected to the pulse transmitter 1340 so that electrical pulses applied to the coil 1354 generate changes in a corresponding magnetic field. The magnetic coupler 1350 can also include a flexible cap 1356 to position the magnetic coupler 1350 over the implanted stimulation apparatus 600.

The pulse system 1300 can include a ferrite core 1360 and a coil 1362 wrapped around a portion of the ferrite core 1360. The pulse system 1310 can also include a pulse delivery system 1370 including a rectifier and a pulse former. In operation, the ferrite core 1360 and the coil 1362 convert the changes in the magnetic field generated by the magnetic coupler 1350 into electrical pulses that are sent to the pulse delivery system 1370. The electrodes 660 are coupled to the pulse delivery system 1370 so that electrical pulses corresponding to the electrical pulses generated by the pulse generator 1330 in the external controller 1310 are delivered to the stimulation site on the patient.

3. Electrode Configurations

Figure 21:
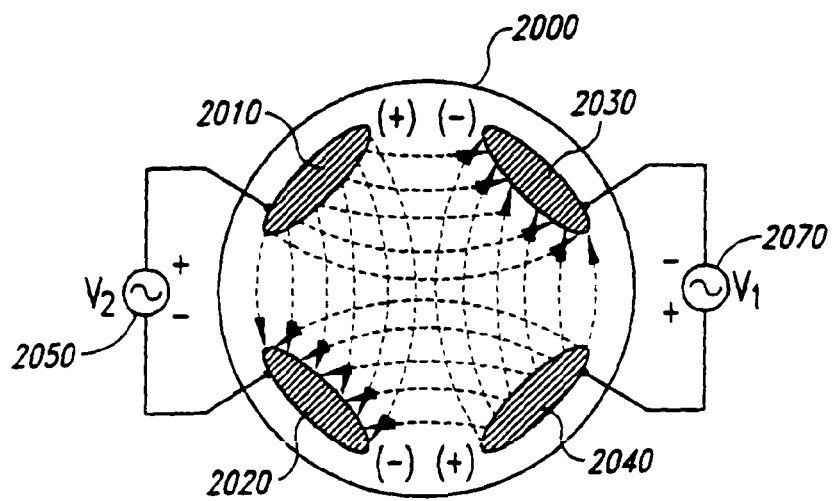
FIG. 21 is a bottom plan view of an electrode configuration for an implantable stimulation device in accordance with another embodiment of the invention.
Figure 22:
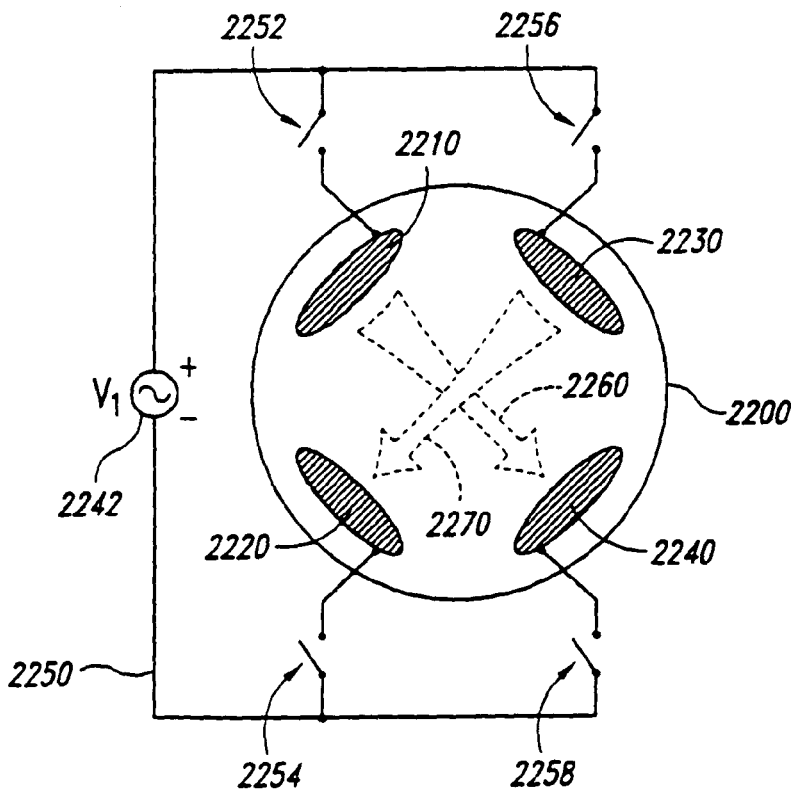
FIG. 22 is a bottom plan view of yet another embodiment of an electrode configuration for use with an implantable stimulation apparatus in accordance with the invention.
Figure 23:
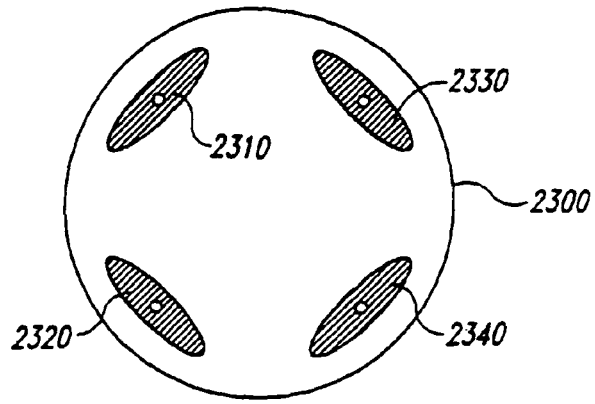
FIG. 23 is a bottom plan view.
Figure 24:
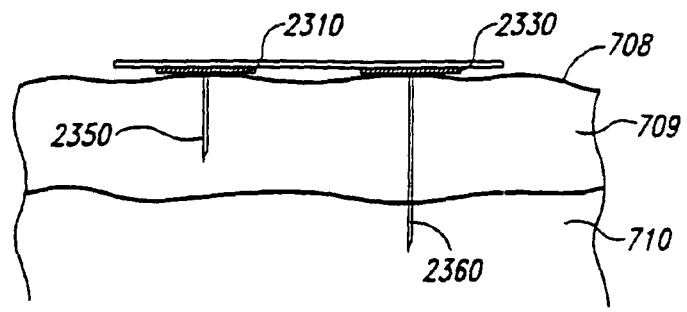
FIG. 24 is a cross-sectional view of an electrode configuration for use with a stimulation apparatus in accordance with still another embodiment of the invention.

FIGS. 14-24 illustrate electrodes in accordance with various embodiments of the invention that can be used with the stimulation apparatus disclosed herein. FIGS. 14-22 illustrate embodiments of electrodes configured to apply an electrical current to a stimulation site at least proximate to the pial surface of the cortex, and FIGS. 23 and 24 illustrate embodiments of electrodes configured to apply an electrical current within the cortex or below the cortex. It will be appreciated that other configurations of electrodes can also be used with other implantable stimulation apparatus.

Figure 14:
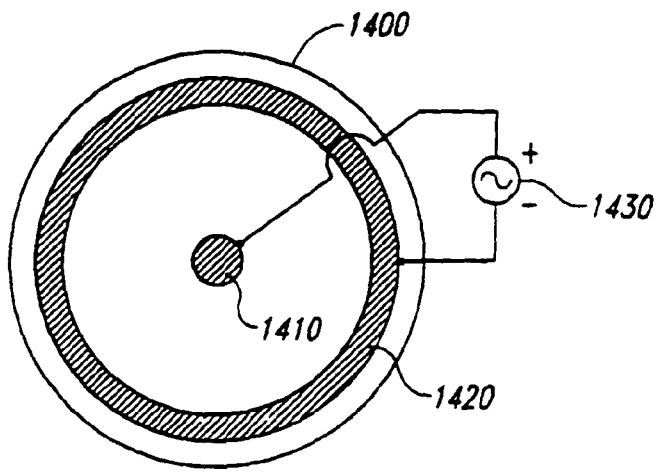
FIG. 14 is a bottom plan view.
Figure 15:
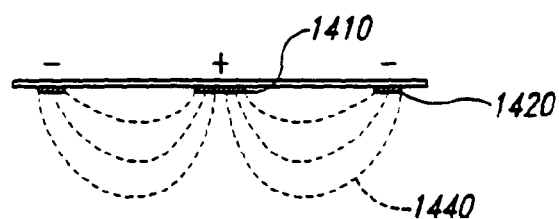
FIG. 15 is a cross-sectional view illustrating an electrode configuration for an implantable stimulation apparatus in accordance with an embodiment of the invention.

FIG. 14 is a bottom plan view and FIG. 15 is a cross-sectional view of a stimulation apparatus 1400 in accordance with an embodiment of the invention. In this embodiment, the stimulation apparatus 1400 includes a first electrode 1410 and a second electrode 1420 concentrically surrounding the first electrode 1410. The first electrode 1410 can be coupled to the positive terminal of a pulse generator 1430, and the second electrode 1420 can be coupled to the negative terminal of the pulse generator 1430. Referring to FIG. 15, the first and second electrodes 1410 and 1420 generate a toroidal electric field 1440.

Figure 16:
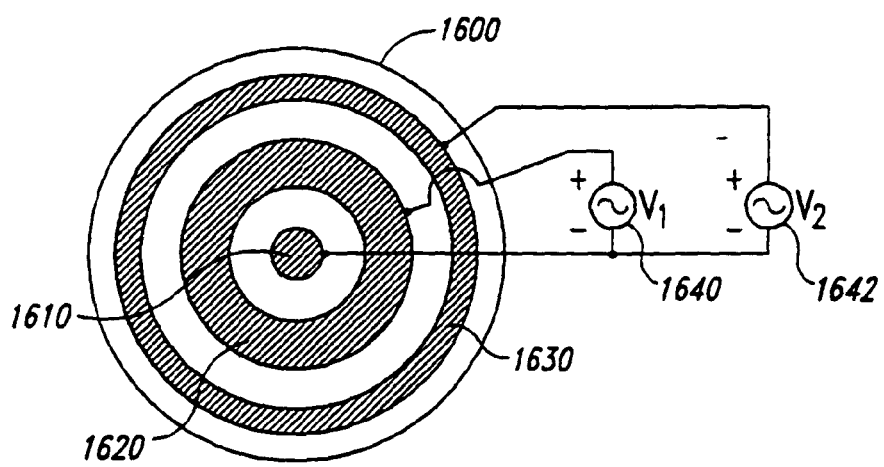
FIG. 16 is a bottom plan view.
Figure 17:
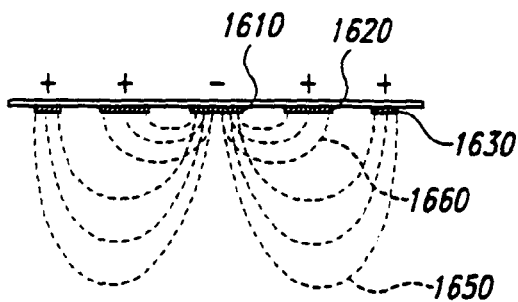
FIG. 17 is a cross-sectional view of an electrode configuration for an implantable stimulation apparatus in accordance with another embodiment of the invention.

FIG. 16 is a bottom plan view and FIG. 17 is a cross-sectional view of a stimulation apparatus 1600 in accordance with another embodiment of the invention. In this embodiment, the stimulation apparatus 1600 includes a first electrode 1610, a second electrode 1620 surrounding the first electrode 1610, and a third electrode 1630 surrounding the second electrode 1620. The first electrode 1610 can be coupled to the negative terminals of a first pulse generator 1640 and a second pulse generator 1642; the second electrode 1620 can be coupled to the positive terminal of the first pulse generator 1640; and the third electrode 1630 can be coupled to the positive terminal of the second pulse generator 1642. In operation, the first electrode 1610 and the third electrode 1630 generate a first toroidal electric field 1650, and the first electrode the 1610 and the second electrode 1620 generate a second toroidal electric field 1660. The second toroidal electric field 1660 can be manipulated to vary the depth that the first toroidal electric field 1650 projects away from the base of the stimulation apparatus 1600.

Figure 18:
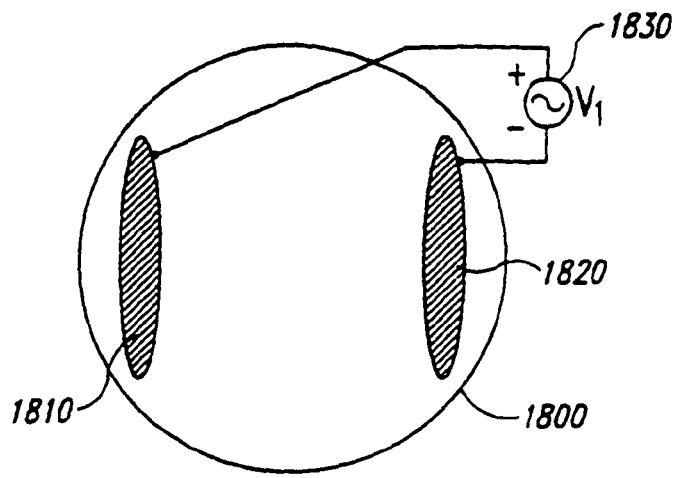
FIG. 18 is a bottom plan view.
Figure 19:
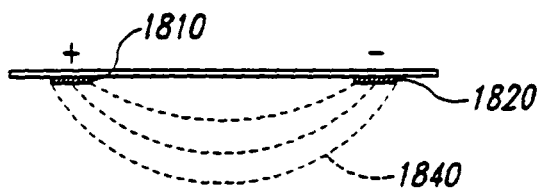
FIG. 19 is a cross-sectional view of an electrode configuration in accordance with yet another embodiment of the invention.

FIG. 18 is a bottom plan view and FIG. 19 is a cross-sectional view of a stimulation apparatus 1800 in accordance with yet another embodiment of the invention. In this embodiment, the stimulation apparatus 1800 includes a first electrode 1810 and a second electrode 1820 spaced apart from the first electrode 1810. The first and second electrodes 1810 and 1820 are linear electrodes which are coupled to opposite terminals of a pulse generator 1830. Referring to FIG. 19, the first and second electrodes 1810 and 1820 can generate an approximately linear electric field.

Figure 20:
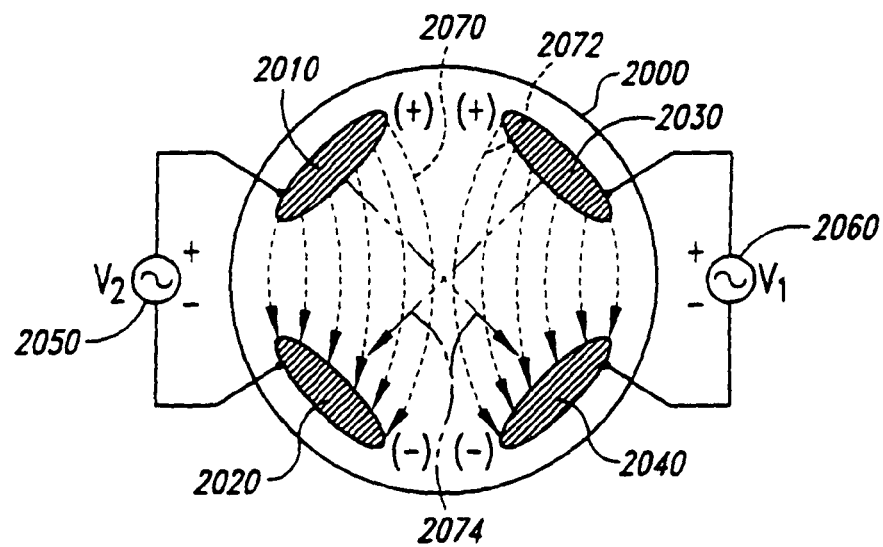
FIG. 20 is a bottom plan view of an electrode configuration for an implantable stimulation device in accordance with yet another embodiment of the invention.

FIG. 20 is a bottom plan view of a stimulation apparatus 2000 in accordance with still another embodiment of the invention. In this embodiment, the stimulation apparatus 2000 includes a first electrode 2010, a second electrode 2020, a third electrode 2030, and a fourth electrode 2040. The first and second electrodes 2010 and 2020 are coupled to a first pulse generator 2050, and the third and fourth electrodes 2030 and 2040 are coupled to a second pulse generator 2060. More specifically, the first electrode 2010 is coupled to the positive terminal and the second electrode 2020 is coupled to the negative terminal of the first pulse generator 2050, and the third electrode 2030 is coupled to the positive terminal and the fourth electrode 2040 is coupled to the negative terminal of the second pulse generator 2060. The first and second electrodes 2010 and 2020 are expected to generate a first electric field 2070, and the third and fourth electrodes 2030 and 2040 are expected to generate a second electric field 2072. It will be appreciated that the ions will be relatively free to move through the brain such that a number of ions will cross between the first and second electric fields 2070 and 2072 as shown by arrows 2074. This embodiment provides control of electric field gradients at the stimulation sites.

FIG. 21 is a bottom plan view of another embodiment of the stimulation apparatus 2000. In this embodiment, the first electrode 2010 is coupled to the positive terminal and the second electrode 2020 is coupled to the negative terminal of the first pulse generator 2050. In contrast to the embodiment shown in FIG. 20, the third electrode 2030 is coupled to the negative terminal and the fourth electrode 2040 is coupled to the positive terminal of the second pulse generator 2070. It is expected that this electrode arrangement will result in a plurality of electric fields between the electrodes. This allows control of the direction or orientation of the electric field.

FIG. 22 is a bottom plan view that schematically illustrates a stimulation apparatus 2200 in accordance with still another embodiment of the invention. In this embodiment, the stimulation apparatus 2200 includes a first electrode 2210, a second electrode 2220, a third electrode 2230, and a fourth electrode 2240. The electrodes are coupled to a pulse generator 2242 by a switch circuit 2250. The switch circuit 2250 can include a first switch 2252 coupled to the first electrode 2210, a second switch 2254 coupled to the second electrode 2220, a third switch 2256 coupled to the third electrode 2230, and a fourth switch 2258 coupled to the fourth electrode 2240. In operation, the switches 2252-2258 can be opened and closed to establish various electric fields between the electrodes 2210-2240. For example, the first switch 2252 and the fourth switch 2258 can be closed in coordination with a pulse from the pulse generator 2242 to generate a first electric field 2260, and/or the second switch 2254 and the third switch 2256 can be closed in coordination with another pulse from the pulse generator 2242 to generate a second electric field 2270. The first and second electric fields 2260 and 2270 can be generated at the same pulse to produce concurrent fields or alternating pulses to produce alternating or rotating fields.

FIG. 23 is a bottom plan view and FIG. 24 is a side elevational view of a stimulation apparatus 2300 in accordance with another embodiment of the invention. In this embodiment, the stimulation apparatus 2300 has a first electrode 2310, a second electrode 2320, a third electrode 2330, and a fourth electrode 2340. The electrodes 2310-2340 can be configured in any of the arrangements set forth above with reference to FIGS. 14-22. The electrodes 2310-2340 also include electrically conductive pins 2350 and/or 2360. The pins 2350 and 2360 can be configured to extend below the pial surface of the cortex. For example, because the length of the pin 2350 is less than the thickness of the cortex 709, the tip of the pin 2350 will accordingly conduct the electrical pulses to a stimulation site within the cortex 709 below the pial surface. The length of the pin 2360 is greater than the thickness of the cortex 709 to conduct the electrical pulses to a portion of the brain below the cortex 709, such as a deep brain region 710. The lengths of the pins are selected to conduct the electrical pulses to stimulation sites below the pia mater 708. As such, the length of the pins 2350 and 2360 can be the same for each electrode or different for individual electrodes. Additionally, only a selected portion of the electrodes and the pins can have an exposed conductive area. For example, the electrodes 2310-2340 and a portion of the pins 2350 and 2360 can be covered with a dielectric material so that only exposed conductive material is at the tips of the pins. It will also be appreciated that the configurations of electrodes set forth in FIGS. 14-22 can be adapted to apply an electrical current to stimulation sites below the pia mater by providing pin-like electrodes in a matter similar to the electrodes shown in FIGS. 23 and 24.

Several embodiments of the stimulation apparatus described above with reference to FIGS. 6-24 are expected to be more effective than existing transcranial or subcranial stimulation devices. In addition to positioning the electrodes under the skull, many embodiments of the stimulation apparatus described above also accurately focus the electrical energy in desired patterns relative to the pia mater 708, the dura mater 706, and/or the cortex 709. It will be appreciated that transcranial devices may not accurately focus the energy because the electrodes or other types of energy emitters are positioned relatively far from the stimulation sites and the skull diffuses some of the energy. Also, existing subcranial devices generally merely place the electrodes proximate to a specific nerve, but they do not provide electrode configurations that generate an electrical field in a pattern designed for the stimulation site. Several of the embodiments of the stimulation apparatus described above with reference to FIGS. 6-24 overcome this drawback because the electrodes can be placed against the neurons at the desired stimulation site. Additionally, the electrode configurations of the stimulation apparatus can be configured to provide a desired electric field that is not diffused by the skull 700. Therefore, several embodiments of the stimulation apparatus in accordance with the invention are expected to be more effective because they can accurately focus the energy at the stimulation site.

4. Implantable Stimulation Apparatus with Biasing Elements

FIGS. 25-30 illustrate several embodiments of stimulation apparatus having a biasing element in accordance with a different aspect of the invention. The stimulation apparatus shown in FIGS. 25-30 can be similar to those described above with reference to FIGS. 6-24. Therefore, the embodiments of the stimulation apparatus shown in FIGS. 25-30 can have the same pulse systems, support members and electrode configurations described above with reference to FIGS. 6-24.

Figure 25:
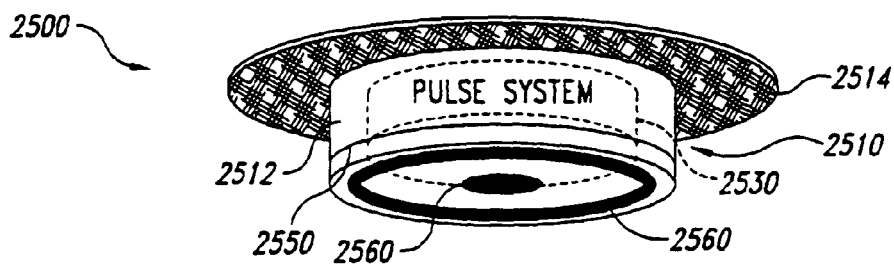
FIG. 25 is an isometric view schematically illustrating a part of an implantable stimulation apparatus with a mechanical biasing element in accordance with an embodiment of the invention.
Figure 26:
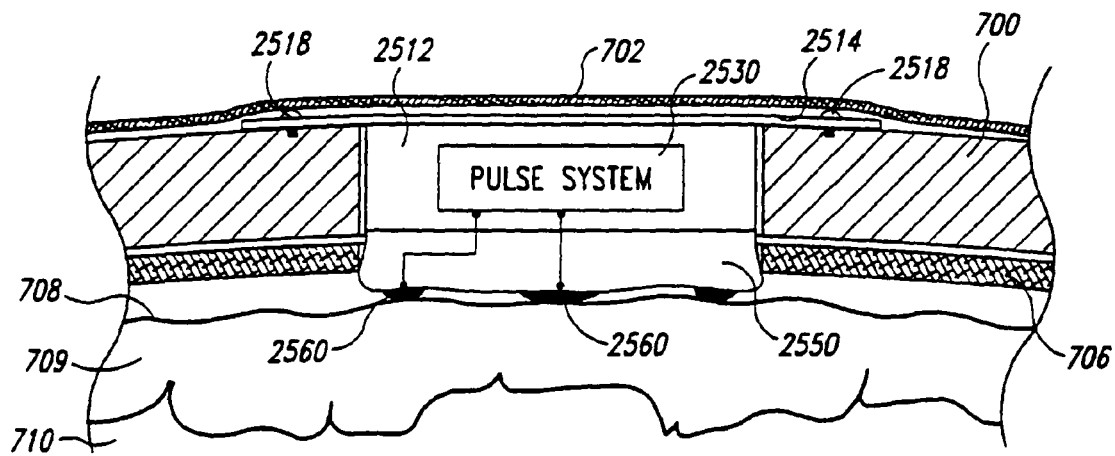
FIG. 26 is a cross-sectional view of a stimulation apparatus having a mechanical biasing element that has been implanted into a skull of a patient in accordance with an embodiment of the invention.

FIG. 25 is an isometric view and FIG. 26 is a cross-sectional view of a stimulation apparatus 2500 in accordance with an embodiment of the invention. In one embodiment, the stimulation apparatus 2500 includes a support member 2510, a pulse-system 2530 carried by the support member 2510, and first and second electrodes 2560 coupled to the pulse system 2530. The support member 2510 can be identical or similar to the support member 610 described above with reference to FIGS. 6 and 7. The support member 2510 can accordingly include a housing 2512 configured to be implanted in the skull 700 and an attachment element 2514 configured to be connected to the skull 700 by fasteners 2518 (FIG. 2), an adhesive, and/or an anchor. The pulse system 2530 can be identical or similar to any of the pulse systems described above with reference to FIGS. 6-13, and the first and second electrodes 2560 can have any of the electrode configurations explained above with reference to FIGS. 14-24. Unlike the stimulation apparatus described above, however, the stimulation apparatus 2500 includes a biasing element 2550 coupled to the electrodes 2560 to mechanically bias the electrodes 2560 away from the support member 2510. In an alternative embodiment, the biasing element 2550 can be positioned between the housing 2512 and the attachment element 2514, and the electrodes 2560 can be attached directly to the housing 2512. As explained in more detail below, the biasing element 2550 can be a compressible member, a fluid filled bladder, a spring, or any other suitable element that resiliently and/or elastically drives the electrodes 2560 away from the support member 2510.

FIG. 26 illustrates an embodiment of the stimulation apparatus 2500 after it has been implanted into the skull 700 of a patient. When the fasteners 2518 are attached to the skull 700, the biasing element 2550 should be compressed slightly so that the electrodes 2560 contact the stimulation site. In the embodiment shown in FIG. 26, the compressed biasing element 2550 gently presses the electrodes 2560 against the surface of the pia mater 708. It is expected that the biasing element 2550 will provide a uniform, consistent contact between the electrodes 2560 and the pial surface of the cortex 709. The stimulation apparatus 2500 is expected to be particularly useful when the implantable device is attached to the skull and the stimulation site is on the pia mater 708 or the dura mater 706. It can be difficult to position the contacts against the pia mater 708 because the distance between the skull 700, the dura mater 706, and the pia mater 708 varies within the cranium as the brain moves relative to the skull, and also as the depth varies from one patient to another. The stimulation apparatus 2500 with the biasing element 2550 compensates for the different distances between the skull 700 and the pia mater 708 so that a single type of device can inherently fit several different patients. Moreover, the stimulation apparatus 2500 with the biasing element 2550 adapts to changes as the brain moves within the skull. In contrast to the stimulation apparatus 2500 with the biasing element 2550, an implantable device that does not have a biasing element 2550 may not fit a particular patient or may not consistently provide electrical contact to the pia mater.

Figure 27:
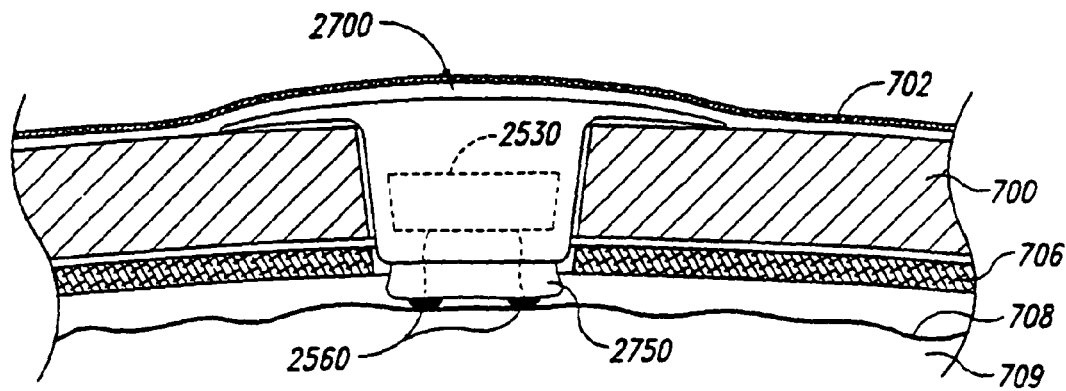
FIG. 27 is a cross-sectional view schematically illustrating a part of a stimulation apparatus having a biasing element in accordance with an embodiment of the invention.
Figure 28:
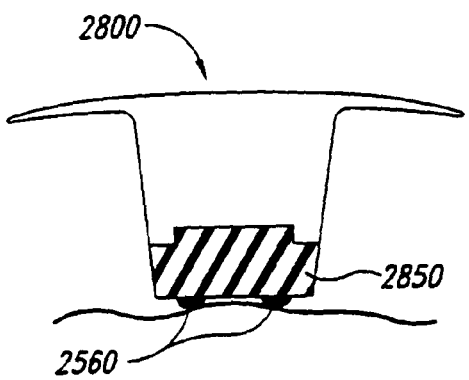
FIG. 28 is a cross-sectional view of a stimulation apparatus having a biasing element in accordance with still another embodiment of the invention.

FIGS. 27 and 28 are cross-sectional views of stimulation apparatus in which the biasing elements are compressible members. FIG. 27, more specifically, illustrates a stimulation apparatus 2700 having a biasing element 2750 in accordance with an embodiment of the invention. The stimulation apparatus 2700 can have an integrated pulse system 2530 and electrodes 2560 coupled to the pulse system 2530 in a manner similar to the stimulation apparatus 2500. The biasing element 2750 in this embodiment is a compressible foam, such as a biocompatible closed cell foam or open cell foam. As best shown in FIG. 27, the biasing element 2750 compresses when the stimulation apparatus 2700 is attached to the skull. FIG. 28 illustrates a stimulation apparatus 2800 having a biasing element 2850 in accordance with another embodiment of the invention. The biasing element 2850 can be a compressible solid, such as silicon rubber or other suitable compressible materials. The electrodes 2560 are attached to the biasing element 2850.

Figure 29:
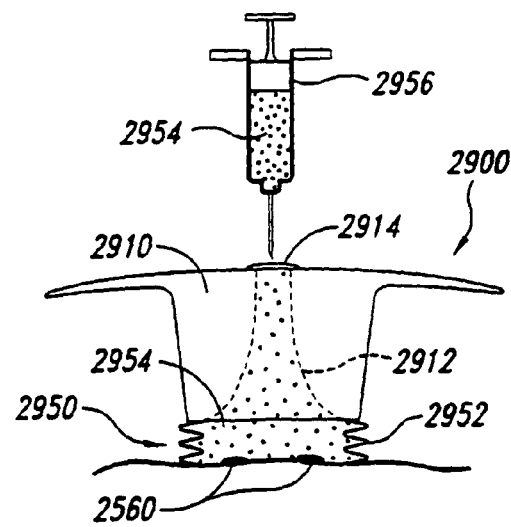
FIG. 29 is a cross-sectional view of a stimulation apparatus having a biasing element in accordance with yet another embodiment of the invention.

FIG. 29 is a cross-sectional view of a stimulation apparatus 2900 having a biasing element 2950 in accordance with another embodiment of the invention. The stimulation apparatus 2900 can have a support member 2910 including an internal passageway 2912 and a diaphragm 2914. The biasing element 2950 can include a flexible bladder 2952 attached to the support member 2910, and the electrodes 2560 can be attached to the flexible bladder 2952. In operation, the flexible bladder 2952 is filled with a fluid 2954 until the electrodes 2560 press against the stimulation site. In one embodiment, the flexible bladder 2952 is filled by inserting a needle of a syringe 2956 through the diaphragm 2914 and injecting the fluid 2954 into the internal passageway 2912 and the flexible bladder.

Figure 30:
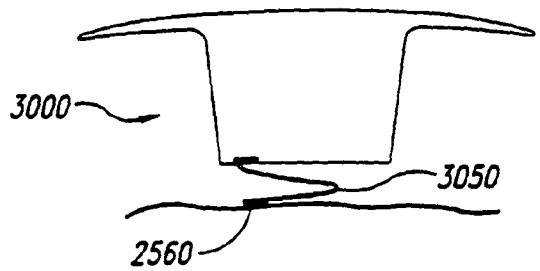
FIG. 30 is a cross-sectional view of a stimulation apparatus having a biasing element in accordance with yet another embodiment of the invention.

FIG. 30 is a cross-sectional view of a stimulation apparatus 3000 having a biasing element 3050 in accordance with another embodiment of the invention. In this embodiment, the biasing element 3050 is a spring and the electrodes 2560 are attached to the spring. The biasing element 3050 can be a wave spring, a leaf spring, or any other suitable spring that can mechanically bias the electrodes 2560 against the stimulation site.

Although several embodiments of the stimulation apparatus shown in FIGS. 25-30 can have a biasing element and any of the pulse systems set forth above with respect to FIGS. 6-13, it is not necessary to have a pulse system contained within the support member. Therefore, certain embodiments of implantable stimulation apparatus in accordance with the invention can have a pulse system and/or a biasing member in any combination of the embodiments set forth above with respect to FIGS. 6-30.

5. Implantable Stimulation Apparatus with External Pulse Systems

Figure 31:
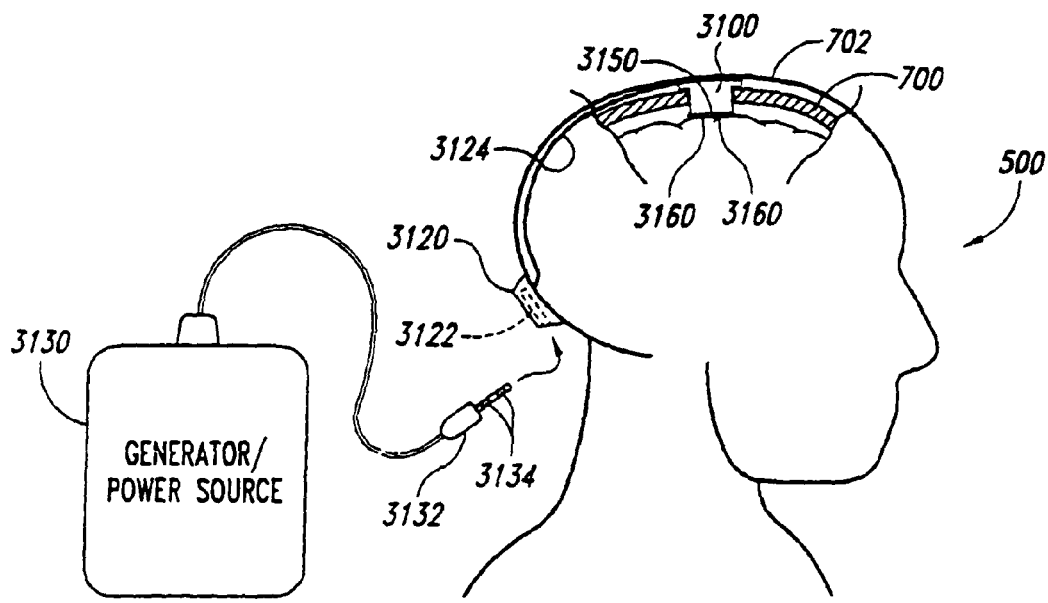
FIG. 31 is a cross-sectional view schematically illustrating a portion of an implantable stimulation apparatus having an external power source and pulse generator in accordance with an embodiment of the invention.

FIGS. 31-35 are schematic cross-sectional views of various embodiments of implantable stimulation apparatus having external pulse systems. FIG. 31, more specifically, illustrates an embodiment of a stimulation apparatus 3100 having a biasing element 3150 to which a plurality of electrodes 3160 are attached in a manner similar to the stimulation apparatus described above with reference to FIGS. 25-30. It will be appreciated that the stimulation apparatus 3100 may not include the biasing element 3150. The stimulation apparatus 3100 can also include an external receptacle 3120 having an electrical socket 3122 and an implanted lead line 3124 coupling the electrodes 3160 to contacts (not shown) in the socket 3122. The lead line 3124 can be implanted in a subcutaneous tunnel or other passageway in a manner known to a person skilled and art.

The stimulation apparatus 3100, however, does not have an internal pulse system carried by the portion of the device that is implanted in the skull 700 of the patient 500. The stimulation apparatus 3100 receives electrical pulses from an external pulse system 3130. The external pulse system 3130 can have an electrical connector 3132 with a plurality of contacts 3134 configured to engage the contacts within the receptacle 3120. The external pulse system 3130 can also have a power supply, controller, pulse generator, and pulse transmitter to generate the electrical pulses. In operation, the external pulse system 3130 sends electrical pulses to the stimulation apparatus 3100 via the connector 3132, the receptacle 3120, and the lead line 3124.

Figure 32:
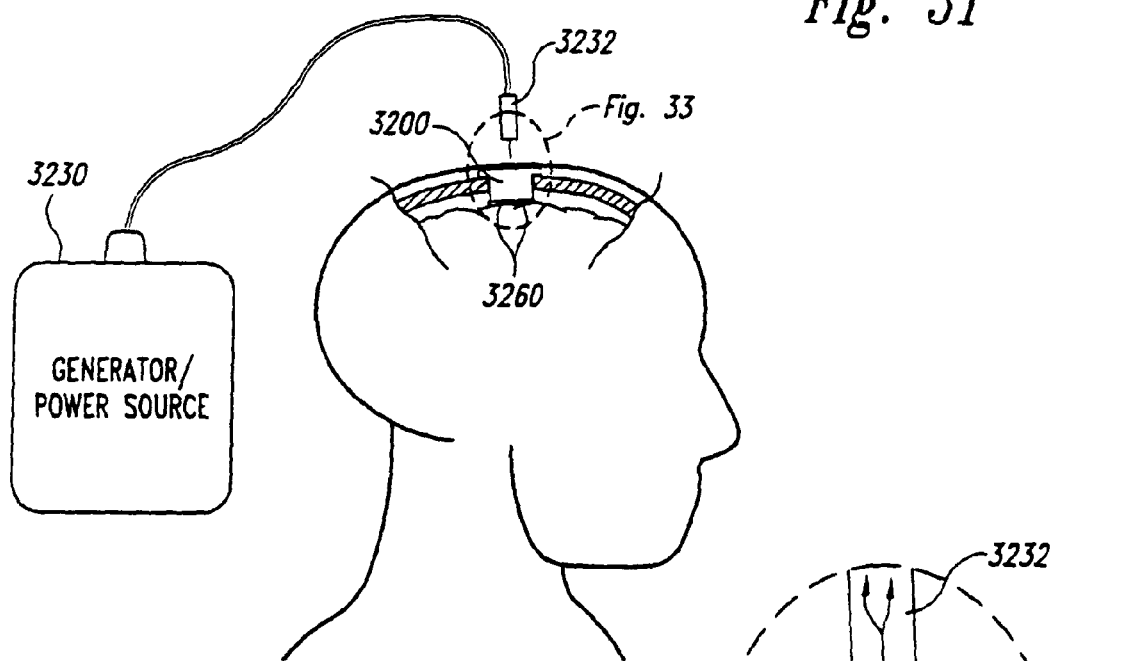
FIG. 32 is a cross-sectional view schematically illustrating a portion of an implantable stimulation apparatus having an external power source and pulse generator in accordance with another embodiment of the invention.
Figure 33:
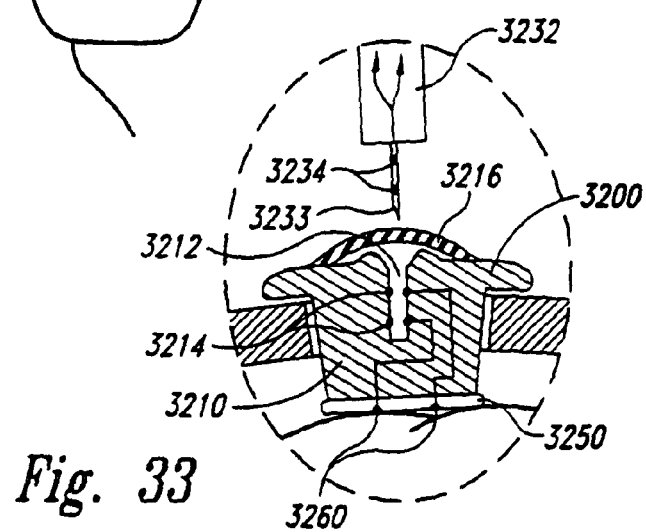
FIG. 33 is a cross-sectional view illustrating in greater detail a portion of the implantable stimulation apparatus of FIG. 32.

FIGS. 32 and 33 illustrate an embodiment of a stimulation apparatus 3200 for use with an external pulse system in accordance with another embodiment of the invention. Referring to FIG. 33, the stimulation apparatus 3200 can include a support structure 3210 having a socket 3212, a plurality of contacts 3214 arranged in the socket 3212, and a diaphragm 3216 covering the socket 3212. The stimulation apparatus 3200 can also include a biasing element 3250 and a plurality of electrodes 3260 attached to the biasing element 3250. Each electrode 3260 is directly coupled to one of the contacts 3214 within the support structure 3210. It will be appreciated that an alternative embodiment of the stimulation apparatus 3200 does not include the biasing element 3250.

Referring to FIGS. 32 and 33 together, the stimulation apparatus 3200 receives the electrical pulses from an external pulse system 3230 that has a power supply, controller, pulse generator, and pulse transmitter. The external pulse system 3230 can also include a plug 3232 having a needle 3233 (FIG. 33) and a plurality of contacts 3234 (FIG. 33) arranged on the needle 3233 to contact the internal contacts 3214 in the socket 3212. In operation, the needle 3233 is inserted into the socket 3212 to engage the contacts 3234 with the contacts 3214, and then the pulse system 3230 is activated to transmit electrical pulses to the electrodes 3260.

Figure 34:
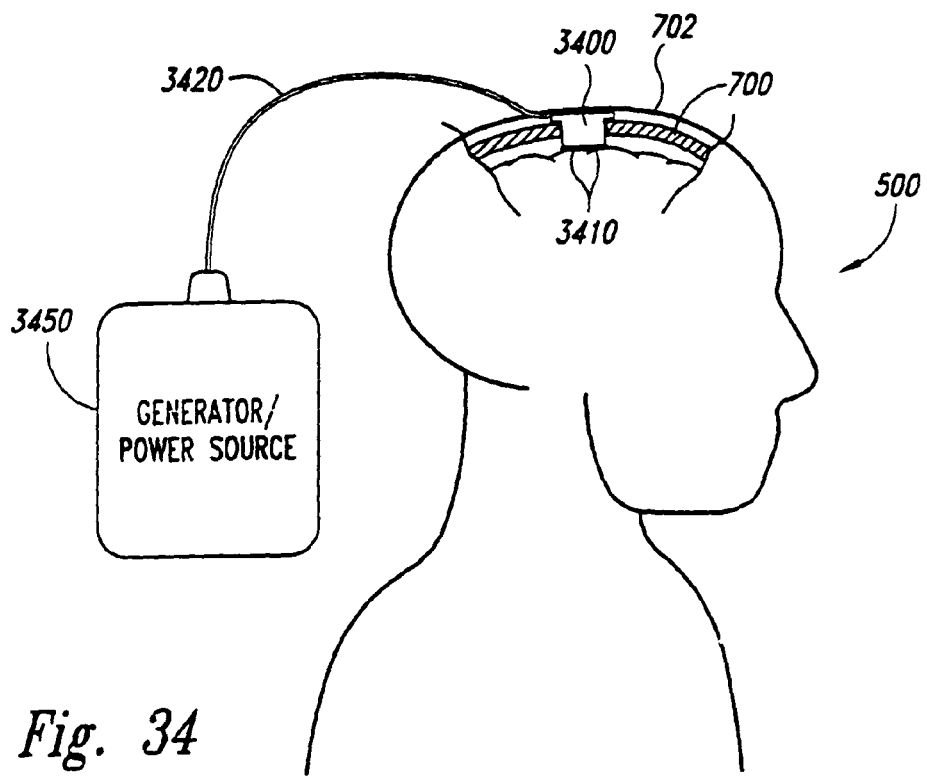
FIG. 34 is a cross-sectional view schematically illustrating a portion of an implantable stimulation apparatus and an external controller in accordance with another embodiment of the invention.
Figure 35:
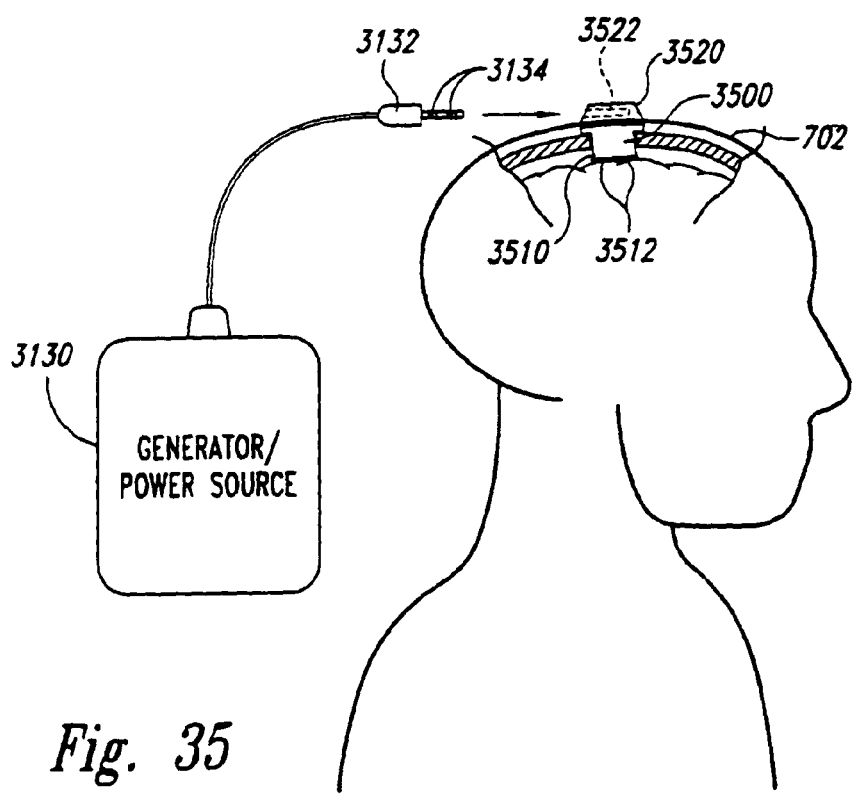
FIG. 35 is a cross-sectional view schematically illustrating a portion of an implantable stimulation apparatus and an external controller in accordance with yet another embodiment of the invention.

FIGS. 34 and 35 illustrate additional embodiments of stimulation apparatus for use with external pulse systems. FIG. 34 illustrates an embodiment of a stimulation apparatus 3400 having electrodes 3410 coupled to a lead line 3420 that extends under the scalp 702 of the patient 500. The lead line 3420 is coupled to an external pulse system 3450. FIG. 35 illustrates an embodiment of a stimulation apparatus 3500 having a support member 3510, electrodes 3512 coupled to the support member 3510, and an external receptacle 3520 mounted on the scalp 702. The external receptacle 3520 can also be connected to the support member 3510. The external receptacle 3520 can have a socket 3522 with contacts (not shown) electrically coupled to the electrodes 3512. The stimulation apparatus 3500 can be used with the external pulse system 3130 described above with reference to FIG. 31 by inserting the plug 3132 into the socket 3522 until the contacts 3134 on the plug 3132 engage the contacts within the socket 3522.

6. Alternate Embodiments of Implantable Stimulation Apparatus

Figure 36:
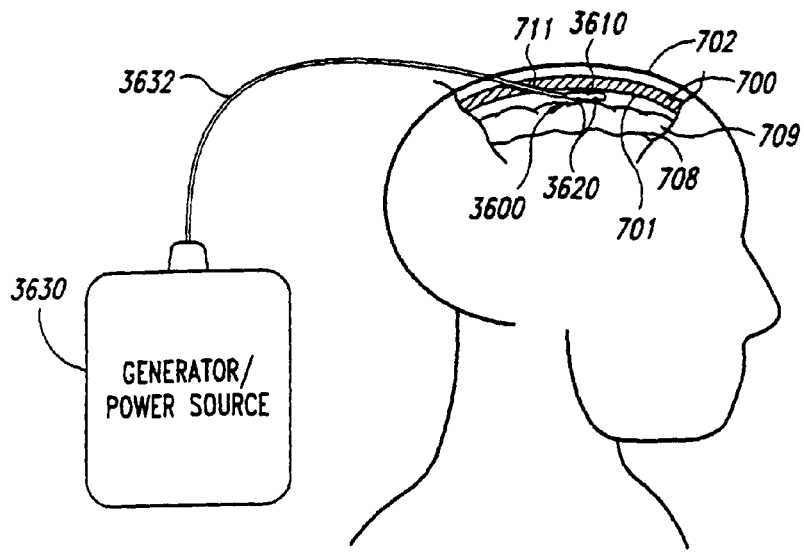
FIG. 36 is a cross-sectional view schematically illustrating a portion of an implantable stimulation apparatus in accordance with yet another embodiment of the invention.

FIG. 36 is a schematic cross-sectional view of an implantable stimulation apparatus 3600 in accordance with another embodiment of the invention. In one embodiment, the stimulation apparatus 3600 has a support structure 3610 and a plurality of electrodes 3620 coupled to the support structure 3610. The support structure 3610 can be configured to be implanted under the skull 700 between an interior surface 701 of the skull 700 and the pial surface of the brain. The support structure 3610 can be a flexible or compressible body such that the electrodes 3620 contact the pia mater 708 when the stimulation apparatus 3600 is implanted under the skull 700. In other embodiments, the support structure 3610 can position the electrodes 3620 so that they are proximate to, but not touching, the pia mater 708.

In one embodiment, the stimulation apparatus 3600 can receive electrical pulses from an external controller 3630. For example, the external controller 3630 can be electrically coupled to the stimulation apparatus 3600 by a lead line 3632 that passes through a hole 711 in the skull 700. In an alternative embodiment, the stimulation apparatus 3600 can include an integrated pulse system similar to the pulse systems described above with reference to FIGS. 6-13. Such an embodiment of the stimulation apparatus 3600 can accordingly use a wireless external control unit. It will be appreciated that the electrodes 3620 of the stimulation apparatus 3600 can have several of the electrode configurations described above with reference to FIGS. 14-24.

Figure 37:
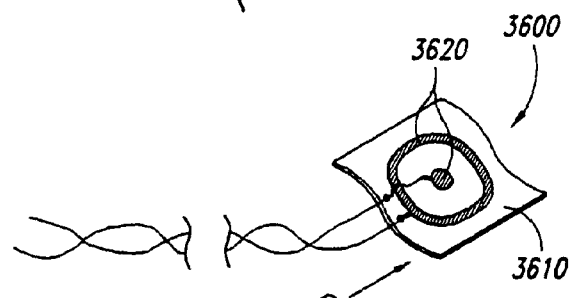
FIG. 37 is an isometric view.
Figure 38:
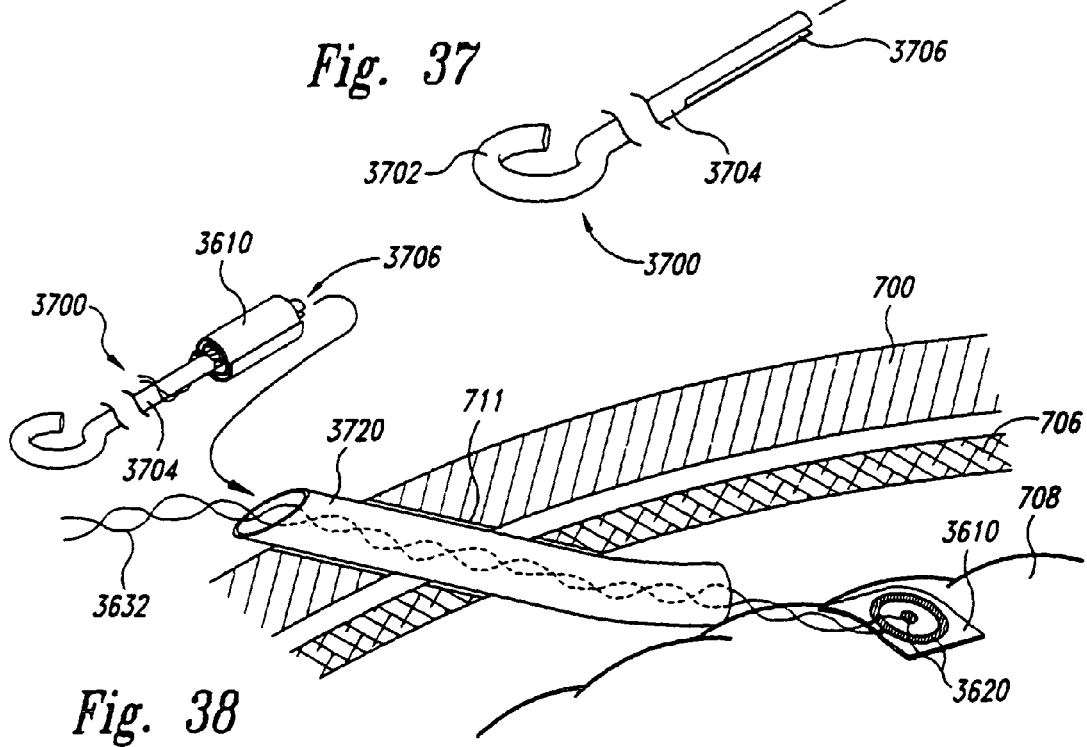
FIG. 38 is a cross-sectional view illustrating an implantable stimulation apparatus in accordance with an embodiment of the invention.

FIGS. 37 and 38 illustrate one embodiment of the implantable stimulation apparatus 3600. Referring to FIG. 37, the support structure 3610 can be a flexible substrate and the electrodes 3620 can be conductive elements that are printed onto the flexible substrate. The stimulation apparatus 3600, for example, can be manufactured in a manner similar to flexible printed circuit assemblies that are used in electrical components. The stimulation apparatus 3600 can be implanted under the skull 700 using an insertion tool 3700. In one embodiment, the insertion tool 3700 has a handle 3702 and a shaft 3704 projecting from the handle 3702. The shaft 3704 can have a slot 3706 configured to receive a flat portion of the support member 3610. Referring to FIG. 38, the support member 3610 is wrapped around the shaft 3704, and then the stimulation apparatus 3600 is passed to a tube 3720 positioned in the hole 711 through the scalp 700 and the dura mater 706. After the stimulation apparatus 3600 has been passed through the tube 3720, it is unfurled to place the electrodes 3620 at least proximate to the pia mater 708. The electrodes 3620 can be coupled to an external controller by the lead lines 3632.

Figure 39:
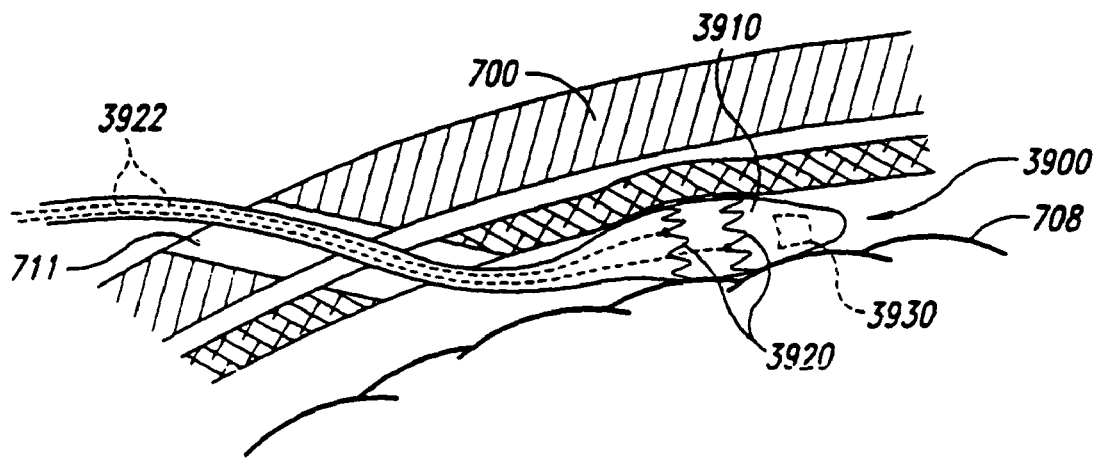
FIG. 39 is a cross-sectional view illustrating an implantable stimulation apparatus in accordance with yet another embodiment of the invention.

FIG. 39 illustrates another embodiment of an implantable stimulation apparatus 3900 that is also configured to be positioned between the skull 700 and the pia mater 708. In one embodiment, the stimulation apparatus 3900 can include a support member 3910 and a plurality of electrodes 3920 coupled to the support member 3910. The electrodes 3920 can be coupled to individual lead lines 3922 to connect the electrodes 3920 to an external pulse system. In an alternative embodiment, an integrated pulse system 3930 can be carried by the support member 3910 so that the electrodes 3920 can be coupled directly to the integrated pulse system 3930 without external lead lines 3922. The support member 3910 can be a resiliently compressible member, an inflatable balloon-like device, or a substantially solid incompressible body. In the particular embodiment shown in FIG. 39, the support member 3910 is an inflatable balloon-like device that carries the electrodes 3920. In operation, the stimulation apparatus 3900 is implanted by passing the distal end of the support member 3910 through the hole 711 in the skull 700 until the electrodes 3920 are positioned at a desired stimulation site.

Figure 40:
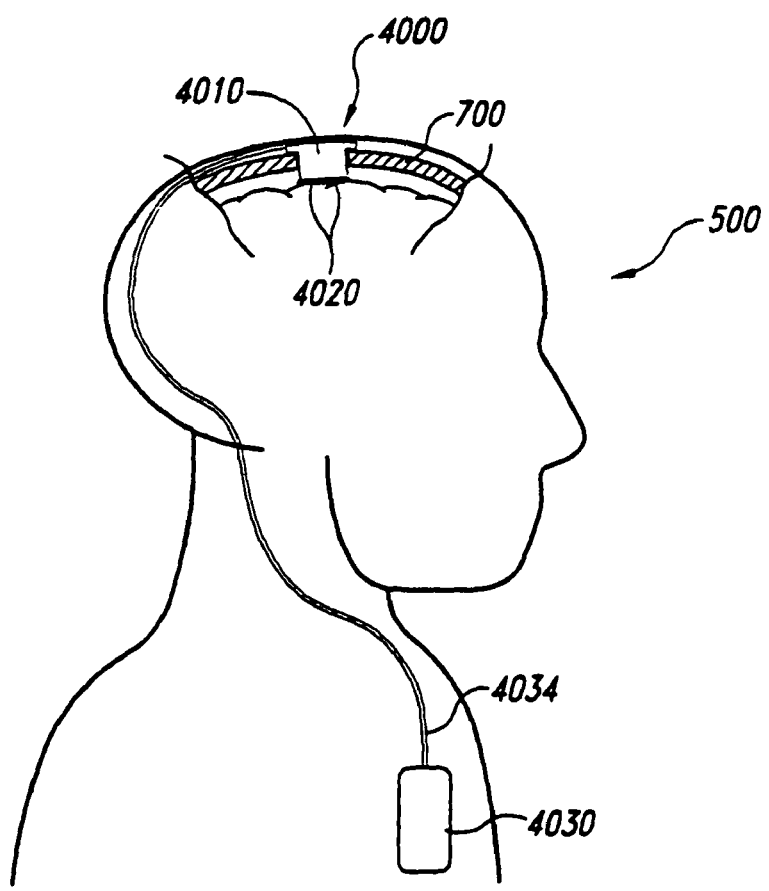
FIG. 40 is a schematic illustration of an implantable stimulation apparatus in accordance with an embodiment of the invention.

FIG. 40 is a schematic illustration of a stimulation apparatus 4000 together with an internal pulse system 4030 in accordance with another embodiment of the invention. The stimulation apparatus 4000 can include a support member 4010, a biasing element 4015 carried by the support member 4010, and a plurality of electrodes 4020 carried by the biasing element 4015. The internal pulse system 4030 can be similar to any of the integrated pulse systems described above with reference to FIGS. 6-13, but the internal pulse system 4030 is not an integrated pulse system because it is not carried by the housing 4010. The internal pulse system 4030 can be coupled to the electrodes 4020 by a cable 4034. In a typical application, the cable 4034 is implanted subcutaneously in a tunnel from a subclavicular region, along the back of the neck, and around the skull. The stimulation apparatus 4000 can also include any of the electrode configurations described above with reference to FIGS. 14-24.

From the foregoing, it will be appreciated that specific embodiments of the invention have been described herein for purposes of illustration, but that various modifications may be made without deviating from the spirit and scope of the invention. Accordingly, the invention is not limited except as by the appended claims.

The invention claimed is:

1. A method of effectuating a neural-function of a patient, comprising:
    selecting a stimulation site by (a) generating an intended neural activity by triggering a neural signal from an impaired body part affected by neural dysfunction of the patient's brain, wherein triggering a neural signal includes moving, stimulating or moving and stimulating the impaired body part, (b) detecting a cortical region of the brain in which a response to neural activity occurs in reaction to the neural signal, the detected cortical region being at a cortical location of the brain different than a normal cortical location of the brain where neural activity typically occurs to carry out a function of the impaired body part, and (c) selecting the stimulation site to be within the detected cortical region;
    positioning at least a first electrode at the stimulation site; and
    applying an electrical potential to pass a current through the first electrode.

2. The method of claim 1 wherein moving the impaired body part comprises passively moving the impaired body part.

3. The method of claim 1 wherein moving the impaired body part comprises passively moving the impaired body part via attaching the impaired body part to a passive motion machine that moves the impaired body part through a defined motion.

4. The method of claim 1 wherein stimulating the impaired body part comprises applying an electrical stimulation to the impaired body part.

5. The method of claim 1 wherein stimulating the impaired body part comprises applying an electrical stimulation to a nerve of the impaired body part.

6. The method of claim 1 wherein moving the impaired body part includes directly contacting and moving the impaired body part.

7. The method of claim 1 wherein detecting a region of the brain includes detecting a region of the brain using fMRI.

8. The method of claim 1 wherein applying an electrical potential includes applying an electrical potential at a level that raises a resting potential of neurons at the stimulation site to a subthreshold level.

9. The method of claim 8 wherein applying an electrical potential includes applying an electrical potential to achieve a change in a resting potential of neurons at the stimulation site of approximately 10%-95% of a difference between an unstimulated resting potential and a threshold potential for the neurons.

10. The method of claim 8 wherein applying an electrical potential includes applying an electrical potential to achieve a change in a resting potential of neurons at the stimulation site of approximately 60%-80% of a difference between an unstimulated resting potential and a threshold potential for the neurons.

11. A method of effectuating a neural-function of a patient, comprising:
    selecting a stimulation site by (a) generating an intended neural activity by triggering a neural signal from an impaired body part affected by neural dysfunction of the patient's brain, wherein triggering a neural signal includes moving, stimulating, or moving and stimulating the impaired body part, (b) detecting a cortical region of the brain in which a response to neural activity occurs in reaction to the neural signal, the detected cortical region being at a cortical location of the brain different than a dysfunctional, normal cortical location of the brain where neural activity typically occurs to carry out a function of the impaired body part, and (c) selecting the stimulation site to be within the detected cortical region; and
    applying an electrical signal directly to the stimulation site effective to carry out the neural function.

12. The method of claim 11 wherein moving the impaired body part comprises passively moving the impaired body part.

13. The method of claim 11 wherein moving the impaired body part comprises passively moving the impaired body part via attaching the impaired body part to a passive motion machine that moves the impaired body part through a defined motion.

14. The method of claim 11 wherein stimulating the impaired body part comprises applying an electrical stimulation to the impaired body part.

15. The method of claim 11 wherein stimulating the impaired body part comprises applying an electrical stimulation to a nerve of the impaired body part.

16. A method of effectuating a neural-function of a patient, comprising:
- selecting a stimulation site by (a) activating a neural signal from an impaired body part affected by neural dysfunction of the patient's brain, wherein activating a neural signal includes moving, stimulating, or moving and stimulating the impaired body part, (b) detecting a cortical region where a response to neural activity occurs in the brain of the patient in reaction to the neural signal associated with the impaired body part, the detected cortical region being at a cortical location of the brain different than a normal cortical location of the brain where neural activity typically occurs to carry out a function of the impaired body part, and (c) selecting the stimulation site to be within the detected cortical region; and
- applying an electrical stimulation directly to the stimulation site.

17. The method of claim 16 wherein moving the impaired body part comprises passively moving the impaired body part.

18. The method of claim 16 wherein moving the impaired body part comprises passively moving the impaired body part by attaching the impaired body part to a passive motion machine that moves the impaired body part through a defined motion.

19. The method of claim 16 wherein stimulating the impaired body part comprises applying an electrical stimulation to the impaired body part.

20. The method of claim 16 wherein stimulating the impaired body part comprises applying an electrical stimulation to a nerve of the impaired body part.

21. A method for treating a patient, comprising:
- selecting a signal delivery site by a process that comprises:
- applying a signal directly to a portion of the patient's body external to the patient's brain to trigger a neural signal from an impaired body part affected by neural dysfunction of the patient's brain;
- detecting a cortical region of the brain in which a response to neural activity occurs in response to the neural signal, the detected cortical region being at a cortical location of the brain different than a dysfunctional, normal cortical location of the brain where neural activity typically occurs to carry out a function of the impaired body part; and
- selecting the signal delivery site to be within the detected cortical region; and
- passing an electrical current through the signal delivery site.

22. The method 21 of claim wherein applying a signal includes applying an electrical signal.

23. The method of claim 21 wherein applying a signal directly to a portion of the patient's body includes applying a signal directly to the impaired body part.

24. The method of claim 21 wherein detecting a region of the brain includes detecting a region of the brain using fMRI.

25. The method of claim 21 wherein applying an electrical potential includes applying an electrical potential at a level that raises a resting potential of neurons at the stimulation site to a subthreshold level.

26. The method of claim 21 wherein applying an electrical potential includes applying an electrical potential to achieve a change in a resting potential of neurons at the stimulation site of approximately 10%-95% of a difference between an unstimulated resting potential and a threshold potential for the neurons.

27. The method of claim 21 wherein applying an electrical potential includes applying an electrical potential to achieve a change in a resting potential of neurons at the stimulation site of approximately 60%-80% of a difference between an unstimulated resting potential and a threshold potential for the neurons.

28. A method of effectuating a neural-function of a patient, comprising:
- selecting a stimulation site by (a) triggering a neural signal from an impaired body part affected by neural dysfunction of the patient's brain, wherein triggering a neural signal includes moving, stimulating or moving and stimulating the impaired body part, (b) detecting a cortical region of the brain in which a response to neural activity occurs in reaction to the neural signal, the detected cortical region being at a cortical location of the brain different than a dysfunctional, normal cortical location of the brain where neural activity typically occurs to carry out a function of the impaired body part, and (c) selecting the stimulation site to be within the detected cortical region;
- positioning at least a first electrode within the patient's skull, external to a cortical surface of the brain at the stimulation site; and
- applying an electrical potential to pass a current through the first electrode.

29. The method of claim 28 wherein selecting a stimulation site includes selecting a stimulation site on a patent-specific basis.

30. A method of effectuating a neural-function of a patient, comprising:
- selecting one or more stimulation sites by (a) triggering a neural signal from an impaired body part affected by neural dysfunction of the patient's brain, wherein triggering a neural signal includes moving, stimulating or moving and stimulating the impaired body part, (b) detecting a cortical region of the brain in which a response to neural activity occurs in reaction to the neural signal, and (c) selecting the patient's brain stimulation sites to be located within the patient's skull, within the detected cortical region, and on a cortical surface of the brain;
- positioning at least a first electrode at the one or more stimulation sites; and
- applying an electrical potential to pass a current through the first electrode.

31. The method of claim 30 wherein moving the impaired body part comprises passively moving the impaired body part.

32. The method of claim 30 wherein moving the impaired body part comprises passively moving the impaired body part by attaching the impaired body part to a passive motion machine that moves the impaired body part through a defined motion.

33. The method of claim 30 wherein stimulating the impaired body part comprises applying an electrical stimulation to the impaired body part.

34. The method of claim 30 wherein stimulating the impaired body part comprises applying an electrical stimulation to a nerve of the impaired body part.

* * * * *